United States Patent
Tan et al.

(10) Patent No.: US 10,828,312 B2
(45) Date of Patent: Nov. 10, 2020

(54) LITHIUM CHOLESTEROL COMPOSITIONS, INCLUDING, BUT NOT LIMITED TO LITHIUM CHOLESTEROL SULFATE COMPOSITIONS, AND METHODS OF TREATMENT FOR ALZHEIMER'S DISEASE AND NEUROLOGICAL DISORDERS

(71) Applicants: Jun Tan, Tampa, FL (US); Roland Douglas Shytle, Largo, FL (US); Jinhua Wen, Tampa, FL (US); Darrell Sawmiller, Land O'Lakes, FL (US)

(72) Inventors: Jun Tan, Tampa, FL (US); Roland Douglas Shytle, Largo, FL (US); Jinhua Wen, Tampa, FL (US); Darrell Sawmiller, Land O'Lakes, FL (US)

( * ) Notice: Subject to any disclaimer, the term of this patent is extended or adjusted under 35 U.S.C. 154(b) by 0 days.

(21) Appl. No.: 16/432,367

(22) Filed: Jun. 5, 2019

(65) Prior Publication Data
US 2020/0129527 A1 Apr. 30, 2020

Related U.S. Application Data

(60) Provisional application No. 62/752,251, filed on Oct. 29, 2018.

(51) Int. Cl.
A61K 31/575 (2006.01)
A61K 9/00 (2006.01)
A61P 25/00 (2006.01)

(52) U.S. Cl.
CPC .......... *A61K 31/575* (2013.01); *A61K 9/0053* (2013.01); *A61P 25/00* (2018.01)

(58) Field of Classification Search
CPC ...... A61K 31/575; A61K 9/0053; A61P 25/00
USPC ....................................................... 514/171
See application file for complete search history.

(56) References Cited

U.S. PATENT DOCUMENTS

| | | | |
|---|---|---|---|
| 5,043,165 A | * | 8/1991 | Radhakrishnan .... A61K 9/0073 424/450 |
| 2013/0245253 A1 | | 9/2013 | Marx et al. |
| 2018/0296487 A1 | * | 10/2018 | Saporito ................ A61K 9/146 |

FOREIGN PATENT DOCUMENTS

| | | | | |
|---|---|---|---|---|
| EP | 0954317 B1 | 6/2007 | | |
| WO | 2010119455 | 10/2010 | | |
| WO | WO-2010119455 A2 | * | 10/2010 | ........... A61K 9/1647 |
| WO | 2011120044 A1 | 9/2011 | | |

OTHER PUBLICATIONS

Alexander MP; et al Lithium Toxicity: A Double-Edged Sword. Kidney Int. 2008;73(2):233-7.

Al-Horani RA; et al "Chemical Sulfation of Small Molecules—Advances and Challenges." Tetrahedron. 2010;66 (16):2907-18.
Bandyopadhyay B; et al "Tau Aggregation and Toxicity in a Cell Culture Model of Tauopathy." The Journal of biological chemistry. 2007;282(22):16454-64.
Beel AJ; et al "Direct Binding of Cholesterol to the Amyloid Precursor Protein: An Important Interaction in Lipid-Alzheimer's Disease Relationships?" Biochimica et biophysica acta. 2010;1801(8):975-82.
Blumberg SJ; et al "Changes in Prevalence of Parent-Reported Autism Spectrum Disorder in School-Aged U.S. Children: 2007 to 2011-2012." National health statistics reports. 2013(65):1-11, 1 p.
Canitano R. "Mood Stabilizers in Children and Adolescents With Autism Spectrum Disorders." Clinical neuropharmacology. 2015;38(5):177-82.
Choi SE; et al "Atherosclerosis Induced by a High-Fat Diet is Alleviated by Lithium Chloride via Reduction of VCAM Expression in ApoE-Deficient Mice." Vascular pharmacology. 2010;53(5-6):264-72.
Clayton KA; et al "Alzheimer's Disease: The Role of Microglia in Brain Homeostasis and Proteopathy." Frontiers in neuroscience. 2017;11:680.
Cussotto S; et al "Differential Effects of Psychotropic Drugs on Microbiome Composition and Gastrointestinal Function." Psychopharmacology. 2018.
Devanand DP; et al "Lithium Treatment for Agitation in Alzheimer's Disease (Lit-AD): Clinical Rationale and Study Design." Contemporary clinical trials. 2018;71:33-9.
Devanand DP; et al "Low-dose Lithium Treatment for Agitation and Psychosis in Alzheimer Disease and Frontotemporal Dementia: A Case Series." Alzheimer disease and associated disorders. 2017;31(1):73-5.
Donazzolo E; et al "Improved Synthesis of Glycine, Taurine and Sulfate Conjugated Bile Acids as Reference Compounds and Internal Standards for ESI-MS/MS Urinary Profiling of Inborn Errors of Bile Acid Synthesis." Chemistry and physics of lipids. 2017;204:43-56.
Drayer NM; et al "Isolation of Cholesterol Sulfate From Human Blood and Gallstones." Biochemical and biophysical research communications. 1965;18:126-30.

(Continued)

*Primary Examiner* — Yong L Chu
(74) *Attorney, Agent, or Firm* — Thomas | Horstemeyer, LLP

(57) ABSTRACT

In one aspect, the disclosure relates to compositions of lithium cholesterol compositions, including but not limited to lithium cholesterol sulfate compositions which are useful as therapeutic agents. The disclosure also relates to methods of making lithium cholesterol compositions and pharmaceutical compositions comprising therapeutically effective amounts of the lithium cholesterol compositions. The present disclosure also includes methods of treating one or more clinical neurological conditions with the lithium cholesterol compositions, such as Alzheimer's disease, autism spectrum disorder, bipolar disorder, or other neuropsychiatric disorders.

6 Claims, 7 Drawing Sheets

(56) References Cited

OTHER PUBLICATIONS

Fitzpatrick SE; et al "Aggression in Autism Spectrum Disorder: Presentation and Treatment Options." Neuropsychiatric disease and treatment. 2016;12:1525-38.
Foglia F; et al "Neutron Scattering Studies of the Effects of Formulating Amphotericin B with Cholesteryl Sulfate on the Drug's Interactions with Phospholipid and Phospholipid-Sterol Membranes." Langmuir : the ACS journal of surfaces and colloids. 2015;31(29):8042-51.
Gassowska M; et al "Perinatal Exposure to Lead (Pb) Promotes Tau Phosphorylation in the Rat Brain in a GSK-3beta and CDK5 Dependent Manner: Relevance to Neurological Disorders." Toxicology. 2016;347-349:17-28.
Habib A; et al "LISPRO Mitigates Beta-Amyloid and Associated Pathologies in Alzheimer's Mice." Cell death & disease. 2017;8(6):e2880.
Matsunaga S; et al "Lithium as a Treatment for Alzheimer's Disease: A Systematic Review and Meta-Analysis." Journal of Alzheimer's disease : JAD. 2015;48(2):403-10.
Merten M; et al "Cholesterol Sulfate: A New Adhesive Molecule for Platelets." Circulation. 2001;103(16):2032-4.
Nielsen J; et al "Dysregulation of Renal Aquaporins and Epithelial Sodium Channel in Lithium-Induced Nephrogenic Diabetes Insipidus." Semin Nephrol. 2008;28(3):227-44.
Kim S; et al "Lithium Chloride Suppresses LPS-Mediated Matrix Metalloproteinase-9 Expression in Macrophages Through Phosphorylation of GSK-3beta." Cell biology international. 2015;39(2):177-84.
Oruch R; et al "Lithium: A Review of Pharmacology, Clinical Uses, and Toxicity." European journal of pharmacology. 2014;740:464-73.
Przybylska M; et al "Cholesterol Sulfate Induces Changes in Human Erythrocyte Thermostability." Biochemistry and molecular biology international. 1998;46(2):399-410.
Ralay Ranaivo H; et al "Albumin Induces Upregulation of Matrix Metalloproteinase-9 in Astrocytes Via MAPK and Reactive Oxygen Species-Dependent Pathways." Journal of neuroinflammation. 2012;9:68.
Rodrigueza WV; et al "Transbilayer Movement and Net Flux of Cholesterol and Cholesterol Sulfate Between Liposomal Membranes." Biochemistry. 1995; 34 (18):6208-17.
Scheltens P; et al "Alzheimer's Disease." Lancet (London, England). 2016;388(10043):505-17.
Seneff S; et al "Might Cholesterol Sulfate Deficiency Contribute to the Development of Autistic Spectrum Disorder?" Medical hypotheses. 2012;78(2):213-7.
Serret S; et al "Lithium as a Rescue Therapy for Regression and Catatonia Features in Two SHANK3 Patients With Autism Spectrum Disorder: Case Reports." BMC psychiatry. 2015;15:107.
Siegel M; et al "Preliminary Investigation of Lithium for Mood Disorder Symptoms in Children and Adolescents with Autism Spectrum Disorder." Journal of child and adolescent psychopharmacology. 2014;24(7)399-402.
Smith AJ; et al "Plasma and Brain Pharmacokinetics of Previously Unexplored Lithium Salts." RSC advances. 2014;4 (24):12362-5.
Smith AJ; et al "Improving Lithium Therapeutics by Crystal Engineering of Novel Ionic Cocrystals." Mol Pharm. 2013;10 (12):4728-38.
Strott CA; et al "Cholesterol Sulfate in Human Physiology: What's it All About?" J Lipid Res. 2003;44(7):1268-78.
Theoharides TC; et al "Atopic Diseases and Inflammation of the Brain in the Pathogenesis of Autism Spectrum Disorders." Translational psychiatry. 2016;6(6):e844.
Wang J; et al "A Systemic View of Alzheimer Disease—Insights from Amyloid-Beta Metabolism Beyond the Brain." Nature reviews Neurology. 2017;13(11):703.
Willing AE; et al "Lithium Exposure Enhances Survival of NT2N Cells (hNT Neurons) in the Hemiparkinsonian Rat." The European journal of neuroscience. 2002;16(12):2271-8.
Wu X; et al "Lithium Ameliorates Autistic-Like Behaviors Induced by Neonatal Isolation in Rats." Frontiers in behavioral neuroscience. 2014;8:234.
Yang Y; et al "Matrix Metalloproteinases as Therapeutic Targets for Stroke." Brain research. 2015;1623:30-8.
Young W. "Review of Lithium Effects on Brain and Blood." Cell transplantation. 2009;18(9):951-75.
Zhu H; et al "Phase I-II Clinical Trial Assessing Safety and Efficacy of Umbilical Cord Blood Mononuclear Cell Transplant Therapy of Chronic Complete Spinal Cord Injury." Cell transplantation. 2016;25(11):1925-43.
Zigova T; et al "Lithium Chloride Induces the Expression of Tyrosine Hydroxylase in hNT Neurons." Experimental neurology. 1999;157(2):251-8.
Richardson T; et al "Clinically Relevant Treatment Considerations Regarding Lithium Use in Bipolar Disorder." Expert opinion on drug metabolism & toxicology. 2017;13(11):1105-13.
International Search Report and Written Opinion for PCT/US2019/035546 dated Sep. 4, 2019.
Frost, et al. Clinical Uses of Lithium Salts. Brain Research Bulletin, 1983, vol. 11, pp. 219-231.
Schou, et al. The Treatment of Manic Psychoses by the Administration of Lithium Salts. J. Neurol. Neurosurg. Psychiat., 1954, vol. 17, pp. 250.
Lithium for Bipolar Disorder, WebMD, Accessed Mar. 16, 2018. Available: https://www.webmd.com/bipolar-disorder/guide/bipolar-disorder-lithium?print=true.
Leeds, et al. A New Avenue for Lithium: Intervention in Traumatic Brain Injury. ACS Chemical Neuroscience, 2014, vol. 5, pp. 422-433.
Newman, et al. Assessing the Impact of Lithium Chloride on the Expression of P-Glycoprotein at the Blood-Brain Barrier. Journal of Pharmaceutical Sciences, 2017, vol. 106, pp. 2625-2631.

* cited by examiner

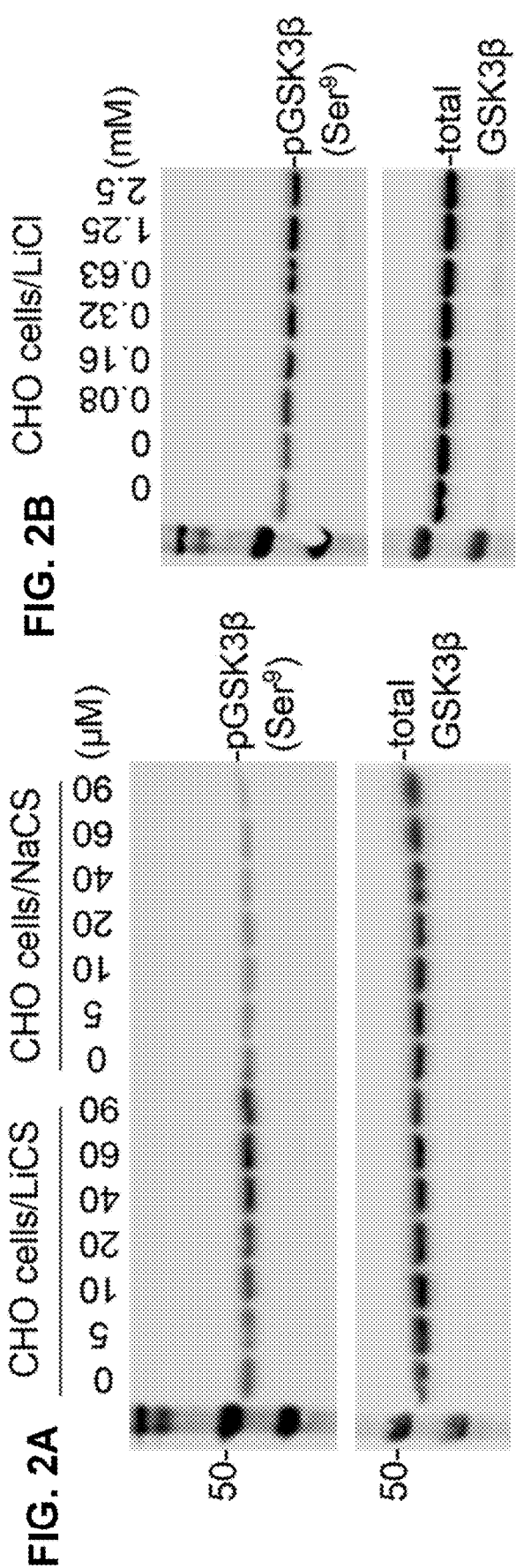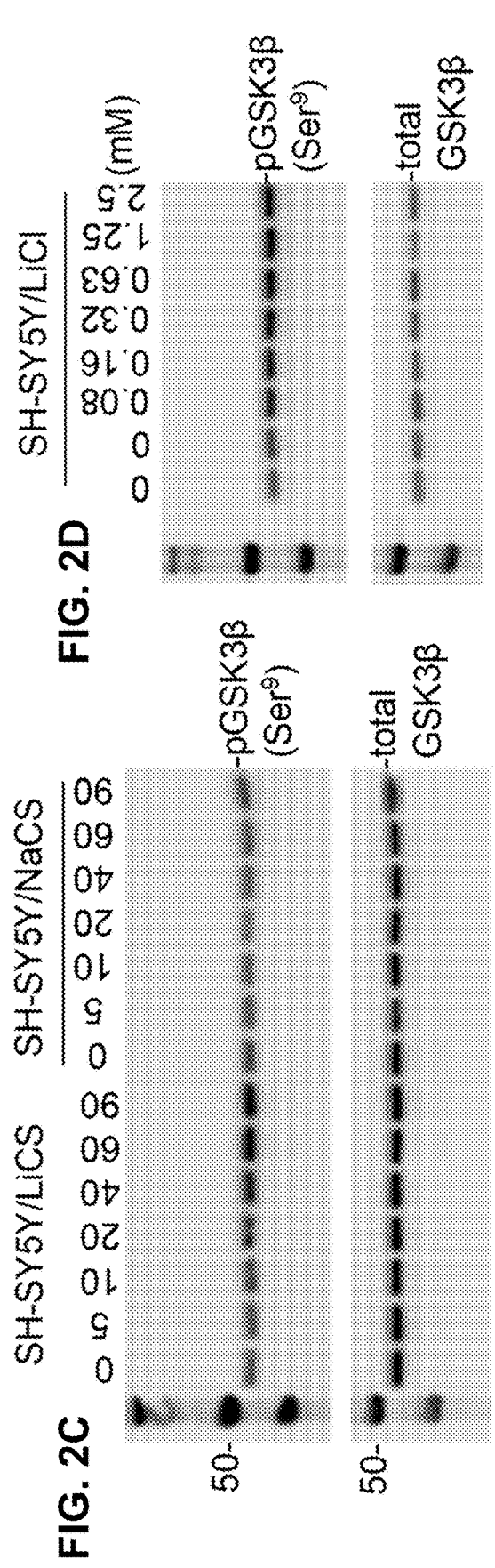

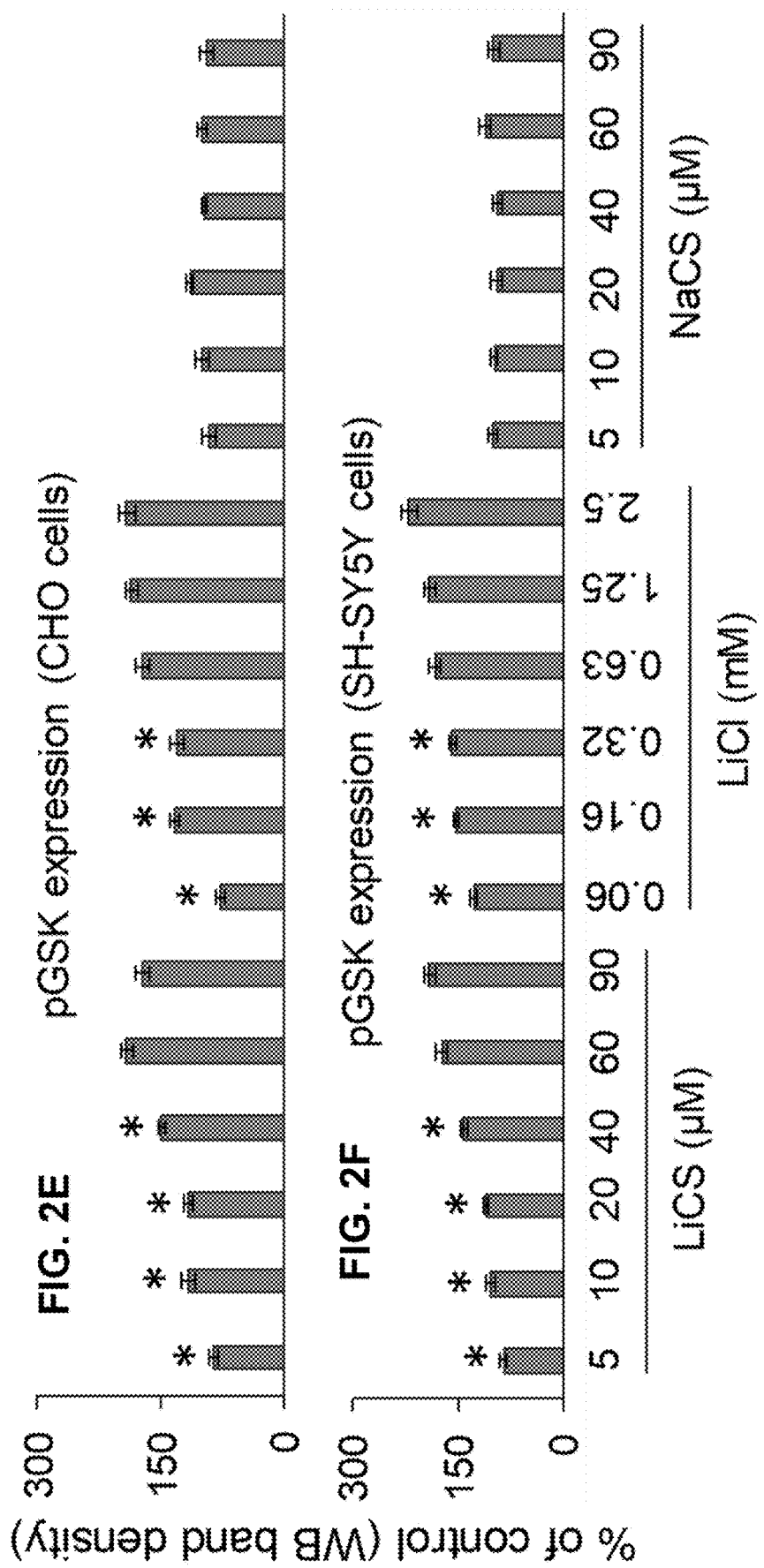

| | Lithium levels in brain, kidney and liver at 0.5 and 5 h after LiCl and LiCS p.o. treatment (ng/mg protein) | | | |
|---|---|---|---|---|
| | LiCl | | LiCS | |
| | 0.5 h | 5 h | 0.5 h | 5 h |
| Brain | N.D. | 0.72 ± 0.06 | 0.49 ± 0.03 | 0.79 ± 0.01 |
| Kidney | 0.74 ± 0.36 | 0.61 ± 0.24 | N.D. | N.D. |
| Liver | N.D. | N.D. | N.D. | N.D. |

N.D. = Non-detectable

LITHIUM CHOLESTEROL COMPOSITIONS, INCLUDING, BUT NOT LIMITED TO LITHIUM CHOLESTEROL SULFATE COMPOSITIONS, AND METHODS OF TREATMENT FOR ALZHEIMER'S DISEASE AND NEUROLOGICAL DISORDERS

CROSS-REFERENCE RELATED APPLICATION

This Application claims the benefit of U.S. Provisional Application entitled "Use of the lithium salt of cholesterol sulfate (LCS) for preventing and treating Alzheimer's disease, suicidal ideation, bipolar disorder, traumatic brain injury, radiation induced brain injury, and autism," having Ser. No. 62/752,251, filed on Oct. 29, 2018, which is incorporated herein by reference in its entirety.

BACKGROUND

Alzheimer's disease (AD), a progressive neurodegenerative disease represents the main cause of dementia and one of the great health-care challenges of the 21st century. AD causes severe distress for patients and their caregivers and results in a large societal economic burden. While AD is neurodegenerative, Autism spectrum disorder (ASD), is neurodevelopmental disorder afflicting up to 20 out of 100 children aged 6-17 in the United States (8). The cause of autism appears to be primarily genetic, but recent studies also indicate the presence of a strong inflammatory state associated with ASD (9).

Lithium salts, long used in psychiatry to treat bipolar disorder, are still considered as a first-line therapy for both the acute and long-term treatment of bipolar disorder (11). Recent studies demonstrated neuroprotective effects of lithium salts, including preventing apoptosis and increasing neurotrophins and other cell-survival molecules (12). Beneficial effects of lithium salts on neurogenesis, angiogenesis, inflammation, and other neurological functions have been revealed, indicating the possible use of lithium salts in the treatment of AD and related neurological disorders (13). Unfortunately, despite the long use of lithium salts in the treatment of bipolar disorder, there remain drawbacks to the use of the current, clinically available lithium salts. Concerns such as potential for toxicity, need for monitoring of side effects, and patient compliance limit the use of currently available lithium salts for broader treatment of neurological conditions.

SUMMARY

In accordance with the purpose(s) of the disclosure, as embodied and broadly described herein, the disclosure, in various aspects, relates to lithium cholesterol compounds and compositions, pharmaceutical compositions including therapeutically effective amounts of lithium cholesterol compositions, kits including lithium cholesterol pharmaceutical compositions, and methods of using the pharmaceutical compositions including lithium cholesterol compounds for the treatment of a neurological disorder.

Pharmaceutical compositions of the present disclosure, in various aspects, comprise a therapeutically effective amount of a lithium cholesterol composition, and a pharmaceutically acceptable carrier; wherein the lithium cholesterol composition has a structure having the formula:

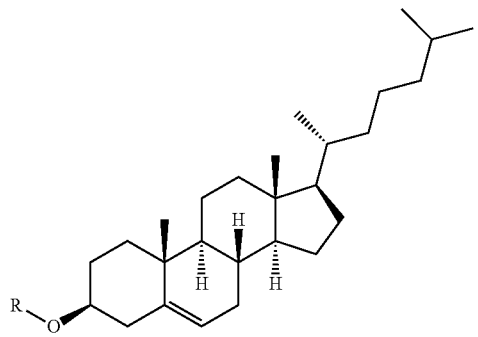

where R is selected from —SO$_3$Li, PO$_3$(Li)$_2$, —(CH$_2$)$_n$(C=O)OLi, or —(C=O)(CH$_2$)$_n$(C=O)OLi, where n is integer selected from 1, 2, 3, 4, 5, and 6. In embodiments of the pharmaceutical compositions of the present disclosure, the lithium cholesterol composition is selected from a structure having the formula:

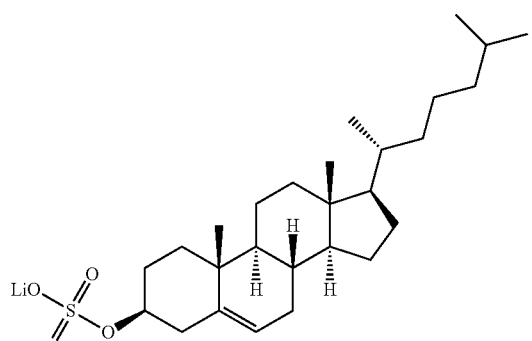

,

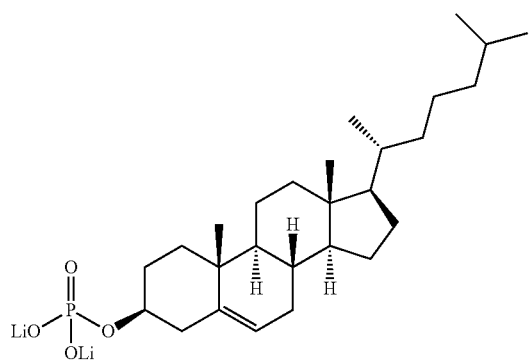

,

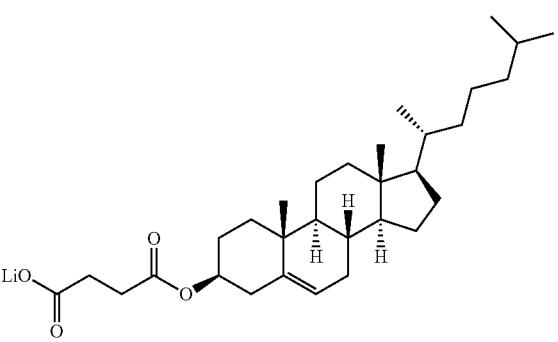

,

-continued

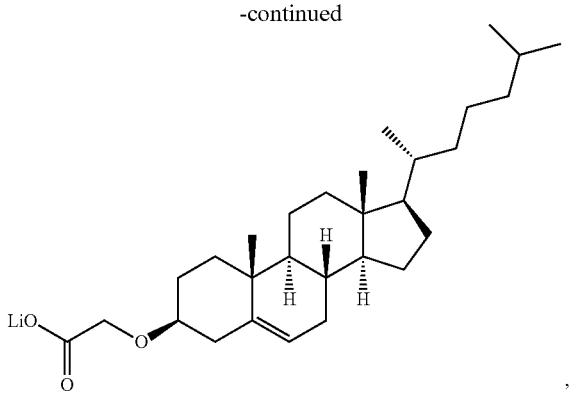

and combinations thereof. In some embodiments, lithium cholesterol composition is a lithium cholesterol sulfate structure having the formula:

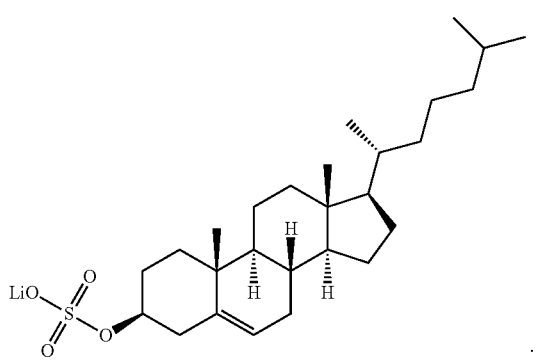

The present disclosure also provides, in various aspects, kits comprising a lithium cholesterol pharmaceutical composition of the present disclosure and instructions for administering the compound to treat a neurological disorder. In embodiments, the kits also include at least one additional therapeutic agent for treatment of the neurological disorder and instructions for administering the additional therapeutic agent with the lithium cholesterol pharmaceutical composition.

Also provided are methods of treatment for a neurological disorder by administering to a subject in need of treatment for a neurological disorder a therapeutically effective amount of a pharmaceutical composition comprising a therapeutically effective amount of a lithium cholesterol composition, and a pharmaceutically acceptable carrier; wherein the lithium cholesterol composition has a structure having the formula:

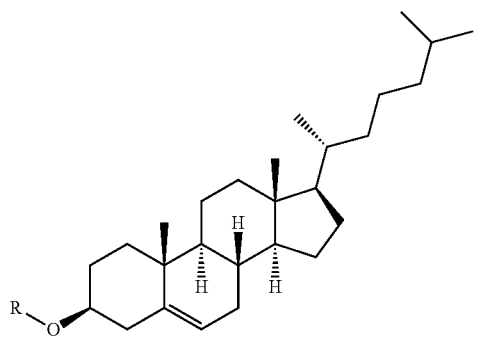

where R is selected from $-SO_3Li$, $-PO_3(Li)_2$, $-(CH_2)_n(C=O)OLi$, or $-(C=O)(CH_2)_n(C=O)OLi$, where n is integer selected from 1, 2, 3, 4, 5, and 6. In embodiments, the neurological disorder is selected from: Alzheimer's disease, autism spectrum disorder (ASD), Parkinson's disease, suicidal ideation, bipolar disorder, mood disorders, traumatic brain injury, radiation induced brain injury, amyotrophic laterals sclerosis, schizoaffective disorder, and tic disorder. In embodiments of the methods of the present disclosure, administration of the pharmaceutical composition produces one or more of the following effects in the subject: increasing levels of inhibitory phosphorylation of GSK3β, decreasing levels of phosphorylation of tau, and decreasing levels of LPS-induced TNFα, as compared to the levels of said compounds in a subject not receiving treatment with the pharmaceutical composition. In embodiments, administration of the pharmaceutical composition produces a greater brain to blood lithium level ratio in the subject than administration of lithium chloride and/or does not substantially increase lithium levels in the liver or kidney of the subject.

In a further aspect, the disclosed compositions comprise a compound produced by a synthetic method described herein. In a still further aspect, the present disclosure comprises a method for manufacturing a medicament comprising combining at least one product of the disclosed methods with a pharmaceutically acceptable carrier or diluent.

Other systems, methods, features, and advantages of the present disclosure will be or will become apparent to one with skill in the art upon examination of the following drawings and detailed description. It is intended that all such additional systems, methods, features, and advantages be included within this description, and be within the scope of the present disclosure.

BRIEF DESCRIPTION OF THE DRAWINGS

Further aspects of the present disclosure will be more readily appreciated upon review of the detailed description of its various embodiments, described below, when taken in conjunction with the accompanying drawings.

FIGS. 2A-F illustrate a comparison of LiCS and LiCl in mediating inhibitory GSK3β phosphorylation. CHO (FIGS. 2A and 2B) and SH-SY5Y cell cultures (FIGS. 2C and 2D) were treated with LiCS or NaCS at 0-90 μM or LiCl at 60 μM to 2.5 mM for 18 h followed by analysis of inhibitory phospho-GSK3β (Ser9) and total GSK3β levels in cell homogenates by WB. Levels of phospo-GSK3β (Ser9) were determined by densitometry analysis of three independent experiments and represented as mean±SD in the graphs presented in FIGS. 2E and 2F. Asterisk indicates P<0.05 compared with no treatment (control, 100%). Note that NaCS did not alter pGSK3β and neither LiCS, LiCl nor NaCS altered total GSK3β levels.

Figures 5A, 5B:
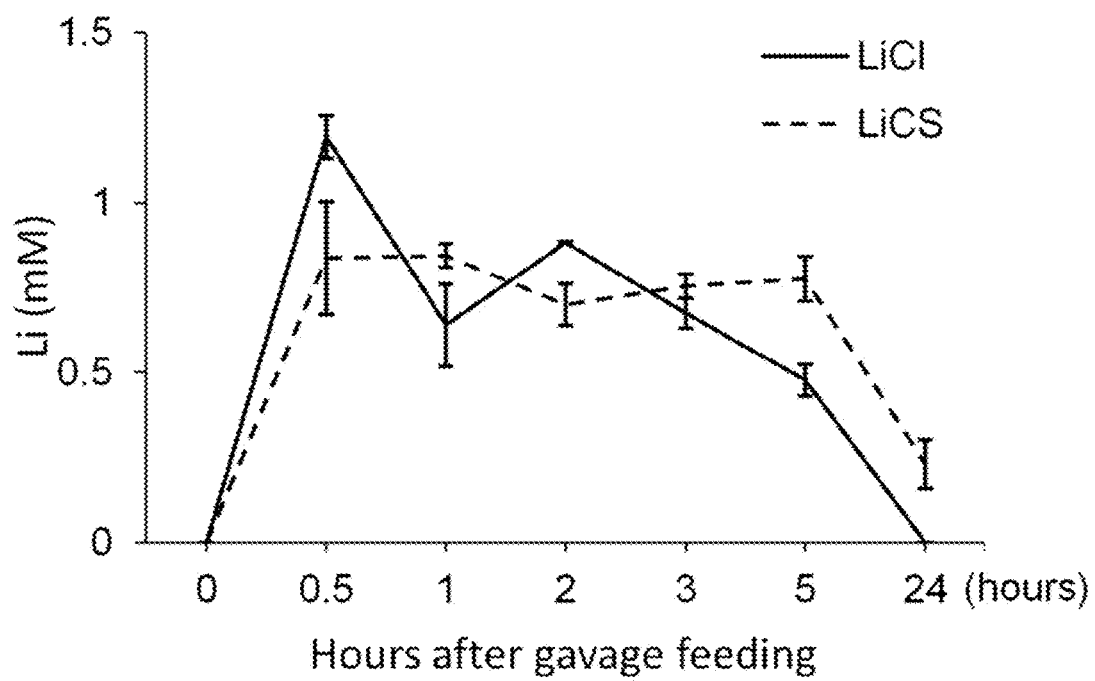

The graph in FIG. 5A and table in FIG. 5B illustrate the pharmacokinetics of lithium cholesterol sulfate (LiCS) in adult male mice. The graph in FIG. 5A illustrates the comparison of lithium levels in the blood after treatment with LiCl and LiCS at 0.5, 1, 2, 3, 5 and 24 h after oral administration, where the table in FIG. 5B presents the comparison of lithium levels in brain, kidney and liver at 0.5 and 5 h after gavage. Lithium ELISA results are presented as the mean (+s.d.). Asterisk indicates P<0.05 versus LiCl treatment as determined by ANOVA.

DETAILED DESCRIPTION

Before the present disclosure is described in greater detail, it is to be understood that this disclosure is not limited to particular embodiments described, as such may, of course, vary. It is also to be understood that the terminology used herein is for the purpose of describing particular embodiments only, and is not intended to be limiting, since the scope of the present disclosure will be limited only by the appended claims.

Where a range of values is provided, it is understood that each intervening value, to the tenth of the unit of the lower limit (unless the context clearly dictates otherwise), between the upper and lower limit of that range, and any other stated or intervening value in that stated range, is encompassed within the disclosure. The upper and lower limits of these smaller ranges may independently be included in the smaller ranges and are also encompassed within the disclosure, subject to any specifically excluded limit in the stated range. Where the stated range includes one or both of the limits, ranges excluding either or both of those included limits are also included in the disclosure. For example, where the stated range includes one or both of the limits, ranges excluding either or both of those included limits are also included in the disclosure, e.g. the phrase "x to y" includes the range from 'x' to 'y' as well as the range greater than 'x' and less than 'y'. The range can also be expressed as an upper limit, e.g. 'about x, y, z, or less' and should be interpreted to include the specific ranges of 'about x', 'about y', and 'about z' as well as the ranges of 'less than x', less than y', and 'less than z'. Likewise, the phrase 'about x, y, z, or greater' should be interpreted to include the specific ranges of 'about x', 'about y', and 'about z' as well as the ranges of 'greater than x', greater than y', and 'greater than z'. In addition, the phrase "about 'x' to 'y'", where 'x' and 'y' are numerical values, includes "about 'x' to about 'y'".

It is to be understood that such a range format is used for convenience and brevity, and thus, should be interpreted in a flexible manner to include not only the numerical values explicitly recited as the limits of the range, but also to include all the individual numerical values or sub-ranges encompassed within that range as if each numerical value and sub-range is explicitly recited. To illustrate, a numerical range of "about 0.1% to 5%" should be interpreted to include not only the explicitly recited values of about 0.1% to about 5%, but also include individual values (e.g., about 1%, about 2%, about 3%, and about 4%) and the sub-ranges (e.g., about 0.5% to about 1.1%; about 5% to about 2.4%; about 0.5% to about 3.2%, and about 0.5% to about 4.4%, and other possible sub-ranges) within the indicated range.

Unless defined otherwise, all technical and scientific terms used herein have the same meaning as commonly understood by one of ordinary skill in the art to which this disclosure belongs. Although any methods and materials similar or equivalent to those described herein can also be used in the practice or testing of the present disclosure, the preferred methods and materials are now described.

As will be apparent to those of skill in the art upon reading this disclosure, each of the individual embodiments described and illustrated herein has discrete components and features which may be readily separated from or combined with the features of any of the other several embodiments without departing from the scope or spirit of the present disclosure. Any recited method can be carried out in the order of events recited or in any other order that is logically possible.

Embodiments of the present disclosure will employ, unless otherwise indicated, techniques of biochemistry, molecular biology, pharmacology, medicine, neuropathology, and the like, which are within the skill of the art. Such techniques are explained fully in the literature.

The following examples are put forth so as to provide those of ordinary skill in the art with a complete disclosure and description of how to perform the methods and use the compositions and compounds disclosed and claimed herein. Efforts have been made to ensure accuracy with respect to numbers (e.g., amounts, temperature, etc.), but some errors and deviations should be accounted for. Unless indicated otherwise, parts are parts by weight, temperature is in ° C., and pressure is at or near atmospheric. Standard temperature and pressure are defined as 20° C. and 1 atmosphere.

Before the embodiments of the present disclosure are described in detail, it is to be understood that, unless otherwise indicated, the present disclosure is not limited to particular materials, reagents, reaction materials, manufacturing processes, or the like, as such can vary. It is also to be understood that the terminology used herein is for purposes of describing particular embodiments only, and is not intended to be limiting. It is also possible in the present disclosure that steps can be executed in different sequence where this is logically possible.

All publications and patents cited in this specification are cited to disclose and describe the methods and/or materials in connection with which the publications are cited. Publications and patents that are incorporated by reference, where noted, are incorporated by reference as if each individual publication or patent were specifically and individually indicated to be incorporated by reference. Such incorporation by reference is expressly limited to the methods and/or materials described in the cited publications and patents and does not extend to any lexicographical definitions from the cited publications and patents. Any lexicographical definition in the publications and patents cited that is not also expressly repeated in the instant application should not be treated as such and should not be read as defining any terms appearing in the accompanying claims. Any terms not specifically defined within the instant application, including terms of art, are interpreted as would be understood by one of ordinary skill in the relevant art; thus, is not intended for any such terms to be defined by a lexicographical definition in any cited art, whether or not incorporated by reference herein, including but not limited to, published patents and patent applications. The citation of any publication is for its disclosure prior to the filing date and should not be construed as an admission that the present disclosure is not entitled to antedate such publication by virtue of prior disclosure. Further, the dates of publication provided could be different from the actual publication dates that may need to be independently confirmed.

Prior to describing the various embodiments, the following definitions are provided and should be used unless otherwise indicated.

Definitions

In describing and claiming the disclosed subject matter, the following terminology will be used in accordance with the definitions set forth below.

It must be noted that, as used in the specification and the appended claims, the singular forms "a," "an," and "the" include plural referents unless the context clearly dictates otherwise. Thus, for example, reference to "a cell" includes a plurality of cells. In this specification and in the claims that follow, reference will be made to a number of terms that shall be defined to have the following meanings unless a contrary intention is apparent.

As used herein, "comprising" is to be interpreted as specifying the presence of the stated features, integers, steps, or components as referred to, but does not preclude the presence or addition of one or more features, integers, steps, or components, or groups thereof. Moreover, each of the terms "by", "comprising," "comprises", "comprised of," "including," "includes," "included," "involving," "involves," "involved," and "such as" are used in their open, non-limiting sense and may be used interchangeably. Further, the term "comprising" is intended to include examples and aspects encompassed by the terms "consisting essentially of" and "consisting of." Similarly, the term "consisting essentially of" is intended to include examples encompassed by the term "consisting of.

In this disclosure, "consisting essentially of" or "consists essentially" or the like, when applied to methods and compositions encompassed by the present disclosure refers to compositions like those disclosed herein, but which may contain additional structural groups, composition components or method steps (or analogs or derivatives thereof as discussed above). Such additional structural groups, composition components or method steps, etc., however, do not materially affect the basic and novel characteristic(s) of the compositions or methods, compared to those of the corresponding compositions or methods disclosed herein. "Consisting essentially of" or "consists essentially" or the like, when applied to methods and compositions encompassed by the present disclosure have the meaning ascribed in U.S. Patent law and the term is open-ended, allowing for the presence of more than that which is recited so long as basic or novel characteristics of that which is recited is not changed by the presence of more than that which is recited, but excludes prior art embodiments.

As used herein, "about," "approximately," "substantially," and the like, when used in connection with a numerical variable, can generally refers to the value of the variable and to all values of the variable that are within the experimental error (e.g., within the 95% confidence interval for the mean) or within +/−10% of the indicated value, whichever is greater. As used herein, the terms "about," "approximate," "at or about," and "substantially" can mean that the amount or value in question can be the exact value or a value that provides equivalent results or effects as recited in the claims or taught herein. That is, it is understood that amounts, sizes, formulations, parameters, and other quantities and characteristics are not and need not be exact, but may be approximate and/or larger or smaller, as desired, reflecting tolerances, conversion factors, rounding off, measurement error and the like, and other factors known to those of skill in the art such that equivalent results or effects are obtained. In some circumstances, the value that provides equivalent results or effects cannot be reasonably determined. In general, an amount, size, formulation, parameter or other quantity or characteristic is "about," "approximate," or "at or about" whether or not expressly stated to be such. It is understood that where "about," "approximate," or "at or about" is used before a quantitative value, the parameter also includes the specific quantitative value itself, unless specifically stated otherwise.

As used herein, the terms "optional" or "optionally" means that the subsequently described event or circumstance can or cannot occur, and that the description includes instances where said event or circumstance occurs and instances where it does not.

As used herein, "administering" can refer to an administration that is oral, topical, intravenous, subcutaneous, transcutaneous, transdermal, intramuscular, intra-joint, parenteral, intra-arteriole, intradermal, intraventricular, intraosseous, intraocular, intracranial, intraperitoneal, intralesional, intranasal, intracardiac, intraarticular, intracavernous, intrathecal, intravireal, intracerebral, and intracerebroventricular, intratympanic, intracochlear, rectal, vaginal, by inhalation, by catheters, stents or via an implanted reservoir or other device that administers, either actively or passively (e.g. by diffusion) a composition the perivascular space and adventitia. For example a medical device such as a stent can contain a composition or formulation disposed on its surface, which can then dissolve or be otherwise distributed to the surrounding tissue and cells. The term "parenteral" can include subcutaneous, intravenous, intramuscular, intra-articular, intra-synovial, intrasternal, intrathecal, intrahepatic, intralesional, and intracranial injections or infusion techniques. Administration can be continuous or intermittent. In various aspects, a preparation can be administered therapeutically; that is, administered to treat an existing disease or condition. In further various aspects, a preparation can be administered prophylactically; that is, administered for prevention of a disease or condition.

As used herein, "therapeutic agent" can refer to any substance, compound, molecule, and the like, which can be biologically active or otherwise can induce a pharmacologic, immunogenic, biologic and/or physiologic effect on a subject to which it is administered to by local and/or systemic action. A therapeutic agent can be a primary active agent, or in other words, the component(s) of a composition to which the whole or part of the effect of the composition is attributed. A therapeutic agent can be a secondary therapeutic agent, or in other words, the component(s) of a composition to which an additional part and/or other effect of the composition is attributed. The term therefore encompasses those compounds or chemicals traditionally regarded as drugs, vaccines, and biopharmaceuticals including molecules such as proteins, peptides, hormones, nucleic acids, gene constructs and the like. Examples of therapeutic agents are described in well-known literature references such as the Merck Index (14th edition), the Physicians' Desk Reference (64th edition), and The Pharmacological Basis of Therapeutics (12th edition), and they include, without limitation, medicaments; vitamins; mineral supplements; substances used for the treatment, prevention, diagnosis, cure or mitigation of a disease or illness; substances that affect the structure or function of the body, or pro-drugs, which become biologically active or more active after they have been placed in a physiological environment. For example, the term "therapeutic agent" includes compounds or compositions for use in all of the major therapeutic areas including, but not limited to, adjuvants; anti-infectives such as antibiotics and antiviral agents; analgesics and analgesic combinations, anorexics, anti-inflammatory agents, anti-epileptics, local and general anesthetics, hypnotics, sedatives, antipsychotic agents, neuroleptic agents, antidepressants, anxiolytics, antagonists, neuron blocking agents, anticholinergic and cholinomimetic agents, antimuscarinic and muscarinic agents, antiadrenergics, antiarrhythmics, antihypertensive agents, hormones, and nutrients, antiarthritics, antiasthmatic agents, anticonvulsants, antihistamines, antinauseants, antineoplastics, antipruritics, antipyretics; antispasmodics, cardiovascular preparations (including calcium channel blockers, beta-blockers, beta-agonists and antiarrythmics), antihypertensives, diuretics, vasodilators; mood stabilizers; central nervous system stimulants; cough and cold preparations; decongestants; diagnostics; hormones; bone growth stimulants and bone resorption inhibitors; immunosuppressives; muscle relaxants; psychostimulants; sedatives; tranquilizers; proteins, peptides, and fragments thereof (whether naturally occurring, chemically synthesized or recombinantly produced); and nucleic acid molecules (polymeric forms of two or more nucleotides, either ribonucleotides (RNA) or deoxyribonucleotides (DNA) including both double- and single-stranded molecules, gene constructs, expression vectors, antisense molecules and the like), small molecules (e.g., doxorubicin) and other biologically active macromolecules such as, for example, proteins and enzymes. The agent may be a biologically active agent used in medical, including veterinary, applications and in agriculture, such as with plants, as well as other areas. The term therapeutic agent also includes without limitation, medicaments; vitamins; mineral supplements; substances used for the treatment, prevention, diagnosis, cure or mitigation of disease or illness; or substances which affect the structure or function of the body; or pro-drugs, which become biologically active or more active after they have been placed in a predetermined physiological environment.

As used herein, "kit" means a collection of at least two components constituting the kit. Together, the components constitute a functional unit for a given purpose. Individual member components may be physically packaged together or separately. For example, a kit comprising an instruction for using the kit may or may not physically include the instruction with other individual member components. Instead, the instruction can be supplied as a separate member component, either in a paper form or an electronic form which may be supplied on computer readable memory device or downloaded from an internet website, or as recorded presentation.

As used herein, "instruction(s)" means documents describing relevant materials or methodologies pertaining to a kit. These materials may include any combination of the following: background information, list of components and their availability information (purchase information, etc.), brief or detailed protocols for using the kit, trouble-shooting, references, technical support, and any other related documents. Instructions can be supplied with the kit or as a separate member component, either as a paper form or an electronic form which may be supplied on computer readable memory device or downloaded from an internet website, or as recorded presentation. Instructions can comprise one or multiple documents, and are meant to include future updates.

As used herein, "attached" can refer to covalent or non-covalent interaction between two or more molecules. Non-covalent interactions can include ionic bonds, electrostatic interactions, van der Walls forces, dipole-dipole interactions, dipole-induced-dipole interactions, London dispersion forces, hydrogen bonding, halogen bonding, electromagnetic interactions, $\pi$-$\pi$ interactions, cation-T interactions, anion-T interactions, polar $\pi$-interactions, and hydrophobic effects.

As used interchangeably herein, "subject," "individual," or "patient" can refer to a vertebrate organism, such as a mammal (e.g. human). "Subject" can also refer to a cell, a population of cells, a tissue, an organ, or an organism, preferably to human and constituents thereof.

As used herein, the terms "treating" and "treatment" can refer generally to obtaining a desired pharmacological and/or physiological effect. The effect can be, but does not necessarily have to be, prophylactic in terms of preventing or partially preventing a disease, symptom or condition thereof, such as those related to a neurodegenerative condition, and neurodevelopmental disorder, or other neurological disorder, such as but not limited to Alzheimer's disease, autism spectrum disorder, bipolar disorder, suicidal ideation, traumatic brain injury, radiation induced brain injury, and the like. The effect can be therapeutic in terms of a partial or complete cure of a disease, condition, symptom or adverse effect attributed to the disease, disorder, or condition. The term "treatment" as used herein can include any treatment of a neurological disorder in a subject, particularly a human, and can include any one or more of the following: (a) preventing the disease from occurring in a subject which may be predisposed to the disease but has not yet been diagnosed as having it; (b) inhibiting the disease, i.e., arresting its development; and (c) relieving the disease, i.e., mitigating or ameliorating the disease and/or its symptoms or conditions. The term "treatment" as used herein can refer to both therapeutic treatment alone, prophylactic treatment alone, or both therapeutic and prophylactic treatment. Those in need of treatment (subjects in need thereof) can include those already with the disorder and/or those in which the disorder is to be prevented. As used herein, the term "treating", can include inhibiting the disease, disorder or condition, e.g., impeding its progress; and relieving the disease, disorder, or condition, e.g., causing regression of the disease, disorder and/or condition. Treating the disease, disorder, or condition can include ameliorating at least one symptom of the particular disease, disorder, or condition, even if the underlying pathophysiology is not affected, e.g., such as treating the pain of a subject by administration of an analgesic agent even though such agent does not treat the cause of the pain.

As used herein, "dose," "unit dose," or "dosage" can refer to physically discrete units suitable for use in a subject, each unit containing a predetermined quantity of a disclosed compound and/or a pharmaceutical composition thereof calculated to produce the desired response or responses in association with its administration.

As used herein, "therapeutic" can refer to treating, healing, and/or ameliorating a disease, disorder, condition, or side effect, or to decreasing in the rate of advancement of a disease, disorder, condition, or side effect.

As used herein, "effective amount" can refer to the amount of a disclosed compound or pharmaceutical composition provided herein that is sufficient to effect beneficial or desired biological, emotional, medical, or clinical response of a cell, tissue, system, animal, or human.

An effective amount can be administered in one or more administrations, applications, or dosages. The term can also include within its scope amounts effective to enhance or restore to substantially normal physiological function.

As used herein, the term "therapeutically effective amount" refers to an amount that is sufficient to achieve the desired therapeutic result or to have an effect on undesired symptoms, but is generally insufficient to cause adverse side effects. The specific therapeutically effective dose level for any particular patient will depend upon a variety of factors including the disorder being treated and the severity of the disorder the specific composition employed; the age, body weight, general health, sex and diet of the patient; the time of administration; the route of administration; the rate of excretion of the specific compound employed; the duration of the treatment; drugs used in combination or coincidental with the specific compound employed and like factors within the knowledge and expertise of the health practitioner and which may be well known in the medical arts. In the case of treating a particular disease or condition, in some instances, the desired response can be inhibiting the progression of the disease or condition. This may involve only slowing the progression of the disease temporarily. However, in other instances, it may be desirable to halt the progression of the disease permanently. This can be monitored by routine diagnostic methods known to one of ordinary skill in the art for any particular disease. The desired response to treatment of the disease or condition also can be delaying the onset or even preventing the onset of the disease or condition.

For example, it is well within the skill of the art to start doses of a compound at levels lower than those required to achieve the desired therapeutic effect and to gradually increase the dosage until the desired effect is achieved. If desired, the effective daily dose can be divided into multiple doses for purposes of administration. Consequently, single dose compositions can contain such amounts or submultiples thereof to make up the daily dose. The dosage can be adjusted by the individual physician in the event of any contraindications. It is generally preferred that a maximum dose of the pharmacological agents of the invention (alone or in combination with other therapeutic agents) be used, that is, the highest safe dose according to sound medical judgment. It will be understood by those of ordinary skill in the art however, that a patient may insist upon a lower dose or tolerable dose for medical reasons, psychological reasons or for virtually any other reasons.

A response to a therapeutically effective dose of a disclosed compound and/or pharmaceutical composition, for example, can be measured by determining the physiological effects of the treatment or medication, such as the decrease or lack of disease symptoms following administration of the treatment or pharmacological agent. Other assays will be known to one of ordinary skill in the art and can be employed for measuring the level of the response. The amount of a treatment may be varied for example by increasing or decreasing the amount of a disclosed compound and/or pharmaceutical composition, by changing the disclosed compound and/or pharmaceutical composition administered, by changing the route of administration, by changing the dosage timing and so on. Dosage can vary, and can be administered in one or more dose administrations daily, for one or several days. Guidance can be found in the literature for appropriate dosages for given classes of pharmaceutical products.

As used herein, the term "prophylactically effective amount" refers to an amount effective for preventing onset or initiation of a disease or condition.

As used herein, the term "prevent" or "preventing" refers to precluding, averting, obviating, forestalling, stopping, or hindering something from happening, especially by advance action. It is understood that where reduce, inhibit or prevent are used herein, unless specifically indicated otherwise, the use of the other two words is also expressly disclosed.

The term "pharmaceutically acceptable" describes a material that is not biologically or otherwise undesirable, i.e., without causing an unacceptable level of undesirable biological effects or interacting in a deleterious manner.

The term "pharmaceutically acceptable prodrug" or "prodrug" represents those prodrugs of the compounds of the present disclosure which are, within the scope of sound medical judgment, suitable for use in contact with the tissues of humans and lower animals without undue toxicity, irritation, allergic response, and the like, commensurate with a reasonable benefit/risk ratio, and effective for their intended use. Prodrugs of the present disclosure can be rapidly transformed in vivo to a parent compound having a structure of a disclosed compound, for example, by hydrolysis in blood. A thorough discussion is provided in T. Higuchi and V. Stella, Pro-drugs as Novel Delivery Systems, V. 14 of the A.C.S. Symposium Series, and in Edward B. Roche, ed., Bioreversible Carriers in Drug Design, American Pharmaceutical Association and Pergamon Press (1987).

As used herein, the term "derivative" refers to a compound having a structure derived from the structure of a parent compound (e.g., a compound disclosed herein) and whose structure is sufficiently similar to those disclosed herein and based upon that similarity, would be expected by one skilled in the art to exhibit the same or similar activities and utilities as the claimed compounds, or to induce, as a precursor, the same or similar activities and utilities as the claimed compounds. Exemplary derivatives include salts, esters, amides, salts of esters or amides, and N-oxides of a parent compound.

The term "contacting" as used herein refers to bringing a disclosed compound or pharmaceutical composition in proximity to a cell, a target protein, or other biological entity together in such a manner that the disclosed compound or pharmaceutical composition can affect the activity of the a cell, target protein, or other biological entity, either directly; i.e., by interacting with the cell, target protein, or other biological entity itself, or indirectly; i.e., by interacting with another molecule, co-factor, factor, or protein on which the activity of the cell, target protein, or other biological entity itself is dependent.

The term "stable," as used herein, refers to compounds that are not substantially altered when subjected to conditions to allow for their production, detection, and, in certain aspects, their recovery, purification, and use for one or more of the purposes disclosed herein.

The compounds described in the invention can be present as a solvate. In some cases, the solvent used to prepare the solvate is an aqueous solution, and the solvate is then often referred to as a hydrate. The compounds can be present as a hydrate, which can be obtained, for example, by crystallization from a solvent or from aqueous solution. In this connection, one, two, three or any arbitrary number of solvent or water molecules can combine with the compounds according to the invention to form solvates and hydrates. Unless stated to the contrary, the invention includes all such possible solvates.

The term "co-crystal" means a physical association of two or more molecules which owe their stability through non-covalent interaction. One or more components of this molecular complex provide a stable framework in the crystalline lattice. In certain instances, the guest molecules are incorporated in the crystalline lattice as anhydrates or solvates, see e.g. "Crystal Engineering of the Composition of Pharmaceutical Phases. Do Pharmaceutical Co-crystals Represent a New Path to Improved Medicines?" Almarasson, O., et al., The Royal Society of Chemistry, 1889-1896, 2004. Examples of co-crystals include p-toluenesulfonic acid and benzenesulfonic acid.

Certain materials, compounds, compositions, and components disclosed herein can be obtained commercially or readily synthesized using techniques generally known to those of skill in the art. For example, the starting materials and reagents used in preparing the disclosed compounds and compositions are either available from commercial suppliers such as Aldrich Chemical Co., (Milwaukee, Wis.), Acros Organics (Morris Plains, N.J.), Fisher Scientific (Pittsburgh, Pa.), or Sigma (St. Louis, Mo.) or are prepared by methods known to those skilled in the art following procedures set forth in references such as Fieser and Fieser's Reagents for Organic Synthesis, Volumes 1-17 (John Wiley and Sons, 1991); Rodd's Chemistry of Carbon Compounds, Volumes 1-5 and Supplementals (Elsevier Science Publishers, 1989); Organic Reactions. Volumes 1-40 (John Wiley and Sons, 1991); March's Advanced Organic Chemistry, (John Wiley and Sons, 4th Edition); and Larock's Comprehensive Organic Transformations (VCH Publishers Inc., 1989).

Unless otherwise expressly stated, it is in no way intended that any method set forth herein be construed as requiring that its steps be performed in a specific order. Accordingly, where a method claim does not actually recite an order to be followed by its steps or it is not otherwise specifically stated in the claims or descriptions that the steps are to be limited to a specific order, it is no way intended that an order be inferred, in any respect. This holds for any possible non-express basis for interpretation, including: matters of logic with respect to arrangement of steps or operational flow, plain meaning derived from grammatical organization or punctuation; and the number or type of aspects described in the specification.

Disclosed are the components to be used to prepare the compositions of the invention as well as the compositions themselves to be used within the methods disclosed herein. These and other materials are disclosed herein, and it is understood that when combinations, subsets, interactions, groups, etc. of these materials are disclosed that while specific reference of each various individual and collective combinations and permutation of these compounds cannot be explicitly disclosed, each is specifically contemplated and described herein. For example, if a particular compound is disclosed and discussed and a number of modifications that can be made to a number of molecules including the compounds are discussed, specifically contemplated is each and every combination and permutation of the compound and the modifications that are possible unless specifically indicated to the contrary. Thus, if a class of molecules A, B, and C are disclosed as well as a class of molecules D, E. and F and an example of a combination molecule, A-D is disclosed, then even if each is not individually recited each is individually and collectively contemplated meaning combinations, A-E, A-F, B-D, B-E, B—F, C-D, C-E, and C-F are considered disclosed. Likewise, any subset or combination of these is also disclosed. Thus, for example, the sub-group of A-E, B-F, and C-E would be considered disclosed. This concept applies to all aspects of this application including, but not limited to, steps in methods of making and using the compositions of the invention. Thus, if there are a variety of additional steps that can be performed it is understood that each of these additional steps can be performed with any specific aspect or combination of aspects of the methods of the invention.

It is understood that the compositions disclosed herein have certain functions. Disclosed herein are certain structural requirements for performing the disclosed functions, and it is understood that there are a variety of structures that can perform the same function that are related to the disclosed structures, and that these structures will typically achieve the same result.

As used herein, nomenclature for compounds, including organic compounds, can be given using common names, IUPAC, IUBMB, or CAS recommendations for nomenclature. When one or more stereochemical features are present, Cahn-Ingold-Prelog rules for stereochemistry can be employed to designate stereochemical priority, E/Z specification, and the like. One of skill in the art can readily ascertain the structure of a compound if given a name, either by systemic reduction of the compound structure using naming conventions, or by commercially available software, such as CHEMDRAW™ (Cambridgesoft Corporation, U.S.A.).

It is understood, that unless otherwise specified, temperatures referred to herein are based on atmospheric pressure (i.e., one atmosphere).

Described herein are lithium cholesterol compositions, including, but not limited to lithium cholesterol sulfate compositions, and pharmaceutical compositions that have therapeutic or clinical utility. Also described herein are methods of synthesizing the lithium cholesterol sulfate and compositions containing the LiCS. Also described herein are methods of administering the lithium cholesterol sulfate to a subject in need thereof. In some aspects, the subject can have a neurological disorder such as a neurodegenerative condition, a neurological developmental disorder, a neurological injury, and other conditions resulting from neurological disorders. Other compositions, compounds, methods, features, and advantages of the present disclosure will be or become apparent to one having ordinary skill in the art upon examination of the following drawings, detailed description, and examples. It is intended that all such additional compositions, compounds, methods, features, and advantages be included within this description, and be within the scope of the present disclosure.

Neurodegenerative Diseases and Lithium.

In accordance with the purpose(s) of the present disclosure, as embodied and broadly described herein, embodiments of the present disclosure, in some aspects, relate to pharmaceutical compositions including lithium cholesterol sulfate and compositions and methods for the treatment of neurodegenerative conditions, neurodevelopmental conditions, and other neurological conditions.

Alzheimer's disease (AD) is a progressive neurodegenerative disease with clinical manifestations of dementia, aphasia, loss of motor function, impairment of visual space skills, executive dysfunction, and personality and behavior change. AD is the main cause of dementia and one of the great health-care challenges of the 21st century, accounting for more than 50% of all clinically diagnosed dementia (1). People in the final stages of AD are bed bound and require constant care, ultimately leading to death. By 2050, a new case of AD is expected to occur every 33 s, causing nearly 1 million new AD cases per year. Approximately 13% of the population over the age of 65 years is estimated to have AD and the total number of cases is expected to increase over the coming decades. AD pathogenesis is complex, involving abnormal amyloid-β (Aβ) metabolism, tau hyperphosphorylation, oxidative stress, inflammation, reactive glial and microglial changes, and other pathological events (2, 3). AD not only causes severe distress for patients and caregivers, but also results in a large economic burden on society (4). Therefore, it is very important to treat or prevent this disease progression.

Autism spectrum disorder (ASD) is a neurodevelopmental disorder characterized by persistent difficulties in social communication and social interaction, coupled with restricted, repetitive patterns of behavior or interest (5). These children also present with symptoms of mood disorder, such as elevated moods/euphoria, mania, and paranoia, whether accompanied or not by irritability (6, 7). According to a recent report from the Centers for Disease Control and Prevention (CDC), around 20 per 1000 children aged 6-17 in the United States are diagnosed with ASD in 2011-2012 (8). The cause of autism appears to be primarily genetic, but recent studies also indicate the presence of a strong inflammatory state associated with ASD (9).

Indeed, neuroinflammation and neuroimmune abnormalities have now been established in ASD as key factors in its development and maintenance, with increased expression of IL-13, IL-6, IL-17 and TNF-α in the autistic brain. At the same time, hyperphosphorylation of Tau may also be involved in the pathogenesis of autism (10).

Lithium salts have been used in psychiatry to treat bipolar disorder for many years, and now they are still considered as a first-line therapy for both the acute and long-term treatment of bipolar disorder (11). Simultaneously, recent studies found that lithium salts also have neuroprotective effects that include preventing apoptosis and increasing neurotrophins and other cell-survival molecules (12). Furthermore, beneficial effects of lithium salts on neurogenesis, brain remodeling, angiogenesis, mesenchymal stem cells functioning, and inflammation have been revealed (13). In particular, recent studies have found that lithium can act as a potential therapeutic for AD (13). Studies have showed that patients who were given lithium would progress less over the course of AD compared with the placebo-group (12, 14).

Lithium may not only have beneficial effects on cognitive performance in subjects with AD dementia, but also may have positive treatment effects in ASD (7, 13). In the neonatal isolation animal model, treatment of Sprague-Dawley rats with lithium chloride (2 mmol/kg i.p./day) reversed autistic features, such as social interaction deficit, excessive repetitive self-grooming behavior, increased anxiety and depression (15). In addition, lithium therapy reversed clinical regression, stabilized behavioural symptoms and allowed patients to recover their pre-catatonia level of functioning, without significant side effects (16). At present, lithium carbonate is usually applied in clinic, but other lithium salts such as lithium citrate, lithium sulfate, lithium orotate and lithium chloride are also used as alternatives. However, lithium treatment has serious short- and long-term side effects in humans and requires frequent monitoring of blood chemistry and lithium plasma levels so as to avoid toxicity, discouraging patients from choosing these drugs. Hence, there is a demand for a safer and more effective lithium formulation to treat AD and ASD.

Figure 1A:
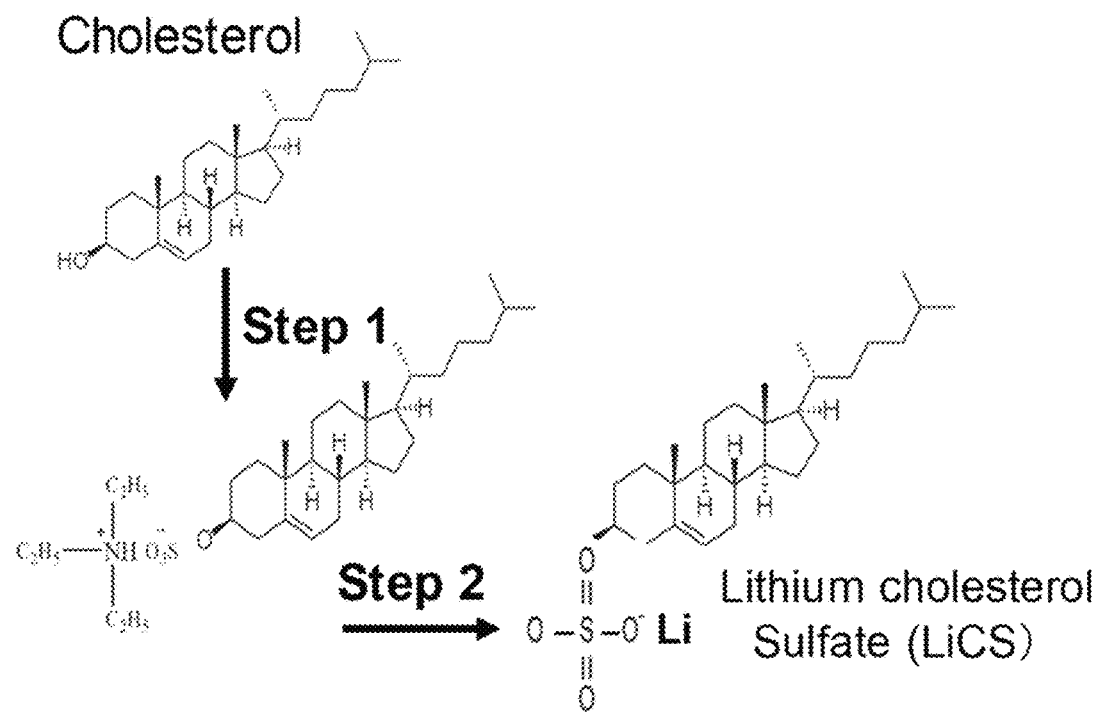
FIGS. 1A-1B illustrate the chemical structure and an embodiment of synthesis of lithium cholesterol sulfate (LiCS). LiCS was synthesized as described in Example 1 and illustrated in FIG. 1A, and its identification and purity was confirmed by HPLC-MS/MS (FIG. 1B)
Figure 1B:
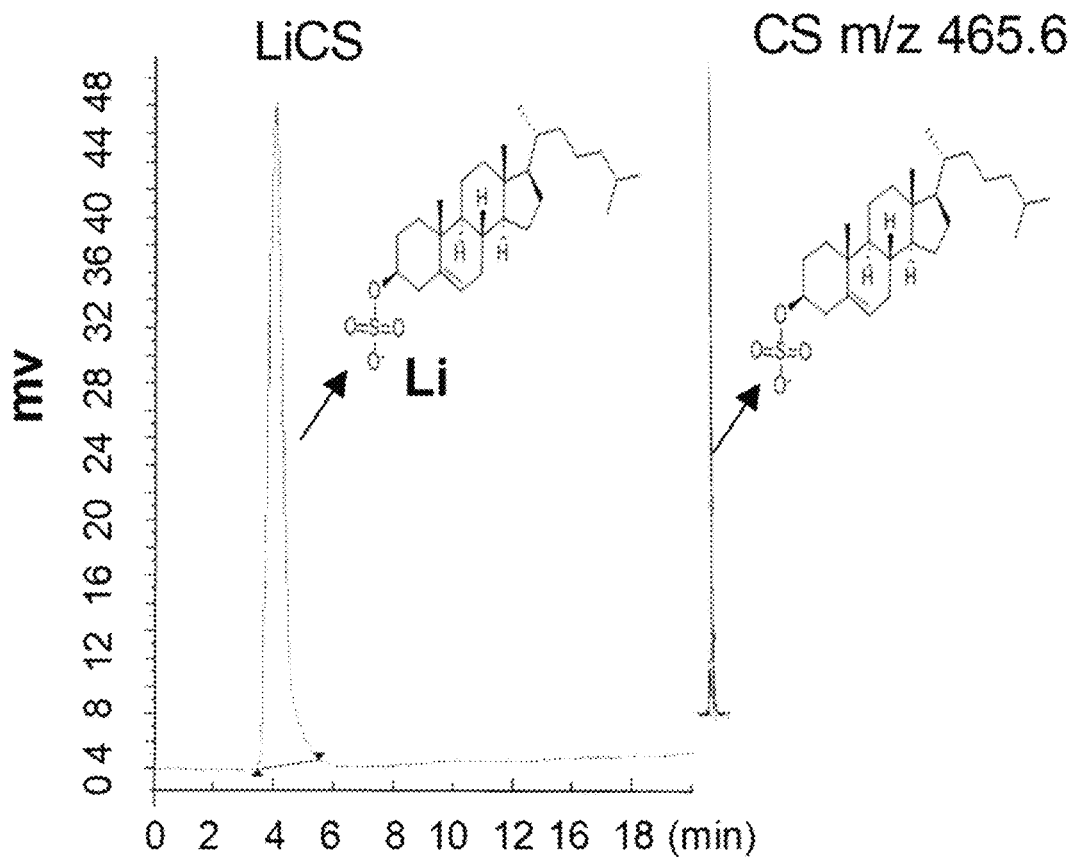

The present disclosure provides a novel lithium salt that is useful for treating AD, ASD, and other neurological conditions. The examples below describe tests and data illustrating the therapeutic potential of lithium cholesterol compositions, including, but not limited to lithium cholesterol sulfate compositions (UCS, FIG. 1). Cholesterol sulfate, is a normal constituent in a variety of human tissues (17, 18). This compound has a hydrophobic/hydrophilic property suited for interactions with membrane constituents and crossing the cell membrane and intestinal and blood-brain barriers (19). In addition, cholesterol sulfate itself can provide benefits in the treatment of AD and ASD, as well as other diseases potentially resulting from sulfur shortage, including eczema and asthma (20). Cholesterol has also been shown to directly bind APP and Aβ, making LiCS more effective in targeting Aβ aggregation (21). The present disclosure, including the following examples, illustrates that UCS will have a superior pharmacokinetic and safety profile compared with traditional lithium chemical forms for treatment of neurodegenerative diseases.

Compounds.

Compounds of the present disclosure pertain to lithium cholesterol compositions, including, but not limited to lithium cholesterol sulfate compositions (LiCS). In embodiments, the lithium cholesterol compositions of the disclosure have the following structure:

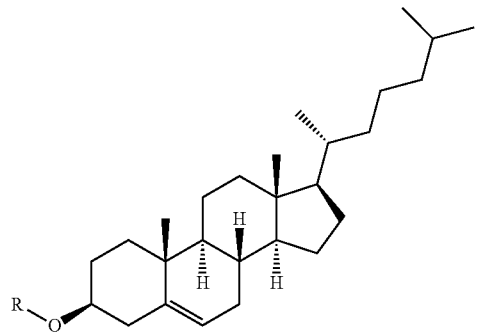

where R is selected from —$SO_3Li$, —$PO_3(Li)_2$, —$(CH_2)_n$(C=O)OLi, or —(C=O)($CH_2$)$_n$(C=O)OLi, where n is integer selected from 1, 2, 3, 4, 5, and 6.

In some aspects, the lithium cholesterol compositions of the disclosure can have a structure selected from:

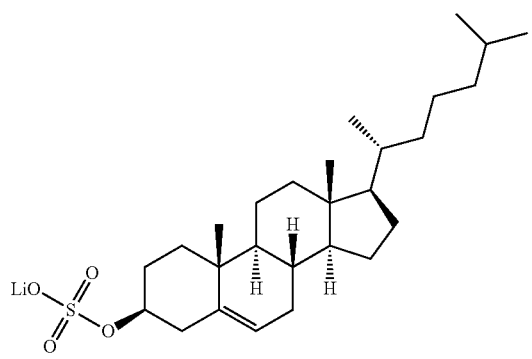

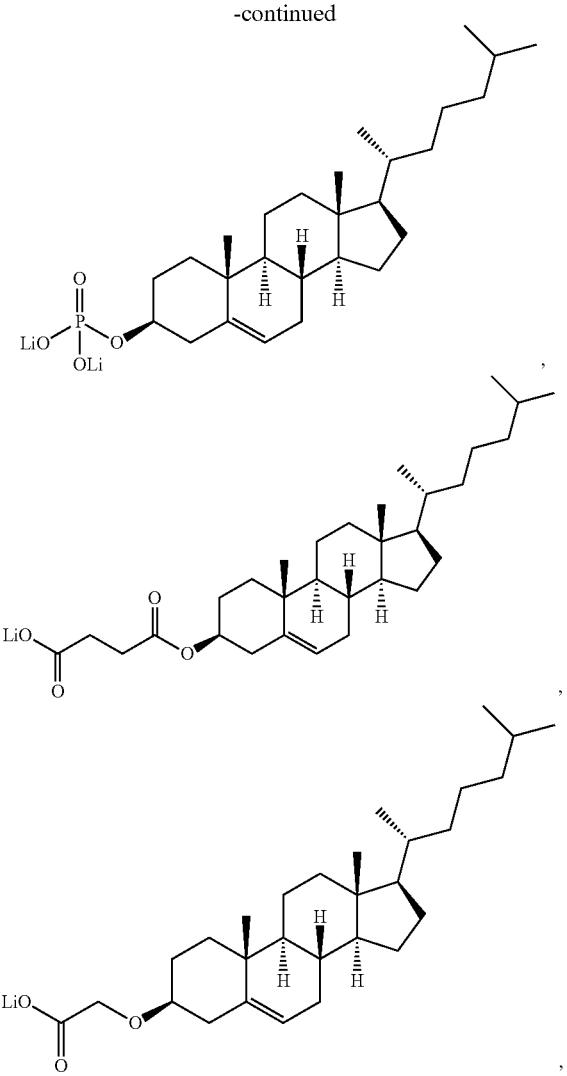

and combinations thereof.

In an aspect, the lithium cholesterol compositions of the disclosure can have the following structure:

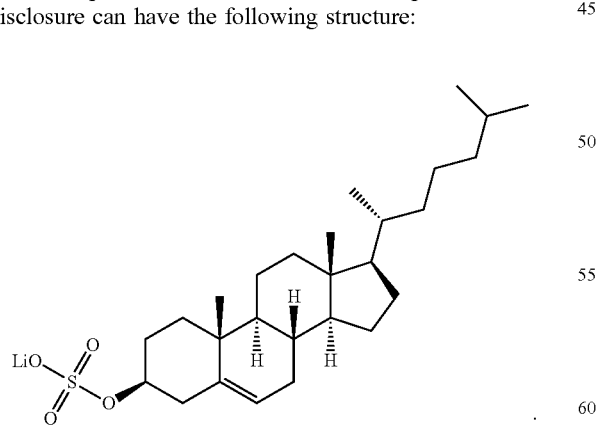

The foregoing compound can be referred to as either lithium cholesterol sulfate or UCS herein throughout. LiCS has a formula weight of 472.65.

In an aspect, the lithium cholesterol compositions of the disclosure can have the following structure:

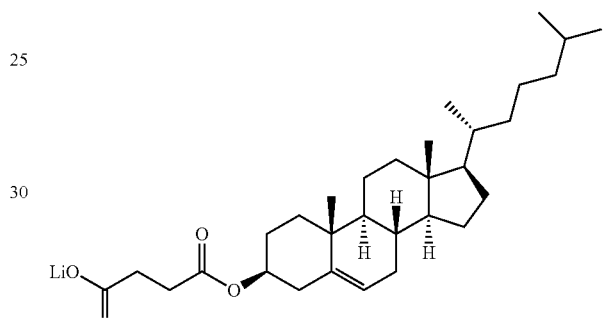

The foregoing compound can be referred to as either lithium cholesterol phosphate or LiCP herein throughout. LiCP has a formula weight of 478.51.

In an aspect, the lithium cholesterol compositions of the disclosure can have the following structure:

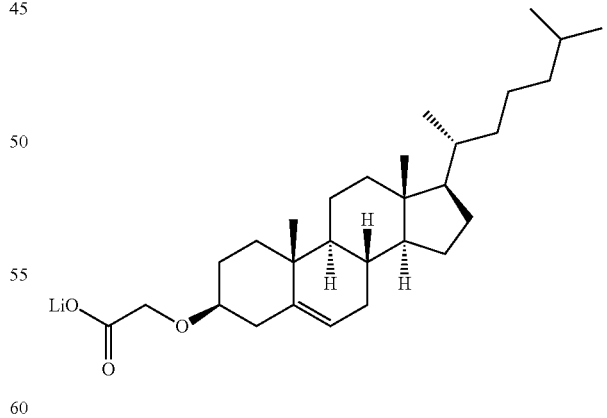

The foregoing compound can be referred to as either lithium cholesterol succinate, lithium cholesterol hemisuccinate or UCSc herein throughout. UCSc has a formula weight of 492.67.

In an aspect, the lithium cholesterol compositions of the disclosure can have the following structure:

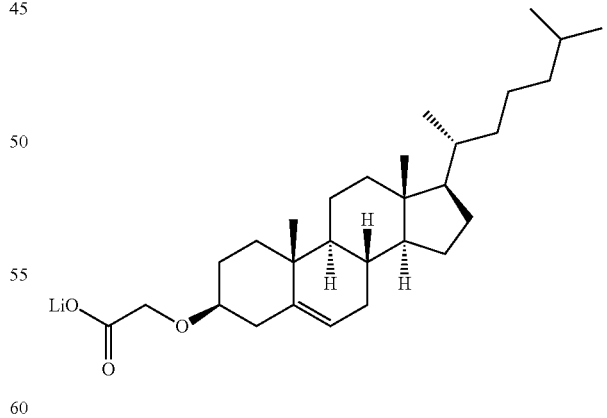

The foregoing compound can be referred to as either lithium cholesterol acetate or LiCAc herein throughout. LiCAc has a formula weight of 450.63.

Pharmaceutical Compositions.

In various aspects, the present disclosure relates to pharmaceutical compositions comprising a therapeutically effective amount of a lithium cholesterol sulfate compound of the present disclosure or a derivative thereof and a pharmaceutically acceptable carrier. As used herein, "pharmaceutically-acceptable carriers" means one or more of a pharmaceutically acceptable diluents, preservatives, antioxidants, solubilizers, emulsifiers, coloring agents, releasing agents, coating agents, sweetening, flavoring and perfuming agents, and adjuvants. The disclosed pharmaceutical compositions can be conveniently presented in unit dosage form and prepared by any of the methods well known in the art of pharmacy and pharmaceutical sciences.

In a further aspect, the disclosed pharmaceutical compositions comprise a therapeutically effective amount of at least one disclosed lithium cholesterol composition, including, but not limited to lithium cholesterol sulfate, at least one product of a disclosed method as an active ingredient, a pharmaceutically acceptable carrier, optionally one or more other therapeutic agent, and optionally one or more adjuvant. The disclosed pharmaceutical compositions include those suitable for oral, rectal, topical, pulmonary, nasal, and parenteral administration, although the most suitable route in any given case will depend on the particular host, and nature and severity of the conditions for which the active ingredient is being administered. In a further aspect, the disclosed pharmaceutical composition can be formulated to allow administration orally, nasally, via inhalation, parenterally, paracancerally, transmucosally, transdermally, intramuscularly, intravenously, intradermally, subcutaneously, intraperitonealy, intraventricularly, intracranially and intratumorally.

As used herein, "parenteral administration" includes administration by bolus injection or infusion, as well as administration by intravenous, intramuscular, intraarterial, intrathecal, intracapsular, intraorbital, intracardiac, intradermal, intraperitoneal, transtracheal, subcutaneous, subcuticular, intraarticular, subcapsular subarachnoid, intraspinal, epidural and intrasternal injection and infusion.

In various aspects, the present disclosure also relates to a pharmaceutical composition comprising a pharmaceutically acceptable carrier or diluent and, as active ingredient, a therapeutically effective amount of a disclosed lithium cholesterol composition, including, but not limited to lithium cholesterol sulfate, a product of a disclosed method of making, a pharmaceutically acceptable salt, a hydrate thereof, a solvate thereof, a polymorph thereof, or a stereochemically isomeric form thereof. In a further aspect, a disclosed compound, a product of a disclosed method of making, a pharmaceutically acceptable salt, a hydrate thereof, a solvate thereof, a polymorph thereof, or a stereochemically isomeric form thereof, or any subgroup or combination thereof may be formulated into various pharmaceutical forms for administration purposes.

In practice, the compounds of the present disclosure can be combined as the active ingredient in intimate admixture with a pharmaceutical carrier according to conventional pharmaceutical compounding techniques. The carrier can take a wide variety of forms depending on the form of preparation desired for administration, e.g., oral or parenteral (including intravenous). Thus, the pharmaceutical compositions of the present disclosure can be presented as discrete units suitable for oral administration such as capsules, cachets or tablets each containing a predetermined amount of the active ingredient. Further, the compositions can be presented as a powder, as granules, as a solution, as a suspension in an aqueous liquid, as a non-aqueous liquid, as an oil-in-water emulsion or as a water-in-oil liquid emulsion. In addition to the common dosage forms set out above, the compounds of the present disclosure, and/or pharmaceutically acceptable salt(s) thereof, can also be administered by controlled release means and/or delivery devices. The compositions can be prepared by any of the methods of pharmacy. In general, such methods include a step of bringing into association the active ingredient with the carrier that constitutes one or more necessary ingredients. In general, the compositions are prepared by uniformly and intimately admixing the active ingredient with liquid carriers or finely divided solid carriers or both. The product can then be conveniently shaped into the desired presentation.

It is especially advantageous to formulate the aforementioned pharmaceutical compositions in unit dosage form for ease of administration and uniformity of dosage. The term "unit dosage form," as used herein, refers to physically discrete units suitable as unitary dosages, each unit containing a predetermined quantity of active ingredient calculated to produce the desired therapeutic effect in association with the required pharmaceutical carrier. That is, a "unit dosage form" is taken to mean a single dose wherein all active and inactive ingredients are combined in a suitable system, such that the patient or person administering the drug to the patient can open a single container or package with the entire dose contained therein, and does not have to mix any components together from two or more containers or packages. Typical examples of unit dosage forms are tablets (including scored or coated tablets), capsules or pills for oral administration; single dose vials for injectable solutions or suspension; suppositories for rectal administration; powder packets; wafers; and segregated multiples thereof. This list of unit dosage forms is not intended to be limiting in any way, but merely to represent typical examples of unit dosage forms.

The pharmaceutical compositions disclosed herein comprise a compound of the present disclosure (or pharmaceutically acceptable salts or derivatives thereof) as an active ingredient, a pharmaceutically acceptable carrier, and optionally one or more additional therapeutic agents. In various aspects, the disclosed pharmaceutical compositions can include a pharmaceutically acceptable carrier and a disclosed lithium cholesterol composition, including, but not limited to lithium cholesterol sulfate. In a further aspect, a disclosed lithium cholesterol composition, including, but not limited to lithium cholesterol sulfate, can also be included in a pharmaceutical composition in combination with one or more other therapeutically active compounds. The instant compositions include compositions suitable for oral, rectal, topical, and parenteral (including subcutaneous, intramuscular, and intravenous) administration, although the most suitable route in any given case will depend on the particular host, and nature and severity of the conditions for which the active ingredient is being administered. The pharmaceutical compositions can be conveniently presented in unit dosage form and prepared by any of the methods well known in the art of pharmacy.

Techniques and compositions for making dosage forms useful for materials and methods described herein are described, for example, in the following references: Modern Pharmaceutics, Chapters 9 and 10 (Banker & Rhodes, Editors, 1979); Pharmaceutical Dosage Forms: Tablets (Lieberman et al., 1981); Ansel, Introduction to Pharmaceutical Dosage Forms 2nd Edition (1976); Remington's Pharmaceutical Sciences, 17th ed. (Mack Publishing Company, Easton, Pa., 1985); Advances in Pharmaceutical Sciences (David Ganderton, Trevor Jones, Eds., 1992); Advances in Pharmaceutical Sciences Vol 7. (David Ganderton, Trevor Jones, James McGinity, Eds., 1995); Aqueous Polymeric Coatings for Pharmaceutical Dosage Forms (Drugs and the Pharmaceutical Sciences, Series 36 (James McGinity, Ed., 1989); Pharmaceutical Particulate Carriers: Therapeutic Applications: Drugs and the Pharmaceutical Sciences, Vol 61 (Alain Rolland, Ed., 1993); Drug Delivery to the Gastrointestinal Tract (Ellis Horwood Books in the Biological Sciences. Series in Pharmaceutical Technology; J. G. Hardy, S. S. Davis, Clive G. Wilson, Eds.); Modern Pharmaceutics Drugs and the Pharmaceutical Sciences, Vol 40 (Gilbert S. Banker, Christopher T. Rhodes, Eds.).

The compounds described herein are typically to be administered in admixture with suitable pharmaceutical diluents, excipients, extenders, or carriers (termed herein as a pharmaceutically acceptable carrier, or a carrier) suitably selected with respect to the intended form of administration and as consistent with conventional pharmaceutical practices. The deliverable compound will be in a form suitable for oral, rectal, topical, intravenous injection or parenteral administration. Carriers include solids or liquids, and the type of carrier is chosen based on the type of administration being used. The compounds may be administered as a dosage that has a known quantity of the compound.

Because of the ease in administration, oral administration can be a preferred dosage form, and tablets and capsules represent the most advantageous oral dosage unit forms in which case solid pharmaceutical carriers are obviously employed. However, other dosage forms may be suitable depending upon clinical population (e.g., age and severity of clinical condition), solubility properties of the specific disclosed compound used, and the like. Accordingly, the disclosed compounds can be used in oral dosage forms such as pills, powders, granules, elixirs, tinctures, suspensions, syrups, and emulsions. In preparing the compositions for oral dosage form, any convenient pharmaceutical media can be employed. For example, water, glycols, oils, alcohols, flavoring agents, preservatives, coloring agents and the like can be used to form oral liquid preparations such as suspensions, elixirs and solutions; while carriers such as starches, sugars, microcrystalline cellulose, diluents, granulating agents, lubricants, binders, disintegrating agents, and the like can be used to form oral solid preparations such as powders, capsules and tablets. Because of their ease of administration, tablets and capsules are the preferred oral dosage units whereby solid pharmaceutical carriers are employed. Optionally, tablets can be coated by standard aqueous or nonaqueous techniques.

The disclosed pharmaceutical compositions in an oral dosage form can comprise one or more pharmaceutical excipient and/or additive. Non-limiting examples of suitable excipients and additives include gelatin, natural sugars such as raw sugar or lactose, lecithin, pectin, starches (for example corn starch or amylose), dextran, polyvinyl pyrrolidone, polyvinyl acetate, gum arabic, alginic acid, tylose, talcum, lycopodium, silica gel (for example colloidal), cellulose, cellulose derivatives (for example cellulose ethers in which the cellulose hydroxy groups are partially etherified with lower saturated aliphatic alcohols and/or lower saturated, aliphatic oxyalcohols, for example methyl oxypropyl cellulose, methyl cellulose, hydroxypropyl methyl cellulose, hydroxypropyl methyl cellulose phthalate), fatty acids as well as magnesium, calcium or aluminum salts of fatty acids with 12 to 22 carbon atoms, in particular saturated (for example stearates), emulsifiers, oils and fats, in particular vegetable (for example, peanut oil, castor oil, olive oil, sesame oil, cottonseed oil, corn oil, wheat germ oil, sunflower seed oil, cod liver oil, in each case also optionally hydrated); glycerol esters and polyglycerol esters of saturated fatty acids $C_{12}H_{24}O_2$ to $C_{18}H_{36}O_2$ and their mixtures, it being possible for the glycerol hydroxy groups to be totally or also only partly esterified (for example mono-, di- and triglycerides); pharmaceutically acceptable mono- or multivalent alcohols and polyglycols such as polyethylene glycol and derivatives thereof, esters of aliphatic saturated or unsaturated fatty acids (2 to 22 carbon atoms, in particular 10-18 carbon atoms) with monovalent aliphatic alcohols (1 to 20 carbon atoms) or multivalent alcohols such as glycols, glycerol, diethylene glycol, pentacrythritol, sorbitol, mannitol and the like, which may optionally also be etherified, esters of citric acid with primary alcohols, acetic acid, urea, benzyl benzoate, dioxolanes, glyceroformals, tetrahydrofurfuryl alcohol, polyglycol ethers with C1-C12-alcohols, dimethylacetamide, lactamides, lactates, ethylcarbonates, silicones (in particular medium-viscous polydimethyl siloxanes), calcium carbonate, sodium carbonate, calcium phosphate, sodium phosphate, magnesium carbonate and the like.

Other auxiliary substances useful in preparing an oral dosage form are those which cause disintegration (so-called disintegrants), such as: cross-linked polyvinyl pyrrolidone, sodium carboxymethyl starch, sodium carboxymethyl cellulose or microcrystalline cellulose. Conventional coating substances may also be used to produce the oral dosage form. Those that may for example be considered are: polymerizates as well as copolymerizates of acrylic acid and/or methacrylic acid and/or their esters; copolymerizates of acrylic and methacrylic acid esters with a lower ammonium group content (for example EudragitR RS), copolymerizates of acrylic and methacrylic acid esters and trimethyl ammonium methacrylate (for example EudragitR RL); polyvinyl acetate; fats, oils, waxes, fatty alcohols; hydroxypropyl methyl cellulose phthalate or acetate succinate; cellulose acetate phthalate, starch acetate phthalate as well as polyvinyl acetate phthalate, carboxy methyl cellulose; methyl cellulose phthalate, methyl cellulose succinate, -phthalate succinate as well as methyl cellulose phthalic acid half ester; zein; ethyl cellulose as well as ethyl cellulose succinate; shellac, gluten; ethylcarboxyethyl cellulose; ethacrylate-maleic acid anhydride copolymer; maleic acid anhydride-vinyl methyl ether copolymer; styrol-maleic acid copolymerizate; 2-ethyl-hexyl-acrylate maleic acid anhydride; crotonic acid-vinyl acetate copolymer; glutaminic acid/glutamic acid ester copolymer; carboxymethylethylcellulose glycerol monooctanoate; cellulose acetate succinate; polyarginine.

Plasticizing agents that may be considered as coating substances in the disclosed oral dosage forms are: citric and tartaric acid esters (acetyl-triethyl citrate, acetyl tributyl-, tributyl-, triethyl-citrate); glycerol and glycerol esters (glycerol diacetate, -triacetate, acetylated monoglycerides, castor oil); phthalic acid esters (dibutyl-, diamyl-, diethyl-, dimethyl-, dipropyl-phthalate), di-(2-methoxy- or 2-ethoxyethyl)-phthalate, ethylphthalyl glycolate, butylphthalylethyl glycolate and butylglycolate; alcohols (propylene glycol, polyethylene glycol of various chain lengths), adipates (diethyladipate, di-(2-methoxy- or 2-ethoxyethyl)-adipate; benzophenone; diethyl- and diburylsebacate, dibutylsuccinate, dibutyltartrate; diethylene glycol dipropionate; ethyleneglycol diacetate, -dibutyrate, -dipropionate; tributyl phosphate, tributyrin; polyethylene glycol sorbitan monooleate (polysorbates such as Polysorbar 50); sorbitan monooleate.

Moreover, suitable binders, lubricants, disintegrating agents, coloring agents, flavoring agents, flow-inducing agents, and melting agents may be included as carriers. The pharmaceutical carrier employed can be, for example, a solid, liquid, or gas. Examples of solid carriers include, but are not limited to, lactose, terra alba, sucrose, glucose, methylcellulose, dicalcium phosphate, calcium sulfate, mannitol, sorbitol talc, starch, gelatin, agar, pectin, acacia, magnesium stearate, and stearic acid. Examples of liquid carriers are sugar syrup, peanut oil, olive oil, and water. Examples of gaseous carriers include carbon dioxide and nitrogen.

In various aspects, a binder can include, for example, starch, gelatin, natural sugars such as glucose or beta-lactose, corn sweeteners, natural and synthetic gums such as acacia, tragacanth, or sodium alginate, carboxymethylcellulose, polyethylene glycol, waxes, and the like. Lubricants used in these dosage forms include sodium oleate, sodium stearate, magnesium stearate, sodium benzoate, sodium acetate, sodium chloride, and the like. In a further aspect, a disintegrator can include, for example, starch, methyl cellulose, agar, bentonite, xanthan gum, and the like.

In various aspects, an oral dosage form, such as a solid dosage form, can comprise a disclosed compound that is attached to polymers as targetable drug carriers or as a prodrug. Suitable biodegradable polymers useful in achieving controlled release of a drug include, for example, polylactic acid, polyglycolic acid, copolymers of polylactic and polyglycolic acid, caprolactones, polyhydroxy butyric acid, polyorthoesters, polyacetals, polydihydropyrans, polycyanoacylates, and hydrogels, preferably covalently cross-linked hydrogels.

Tablets may contain the active ingredient in admixture with non-toxic pharmaceutically acceptable excipients which are suitable for the manufacture of tablets. These excipients may be, for example, inert diluents, such as calcium carbonate, sodium carbonate, lactose, calcium phosphate or sodium phosphate; granulating and disintegrating agents, for example, corn starch, or alginic acid; binding agents, for example starch, gelatin or acacia, and lubricating agents, for example magnesium stearate, stearic acid or talc. The tablets may be uncoated or they may be coated by known techniques to delay disintegration and absorption in the gastrointestinal tract and thereby provide a sustained action over a longer period.

A tablet containing a disclosed compound can be prepared by compression or molding, optionally with one or more accessory ingredients or adjuvants. Compressed tablets can be prepared by compressing, in a suitable machine, the active ingredient in a free-flowing form such as powder or granules, optionally mixed with a binder, lubricant, inert diluent, surface active or dispersing agent. Molded tablets can be made by molding in a suitable machine, a mixture of the powdered compound moistened with an inert liquid diluent.

In various aspects, a solid oral dosage form, such as a tablet, can be coated with an enteric coating to prevent ready decomposition in the stomach. In various aspects, enteric coating agents include, but are not limited to, hydroxypropylmethylcellulose phthalate, methacrylic acid-methacrylic acid ester copolymer, polyvinyl acetate-phthalate and cellulose acetate phthalate. Akihiko Hasegawa "Application of solid dispersions of Nifedipine with enteric coating agent to prepare a sustained-release dosage form" Chem. Pharm. Bull. 33:1615-1619 (1985). Various enteric coating materials may be selected on the basis of testing to achieve an enteric coated dosage form designed ab initio to have a preferable combination of dissolution time, coating thicknesses and diametral crushing strength (e.g., see S. C. Porter et al. "The Properties of Enteric Tablet Coatings Made From Polyvinyl Acetate-phthalate and Cellulose acetate Phthalate", J. Pharm. Pharmacol. 22:42p (1970)). In a further aspect, the enteric coating may comprise hydroxypropylmethylcellulose phthalate, methacrylic acid-methacrylic acid ester copolymer, polyvinyl acetate-phthalate and cellulose acetate phthalate.

In various aspects, an oral dosage form can be a solid dispersion with a water soluble or a water insoluble carrier. Examples of water soluble or water insoluble carrier include, but are not limited to, polyethylene glycol, polyvinylpyrrolidone, hydroxypropylmethyl-cellulose, phosphatidylcholine, polyoxyethylene hydrogenated castor oil, hydroxypropylmethylcellulose phthalate, carboxymethylethylcellulose, or hydroxypropylmethylcellulose, ethyl cellulose, or stearic acid.

In various aspects, an oral dosage form can be in a liquid dosage form, including those that are ingested, or alternatively, administered as a mouth wash or gargle. For example, a liquid dosage form can include aqueous suspensions, which contain the active materials in admixture with excipients suitable for the manufacture of aqueous suspensions. In addition, oily suspensions may be formulated by suspending the active ingredient in a vegetable oil, for example *arachis* oil, olive oil, sesame oil or coconut oil, or in a mineral oil such as liquid paraffin. Oily suspensions may also contain various excipients. The pharmaceutical compositions of the present disclosure may also be in the form of oil-in-water emulsions, which may also contain excipients such as sweetening and flavoring agents.

For the preparation of solutions or suspensions it is, for example, possible to use water, particularly sterile water, or physiologically acceptable organic solvents, such as alcohols (ethanol, propanol, isopropanol, 1,2-propylene glycol, polyglycols and their derivatives, fatty alcohols, partial esters of glycerol), oils (for example peanut oil, olive oil, sesame oil, almond oil, sunflower oil, soya bean oil, castor oil, bovine hoof oil), paraffins, dimethyl sulphoxide, triglycerides and the like.

In the case of a liquid dosage form such as a drinkable solutions, the following substances may be used as stabilizers or solubilizers: lower aliphatic mono- and multivalent alcohols with 2-4 carbon atoms, such as ethanol, n-propanol, glycerol, polyethylene glycols with molecular weights between 200-600 (for example 1 to 40% aqueous solution), diethylene glycol monoethyl ether, 1,2-propylene glycol, organic amides, for example amides of aliphatic C1-C6-carboxylic acids with ammonia or primary, secondary or tertiary C1-C4-amines or C1-C4-hydroxy amines such as urea, urethane, acetamide, N-methyl acetamide, N,N-diethyl acetamide, N,N-dimethyl acetamide, lower aliphatic amines and diamines with 2-6 carbon atoms, such as ethylene diamine, hydroxyethyl theophylline, tromethamine (for example as 0.1 to 20% aqueous solution), aliphatic amino acids.

In preparing the disclosed liquid dosage form can comprise solubilizers and emulsifiers such as the following non-limiting examples can be used: polyvinyl pyrrolidone, sorbitan fatty acid esters such as sorbitan trioleate, phosphatides such as lecithin, acacia, tragacanth, polyoxyethylated sorbitan monooleate and other ethoxylated fatty acid esters of sorbitan, polyoxyethylated fats, polyoxyethylated oleotriglycerides, linolizated oleotriglycerides, polyethylene oxide condensation products of fatty alcohols, alkylphenols or fatty acids or also 1-methyl-3-(2-hydroxyethyl)imidazolidone-(2). In this context, polyoxyethylated means that the substances in question contain polyoxyethylene chains, the degree of polymerization of which generally lies between 2 and 40 and in particular between 10 and 20. Polyoxyethylated substances of this kind may for example be obtained by reaction of hydroxyl group-containing compounds (for example mono- or diglycerides or unsaturated compounds such as those containing oleic acid radicals) with ethylene oxide (for example 40 Mol ethylene oxide per 1 Mol glyceride). Examples of oleotriglycerides are olive oil, peanut oil, castor oil, sesame oil, cottonseed oil, corn oil. See also Dr. H. P. Fiedler "Lexikon der Hillsstoffe far Pharmazie, Kostnetik und angrenzende Gebiete" 1971, pages 191-195.

In various aspects, a liquid dosage form can further comprise preservatives, stabilizers, buffer substances, flavor correcting agents, sweeteners, colorants, antioxidants and complex formers and the like. Complex formers which may be for example be considered are: chelate formers such as ethylene diamine retrascetic acid, nitrilotriacetic acid, diethylene triamine pentacetic acid and their salts.

It may optionally be necessary to stabilize a liquid dosage form with physiologically acceptable bases or buffers to a pH range of approximately 6 to 9. Preference may be given to as neutral or weakly basic a pH value as possible (up to pH 8).

In order to enhance the solubility and/or the stability of a disclosed compound in a disclosed liquid dosage form, a parenteral injection form, or an intravenous injectable form, it can be advantageous to employ α-, β- or γ-cyclodextrins or their derivatives, in particular hydroxyalkyl substituted cyclodextrins, e.g. 2-hydroxypropyl-β-cyclodextrin or sulfobutyl-β-cyclodextrin. Also co-solvents such as alcohols may improve the solubility and/or the stability of the compounds according to the present disclosure in pharmaceutical compositions.

In various aspects, a disclosed liquid dosage form, a parenteral injection form, or an intravenous injectable form can further comprise liposome delivery systems, such as small unilamellar vesicles, large unilamellar vesicles, and multilamellar vesicles. Liposomes can be formed from a variety of phospholipids, such as cholesterol, stearylamine, or phosphatidylcholines.

Pharmaceutical compositions of the present disclosure suitable injection, such as parenteral administration, such as intravenous, intramuscular, or subcutaneous administration. Pharmaceutical compositions for injection can be prepared as solutions or suspensions of the active compounds in water. A suitable surfactant can be included such as, for example, hydroxypropylcellulose. Dispersions can also be prepared in glycerol, liquid polyethylene glycols, and mixtures thereof in oils. Further, a preservative can be included to prevent the detrimental growth of microorganisms.

Pharmaceutical compositions of the present disclosure suitable for parenteral administration can include sterile aqueous or oleaginous solutions, suspensions, or dispersions. Furthermore, the compositions can be in the form of sterile powders for the extemporaneous preparation of such sterile injectable solutions or dispersions. In some aspects, the final injectable form is sterile and must be effectively fluid for use in a syringe. The pharmaceutical compositions should be stable under the conditions of manufacture and storage; thus, preferably should be preserved against the contaminating action of microorganisms such as bacteria and fungi. The carrier can be a solvent or dispersion medium containing, for example, water, ethanol, polyol (e.g., glycerol, propylene glycol and liquid polyethylene glycol), vegetable oils, and suitable mixtures thereof.

Injectable solutions, for example, can be prepared in which the carrier comprises saline solution, glucose solution or a mixture of saline and glucose solution. Injectable suspensions may also be prepared in which case appropriate liquid carriers, suspending agents and the like may be employed. In some aspects, a disclosed parenteral formulation can comprise about 0.01-0.1 M, e.g. about 0.05 M, phosphate buffer. In a further aspect, a disclosed parenteral formulation can comprise about 0.9% saline.

In various aspects, a disclosed parenteral pharmaceutical composition can comprise pharmaceutically acceptable carriers such as aqueous or non-aqueous solutions, suspensions, and emulsions. Examples of non-aqueous solvents are propylene glycol, polyethylene glycol, vegetable oils such as olive oil, and injectable organic esters such as ethyl oleate. Aqueous carriers include but not limited to water, alcoholic/aqueous solutions, emulsions or suspensions, including saline and buffered media. Parenteral vehicles can include mannitol, normal serum albumin, sodium chloride solution, Ringer's dextrose, dextrose and sodium chloride, lactated Ringer's and fixed oils. Intravenous vehicles include fluid and nutrient replenishers, electrolyte replenishers such as those based on Ringer's dextrose, and the like. Preservatives and other additives may also be present, such as, for example, antimicrobials, antioxidants, collating agents, inert gases and the like. In a further aspect, a disclosed parenteral pharmaceutical composition can comprise may contain minor amounts of additives such as substances that enhance isotonicity and chemical stability, e.g., buffers and preservatives. Also contemplated for injectable pharmaceutical compositions are solid form preparations that are intended to be converted, shortly before use, to liquid form preparations. Furthermore, other adjuvants can be included to render the formulation isotonic with the blood of the subject or patient.

In addition to the pharmaceutical compositions described herein above, the disclosed compounds can also be formulated as a depot preparation. Such long acting formulations can be administered by implantation (e.g., subcutaneously or intramuscularly) or by intramuscular injection. Thus, for example, the compounds can be formulated with suitable polymeric or hydrophobic materials (e.g., as an emulsion in an acceptable oil) or ion exchange resins, or as sparingly soluble derivatives, e.g., as a sparingly soluble salt.

Pharmaceutical compositions of the present disclosure can be in a form suitable for topical administration. As used herein, the phrase "topical application" means administration onto a biological surface, whereby the biological surface includes, for example, a skin area (e.g., hands, forearms, elbows, legs, face, nails, anus and genital areas) or a mucosal membrane. By selecting the appropriate carrier and optionally other ingredients that can be included in the composition, as is detailed herein below, the compositions of the present invention may be formulated into any form typically employed for topical application. A topical pharmaceutical composition can be in a form of a cream, an ointment, a paste, a gel, a lotion, milk, a suspension, an aerosol, a spray, foam, a dusting powder, a pad, and a patch. Further, the compositions can be in a form suitable for use in transdermal devices. These formulations can be prepared, utilizing a compound of the present disclosure, or pharmaceutically acceptable salts thereof, via conventional processing methods. As an example, a cream or ointment is prepared by mixing hydrophilic material and water, together with about 5 wt % to about 10 wt % of the compound, to produce a cream or ointment having a desired consistency.

In the compositions suitable for percutaneous administration, the carrier optionally comprises a penetration enhancing agent and/or a suitable wetting agent, optionally combined with suitable additives of any nature in minor proportions, which additives do not introduce a significant deleterious effect on the skin. Said additives may facilitate the administration to the skin and/or may be helpful for preparing the desired compositions. These compositions may be administered in various ways, e.g., as a transdermal patch, as a spot-on, as an ointment.

Ointments are semisolid preparations, typically based on petrolatum or petroleum derivatives. The specific ointment base to be used is one that provides for optimum delivery for the active agent chosen for a given formulation, and, preferably, provides for other desired characteristics as well (e.g., emollience). As with other carriers or vehicles, an ointment base should be inert, stable, nonirritating and nonsensitizing. As explained in Remington: The Science and Practice of Pharmacy, 19th Ed., Easton, Pa.: Mack Publishing Co. (1995), pp. 1399-1404, ointment bases may be grouped in four classes: oleaginous bases; emulsifiable bases; emulsion bases; and water-soluble bases. Oleaginous ointment bases include, for example, vegetable oils, fats obtained from animals, and semisolid hydrocarbons obtained from petroleum. Emulsifiable ointment bases, also known as absorbent ointment bases, contain little or no water and include, for example, hydroxystearin sulfate, anhydrous lanolin and hydrophilic petrolatum. Emulsion ointment bases are either water-in-oil (W/O) emulsions or oil-in-water (O/W) emulsions, and include, for example, cetyl alcohol, glyceryl monostearate, lanolin and stearic acid. Preferred water-soluble ointment bases are prepared from polyethylene glycols of varying molecular weight Lotions are preparations that are to be applied to the skin surface without friction.

Lotions are typically liquid or semiliquid preparations in which solid particles, including the active agent, are present in a water or alcohol base. Lotions are typically preferred for treating large body areas, due to the ease of applying a more fluid composition. Lotions are typically suspensions of solids, and oftentimes comprise a liquid oily emulsion of the oil-in-water type. It is generally necessary that the insoluble matter in a lotion be finely divided. Lotions typically contain suspending agents to produce better dispersions as well as compounds useful for localizing and holding the active agent in contact with the skin, such as methylcellulose, sodium carboxymethyl-cellulose, and the like.

Creams are viscous liquids or semisolid emulsions, either oil-in-water or water-in-oil. Cream bases are typically water-washable, and contain an oil phase, an emulsifier and an aqueous phase. The oil phase, also called the "internal" phase, is generally comprised of petrolatum and/or a fatty alcohol such as cetyl or stearyl alcohol. The aqueous phase typically, although not necessarily, exceeds the oil phase in volume, and generally contains a humectant. The emulsifier in a cream formulation is generally a nonionic, anionic, cationic or amphoteric surfactant. Reference may be made to Remington: The Science and Practice of Pharmacy, supra, for further information.

Pastes are semisolid dosage forms in which the bioactive agent is suspended in a suitable base. Depending on the nature of the base, pastes are divided between fatty pastes or those made from a single-phase aqueous gel. The base in a fatty paste is generally petrolatum, hydrophilic petrolatum and the like. The pastes made from single-phase aqueous gels generally incorporate carboxymethylcellulose or the like as a base. Additional reference may be made to Remington: The Science and Practice of Pharmacy, for further information.

Gel formulations are semisolid, suspension-type systems. Single-phase gels contain organic macromolecules distributed substantially uniformly throughout the carrier liquid, which is typically aqueous, but also, preferably, contain an alcohol and, optionally, an oil. Preferred organic macromolecules, i.e., gelling agents, are crosslinked acrylic acid polymers such as the family of carbomer polymers, e.g., carboxypolyalkylenes that may be obtained commercially under the trademark Carbopol™. Other types of preferred polymers in this context are hydrophilic polymers such as polyethylene oxides, polyoxyethylene-polyoxypropylene copolymers and polyvinylalcohol; modified cellulose, such as hydroxypropyl cellulose, hydroxyethyl cellulose, hydroxypropyl methylcellulose, hydroxypropyl methylcellulose phthalate, and methyl cellulose; gums such as tragacanth and xanthan gum; sodium alginate; and gelatin. In order to prepare a uniform gel, dispersing agents such as alcohol or glycerin can be added, or the gelling agent can be dispersed by trituration, mechanical mixing or stirring, or combinations thereof.

Sprays generally provide the active agent in an aqueous and/or alcoholic solution which can be misted onto the skin for delivery. Such sprays include those formulated to provide for concentration of the active agent solution at the site of administration following delivery, e.g., the spray solution can be primarily composed of alcohol or other like volatile liquid in which the active agent can be dissolved. Upon delivery to the skin, the carrier evaporates, leaving concentrated active agent at the site of administration.

Foam compositions are typically formulated in a single or multiple phase liquid form and housed in a suitable container, optionally together with a propellant which facilitates the expulsion of the composition from the container, thus transforming it into a foam upon application. Other foam forming techniques include, for example the "Bag-in-a-can" formulation technique. Compositions thus formulated typically contain a low-boiling hydrocarbon, e.g., isopropane. Application and agitation of such a composition at the body temperature cause the isopropane to vaporize and generate the foam, in a manner similar to a pressurized aerosol foaming system. Foams can be water-based or aqueous alkanolic, but are typically formulated with high alcohol content which, upon application to the skin of a user, quickly evaporates, driving the active ingredient through the upper skin layers to the site of treatment.

Skin patches typically comprise a backing, to which a reservoir containing the active agent is attached. The reservoir can be, for example, a pad in which the active agent or composition is dispersed or soaked, or a liquid reservoir. Patches typically further include a frontal water permeable adhesive, which adheres and secures the device to the treated region. Silicone rubbers with self-adhesiveness can alternatively be used. In both cases, a protective permeable layer can be used to protect the adhesive side of the patch prior to its use. Skin patches may further comprise a removable cover, which serves for protecting it upon storage.

Examples of patch configuration which can be utilized with the present invention include a single-layer or multi-layer drug-in-adhesive systems which are characterized by the inclusion of the drug directly within the skin-contacting adhesive. In such a transdermal patch design, the adhesive not only serves to affix the patch to the skin, but also serves as the formulation foundation, containing the drug and all the excipients under a single backing film. In the multi-layer drug-in-adhesive patch a membrane is disposed between two distinct drug-in-adhesive layers or multiple drug-in-adhesive layers are incorporated under a single backing film.

Examples of pharmaceutically acceptable carriers that are suitable for pharmaceutical compositions for topical applications include carrier materials that are well-known for use in the cosmetic and medical arts as bases for e.g., emulsions, creams, aqueous solutions, oils, ointments, pastes, gels, lotions, milks, foams, suspensions, aerosols and the like, depending on the final form of the composition. Representative examples of suitable carriers according to the present invention therefore include, without limitation, water, liquid alcohols, liquid glycols, liquid polyalkylene glycols, liquid esters, liquid amides, liquid protein hydrolysates, liquid alkylated protein hydrolysates, liquid lanolin and lanolin derivatives, and like materials commonly employed in cosmetic and medicinal compositions. Other suitable carriers according to the present invention include, without limitation, alcohols, such as, for example, monohydric and polyhydric alcohols, e.g., ethanol, isopropanol, glycerol, sorbitol, 2-methoxyethanol, diethyleneglycol, ethylene glycol, hexyleneglycol, mannitol, and propylene glycol; ethers such as diethyl or dipropyl ether; polyethylene glycols and methoxypolyoxyethylenes (carbowaxes having molecular weight ranging from 200 to 20,000); polyoxyethylene glycerols, polyoxyethylene sorbitols, stearoyl diacetin, and the like.

Topical compositions of the present disclosure can, if desired, be presented in a pack or dispenser device, such as an FDA-approved kit, which may contain one or more unit dosage forms containing the active ingredient. The dispenser device may, for example, comprise a tube. The pack or dispenser device may be accompanied by instructions for administration. The pack or dispenser device may also be accompanied by a notice in a form prescribed by a governmental agency regulating the manufacture, use, or sale of pharmaceuticals, which notice is reflective of approval by the agency of the form of the compositions for human or veterinary administration. Such notice, for example, may include labeling approved by the U.S. Food and Drug Administration for prescription drugs or of an approved product insert. Compositions comprising the topical composition of the invention formulated in a pharmaceutically acceptable carrier may also be prepared, placed in an appropriate container, and labeled for treatment of an indicated condition.

Another patch system configuration which can be used by the present invention is a reservoir transdermal system design which is characterized by the inclusion of a liquid compartment containing a drug solution or suspension separated from the release liner by a semi-permeable membrane and adhesive. The adhesive component of this patch system can either be incorporated as a continuous layer between the membrane and the release liner or in a concentric configuration around the membrane. Yet another patch system configuration which can be utilized by the present invention is a matrix system design which is characterized by the inclusion of a semisolid matrix containing a drug solution or suspension which is in direct contact with the release liner. The component responsible for skin adhesion is incorporated in an overlay and forms a concentric configuration around the semisolid matrix.

Pharmaceutical compositions of the present disclosure can be in a form suitable for rectal administration wherein the carrier is a solid. It is preferable that the mixture forms unit dose suppositories. Suitable carriers include cocoa butter and other materials commonly used in the art. The suppositories can be conveniently formed by first admixing the composition with the softened or melted carrier(s) followed by chilling and shaping in molds.

Pharmaceutical compositions containing a compound of the present disclosure, and/or pharmaceutically acceptable salts thereof, can also be prepared in powder or liquid concentrate form.

The pharmaceutical composition (or formulation) may be packaged in a variety of ways. Generally, an article for distribution includes a container that contains the pharmaceutical composition in an appropriate form. Suitable containers are well known to those skilled in the art and include materials such as bottles (plastic and glass), sachets, foil blister packs, and the like. The container may also include a tamper proof assemblage to prevent indiscreet access to the contents of the package. In addition, the container typically has deposited thereon a label that describes the contents of the container and any appropriate warnings or instructions.

The disclosed pharmaceutical compositions may, if desired, be presented in a pack or dispenser device which may contain one or more unit dosage forms containing the active ingredient. The pack may for example comprise metal or plastic foil, such as a blister pack. The pack or dispenser device may be accompanied by instructions for administration. The pack or dispenser may also be accompanied with a notice associated with the container in form prescribed by a governmental agency regulating the manufacture, use, or sale of pharmaceuticals, which notice is reflective of approval by the agency of the form of the drug for human or veterinary administration. Such notice, for example, may be the labeling approved by the U.S. Food and Drug Administration for prescription drugs, or the approved product insert. Pharmaceutical compositions comprising a disclosed compound formulated in a compatible pharmaceutical carrier may also be prepared, placed in an appropriate container, and labeled for treatment of an indicated condition.

The exact dosage and frequency of administration depends on the particular disclosed lithium cholesterol composition, including, but not limited to lithium cholesterol sulfate, or derivative thereof; the particular condition being treated and the severity of the condition being treated; various factors specific to the medical history of the subject to whom the dosage is administered such as the age, weight, sex, extent of disorder and general physical condition of the particular subject, as well as other medication the individual may be taking; as is well known to those skilled in the art. Furthermore, it is evident that said effective daily amount may be lowered or increased depending on the response of the treated subject and/or depending on the evaluation of the physician prescribing the compounds of the present disclosure.

Depending on the mode of administration, the pharmaceutical composition will comprise from 0.05 to 99% by weight, preferably from 0.1 to 70% by weight, more preferably from 0.1 to 50% by weight of the active ingredient, and, from 1 to 99.95% by weight, preferably from 30 to 99.9% by weight, more preferably from 50 to 99.9% by weight of a pharmaceutically acceptable carrier, all percentages being based on the total weight of the composition.

For therapeutic treatments of the present disclosure, with lithium cholesterol composition, including, but not limited to lithium cholesterol sulfate, as active ingredient, in general, an appropriate dosage level will generally be about 0.01 to 1000 mg per kg patient body weight per day and can be administered in single or multiple doses. In various aspects, the dosage level will be about 0.1 to about 500 mg/kg per day, about 0.1 to 250 mg/kg per day, or about 0.5 to 100 mg/kg per day. A suitable dosage level can be about 0.01 to 1000 mg/kg per day, about 0.01 to 500 mg/kg per day, about 0.01 to 250 mg/kg per day, about 0.05 to 100 mg/kg per day, or about 0.1 to 50 mg/kg per day. Within this range the dosage can be 0.05 to 0.5, 0.5 to 5.0 or 5.0 to 50 mg/kg per day. For oral administration, the compositions are preferably provided in the form of tablets containing 1.0 to 1000 mg of the active ingredient, particularly 1.0, 5.0, 10, 15, 20, 25, 50, 75, 100, 150, 200, 250, 300, 400, 500, 600, 750, 800, 900 and 1000 mg of the active ingredient for the symptomatic adjustment of the dosage of the patient to be treated. The compound can be administered on a regimen of 1 to 4 times per day, preferably once or twice per day. This dosing regimen can be adjusted to provide the optimal therapeutic response.

Such unit doses as described hereinabove and hereinafter can be administered more than once a day, for example, 2, 3, 4, 5 or 6 times a day. In various aspects, such unit doses can be administered 1 or 2 times per day, so that the total dosage for a 70 kg adult is in the range of 0.001 to about 500 mg per kg weight of subject per administration. In a further aspect, dosage is 0.001 to about 300 mg per kg weight of subject per administration, and such therapy can extend for a number of weeks or months, and in some cases, years. It will be understood, however, that the specific dose level for any particular patient will depend on a variety of factors including the activity of the specific compound employed; the age, body weight, general health, sex and diet of the individual being treated; the time and route of administration; the rate of excretion; other drugs that have previously been administered; and the severity of the particular disease undergoing therapy, as is well understood by those of skill in the area.

A typical dosage can be one 1 mg to about 1000 mg tablet or 1 mg to about 300 mg taken once a day, or, multiple times per day, or one time-release capsule or tablet taken once a day and containing a proportionally higher content of active ingredient. The time-release effect can be obtained by capsule materials that dissolve at different pH values, by capsules that release slowly by osmotic pressure, or by any other known means of controlled release.

It can be necessary to use dosages outside these ranges in some cases as will be apparent to those skilled in the art. Further, it is noted that the clinician or treating physician will know how and when to start, interrupt, adjust, or terminate therapy in conjunction with individual patient response.

The present disclosure is further directed to a method for the manufacture of a medicament comprising an effective amount of lithium cholesterol sulfate for treating a neurological disorder (e.g., treatment of one or more neurological disorders such as neurodegenerative conditions and/or neurodevelopmental disorders, and other disorders, such as bipolar disorder or conditions caused by brain injury) in mammals (e.g., humans) comprising combining one or more disclosed lithium cholesterol compositions, including, but not limited to lithium cholesterol sulfate, products, or compositions with a pharmaceutically acceptable carrier or diluent. Thus, in one aspect, the present disclosure further relates to a method for manufacturing a medicament comprising combining at least one disclosed lithium cholesterol composition, including, but not limited to lithium cholesterol sulfate, or at least one disclosed product with a pharmaceutically acceptable carrier or diluent.

The disclosed pharmaceutical compositions can further comprise other therapeutically active compounds, which are usually applied in the treatment of the above mentioned pathological or clinical conditions.

It is understood that the disclosed compositions can be prepared from the disclosed compounds. It is also understood that the disclosed compositions can be employed in the disclosed methods of using.

As already mentioned, the present disclosure relates to a pharmaceutical composition comprising a therapeutically effective amount of a disclosed lithium cholesterol composition, including, but not limited to lithium cholesterol sulfate, a product of a disclosed method of making, and a pharmaceutically acceptable carrier. Additionally, the present disclosure relates to a process for preparing such a pharmaceutical composition, characterized in that a pharmaceutically acceptable carrier is intimately mixed with a therapeutically effective amount of a disclosed lithium cholesterol composition, including, but not limited to lithium cholesterol sulfat, according to the present disclosure.

As already mentioned, the present disclosure also relates to a pharmaceutical composition comprising a disclosed lithium cholesterol composition, including, but not limited to lithium cholesterol sulfate, a product of a disclosed method of making, or a pharmaceutically acceptable derivative thereof, and one or more other drugs in the treatment, prevention, control, amelioration, or reduction of risk of diseases or conditions for a disclosed compound or the other drugs may have utility as well as to the use of such a composition for the manufacture of a medicament. The present disclosure also relates to a combination of disclosed lithium cholesterol composition, including, but not limited to lithium cholesterol sulfate, a product of a disclosed method of making, a pharmaceutically acceptable derivative thereof, a polymorph thereof, and an additional therapeutic agent, as a combined preparation for simultaneous, separate or sequential use in the treatment or prevention of a condition in a mammal, including a human, the treatment or prevention of which is affected or facilitated by the modulatory effect of the disclosed compound and the additional therapeutic agent. The different drugs of such a combination or product may be combined in a single preparation together with pharmaceutically acceptable carriers or diluents, or they may each be present in a separate preparation together with pharmaceutically acceptable carriers or diluents.

In certain embodiments, the present disclosure provides compounds and/or pharmaceutical compositions comprising lithium cholesterol sulfate for use as a medicament.

This disclosure also provides compounds and pharmaceutical compositions comprising lithium cholesterol sulfate for use in the treatment of a neurological disorder. As discussed below, in embodiments, the neurological disorder is selected from the group consisting of: Alzheimer's disease, Autism spectrum disorder (ASD), bipolar disorder, traumatic brain injury, radiation induced brain injury and other neuropsychiatric disorders inducing, but not limited to amyotrophic laterals sclerosis (ALS), Parkinson's disease (PD), depressive disorder, suicidality, schizoaffective disorder, tic disorder (e.g., Tourette's syndrome), etc.

Methods of Making the Compounds.

In one aspect, the disclosure relates to methods of making compounds useful for the treatment for neurodegenerative conditions (such as Alzheimer's disease (AD), Parkinson's disease (PD), amyotrophic laterals sclerosis (ALS), and the like), neurodevelopmental disorders (such as Autism spectrum disorders, and the like), traumatic brain injury and acute brain injury (such as caused by ischemic stroke, head trauma, and the like), radiation induced brain injury, mood disorders (such as suicidal ideation, bipolar disorder, depressive disorder), and other neuropsychiatric disorders, including but not limited to schizoaffective disorder, tic disorder (e.g., Tourette's syndrome), and the like. In one aspect, the disclosure relates to the disclosed synthetic manipulations. In a further aspect, the disclosed compositions, such as lithium cholesterol compositions, including, but not limited to lithium cholesterol sulfate compositions (LiCS), comprise the products of the synthetic methods described herein.

The compounds of this disclosure can be prepared by employing reactions as shown in the disclosed schemes, in addition to other standard manipulations that are known in the literature, exemplified in the experimental sections or clear to one skilled in the art. For clarity, examples having a fewer substituent can be shown where multiple substituents are allowed under the definitions disclosed herein. Thus, the following examples are provided so that the disclosure might be more fully understood, are illustrative only, and should not be construed as limiting.

It is contemplated that each disclosed method can further comprise additional steps, manipulations, and/or components. It is also contemplated that any one or more step, manipulation, and/or component can be optionally omitted from the disclosure. It is understood that a disclosed method can be used to provide the disclosed compounds. It is also understood that the products of the disclosed methods can be employed in the disclosed compositions, kits, and uses.

In one aspect, the disclosed lithium cholesterol compositions, included, but not limited to compositions comprising a lithium cholesterol sulfate compound. In one aspect, a lithium cholesterol sulfate compound of the present disclosure can be prepared under mild conditions by a dicyclohexylcarbodiimide-mediated sulfation reaction of a hydroxyl moiety as shown immediately below. This type of reaction can be carried out as described in various methods, including, but not limited to, those described by R. O. Mumma (Lipids (1966) 1: 221) and R. O. Mumma, et al. (Steroids (1969) 14(1):67-74), and the reaction conditions set forth in this exemplary method can be suitably modified by the skilled artisan with regard to reaction amounts and ratios, temperature, time, and specific methods of purification. It should be noted that in the various following reaction schemes, the preparation of a lithium salt in the last step is shown utilizing ULiOH, under conditions as generally described in the indicated reference or alternatively, as described S. Natelson, et al. (J. Biol. Chem. 1934, 105:761-765). However, other suitable bases can be used such as lithium carbonate.

Alternatively, a method of obtaining the disclosed lithium cholesterol sulfate compounds can utilize chlorosulfuric acid comprising a suitable protecting group (indicated as "PG" in the reaction scheme shown below) on the acid group, e.g., an alkyl protecting group such as isobutyl. Suitable methods such as these are described by L. S. Simpson and T. S. Widlanski (JACS (2006) 128(5):1605-1610), and the reaction conditions set forth in this exemplary method can be suitably modified by the skilled artisan with regard to reaction amounts and ratios, temperature, time, and specific methods of purification. The overall reaction is shown below.

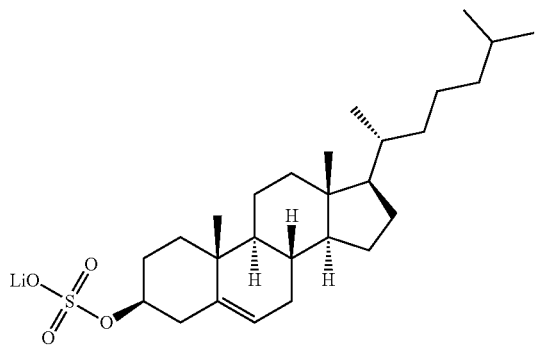

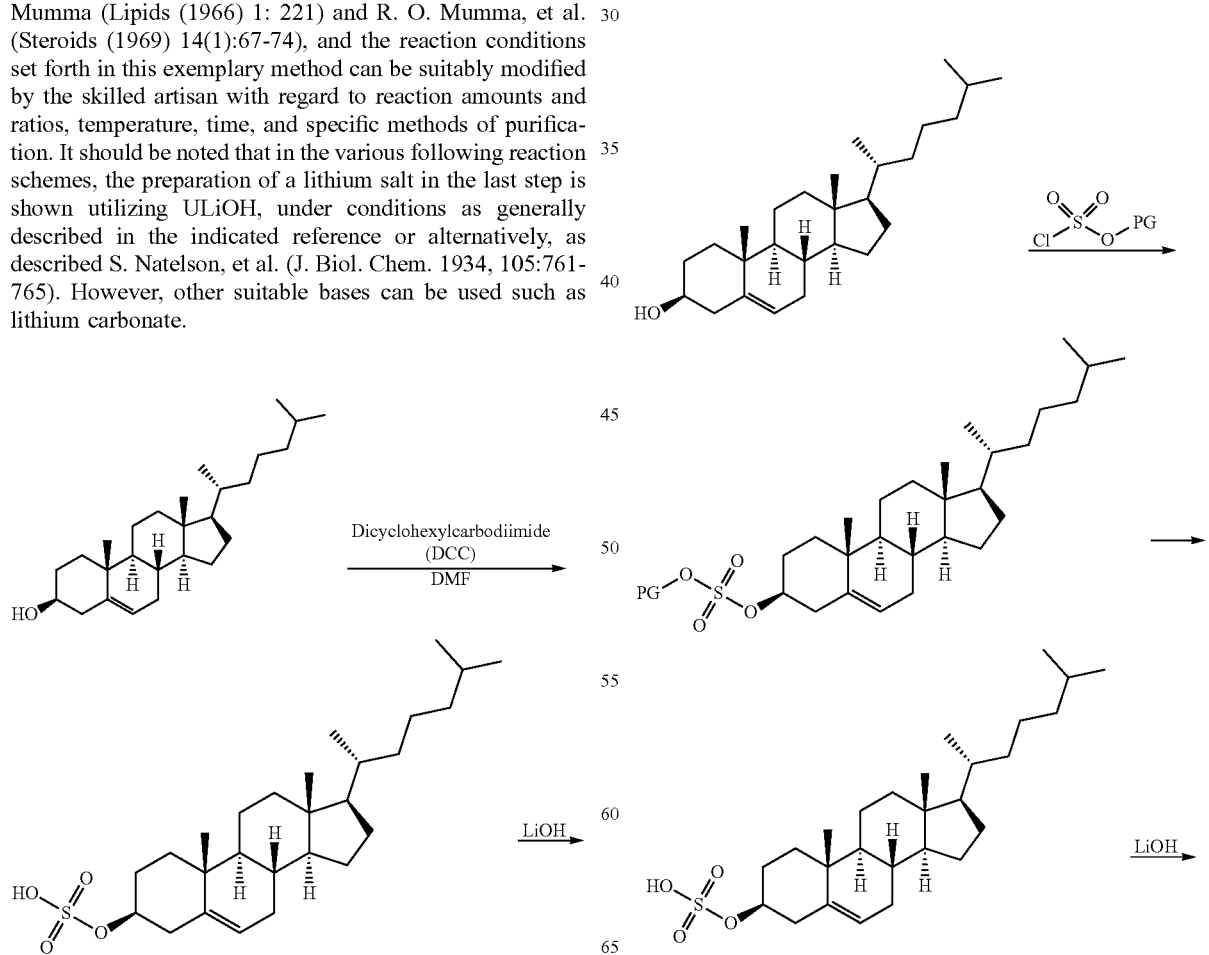

-continued

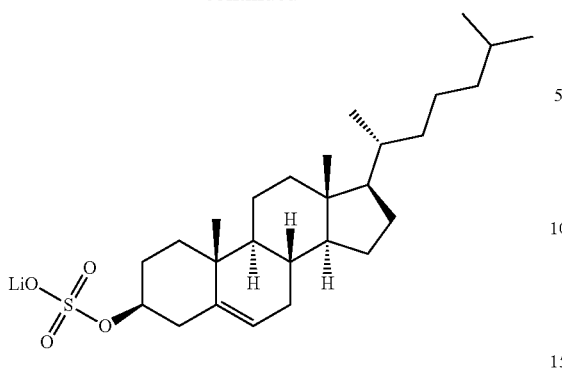

A further alternative sulfation method is as described by H. Noda, et al. (J. Clin. Biochem. Nutr. (1991) 10:83-91) involving reaction of excess cholesterol with sulfur trioxide-pyridine complex, followed by isolation using LiOH instead of NaOH. Preparation of lithium cholesterol sulfate from a sodium saltcan also be generally carried out as described by S. Natelson, et al. (J. Biol. Chem. 1934, 105:761-765).

Cholesterol sulfate is commercially available as the sodium salt, and this can be converted to the lithium salt by a variety of methods, including those described by S. Natelson, et al. (J. Biol. Chem. 1934, 105:761-765). Alternatively, commercially available sodium cholesterol sulfate can be dissolved in methanol with a molar equivalent of lithium chloride and heated, followed by differential precipitation and filtration to first remove sodium chloride, then with further cooling and addition of water, pure lithium cholesterol sulfate can be crystallized and obtained by filtration.

In one aspect, a lithium cholesterol oxoalkanoate compounds, i.e., wherein R is —(C=O)(CH$_2$)$_n$(C=O)OLi), where n is an integer having a value of 1, 2, 3, 4, 5, or 6, of the present disclosure can be prepared by reaction of cholesterol with a suitable cyclic dicarboxylic anhydride essentially as described by Y. Nie (Theranostics 2012; 2(11): 1092-1103), and the reaction conditions set forth in this exemplary method can be suitably modified by the skilled artisan with regard to reaction amounts and ratios, temperature, time, and specific methods of purification. A generalized reaction approach is shown immediately below. In the following reaction scheme, as an example, when n=4, the cyclic dicarboxylic anhydride used would be succinic anhydride.

-continued

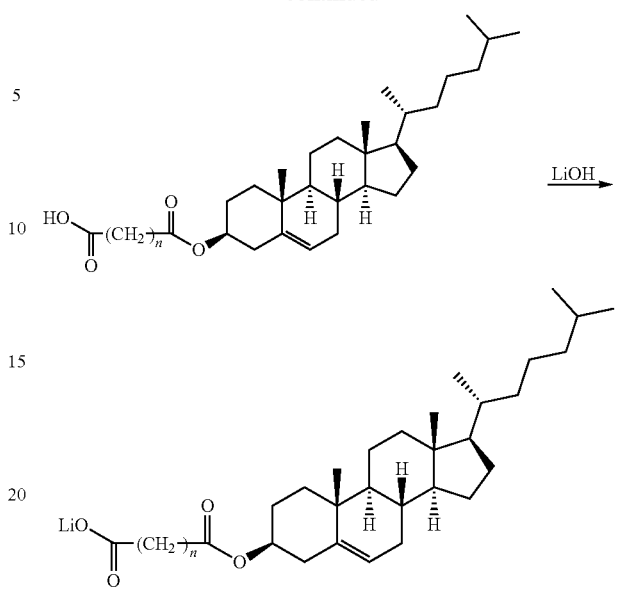

In one aspect, a lithium cholesterol phosphate compounds of the present disclosure can be prepared by reaction of cholesterol with a suitable cyclic dicarboxylic anhydride essentially as described by S. C. Davis and F. C. Szoka, Jr. (Bioconj. Chem. (1998) 9:783-792), and the reaction conditions set forth in this exemplary method can be suitably modified by the skilled artisan with regard to reaction amounts and ratios, temperature, time, and specific methods of purification. A generalized reaction approach is shown immediately below.

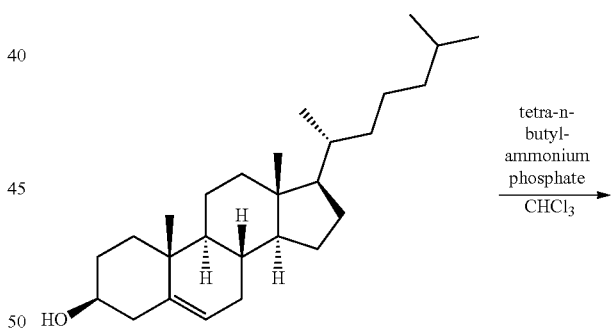

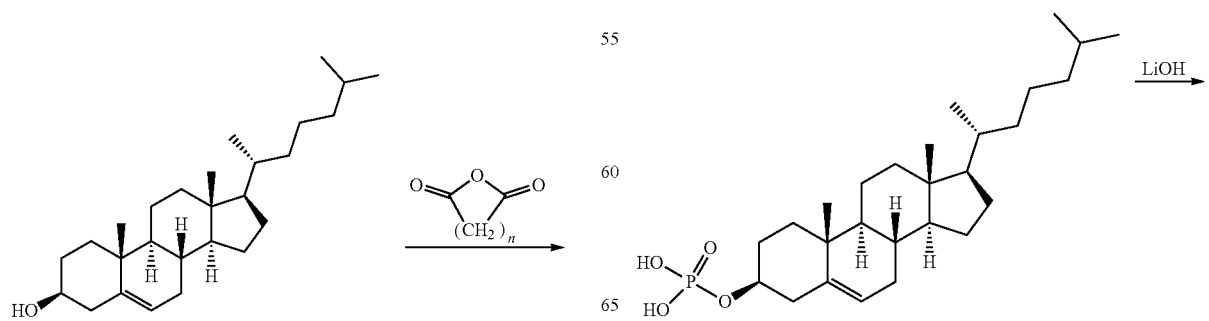

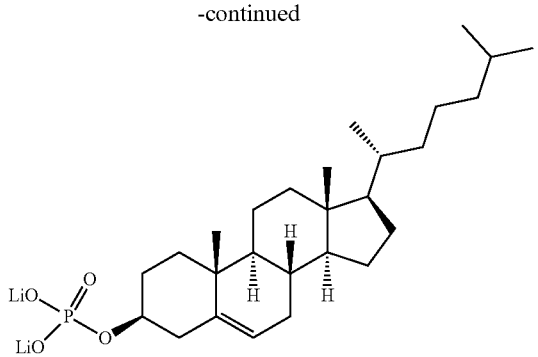

In one aspect, a lithium cholesterol carboxylate compounds, i.e., wherein R is —$(CH_2)_n(C=O)OLi$), where n is an integer having a value of 1, 2, 3, 4, 5, or 6, of the present disclosure can be prepared as generally described in U.S. Pat. Publ. No. 2015/0018436 for acids of general formula IX therein. For example, the lithium cholesterol carboxylate compounds, i.e., wherein R is —$(CH_2)_n(C=O)OLi$), where n is an integer having a value of 1, 2, 3, 4, 5, or 6, of the present disclosure can be prepared base catalyzed alkylation of cholesterol by tert-butylester of ω-bromoalkane acids having $C_2$-$C_{10}$ carbon atoms in an aprotic solvent followed by acidic cleavage (preferably using formic acid in diethylether) of the obtained tert-butylesters. Alternatively, the lithium cholesterol carboxylate compounds, i.e., wherein R is —$(CH_2)_n(C=O)OLi$), where n is an integer having a value of 1, 2, 3, 4, 5, or 6, of the present disclosure can be prepared by O-tosylation of cholesterol using standard techniques, followed by reaction ω-hydroxyalkanenitriles having $C_2$-$C_6$ carbon atoms in a nonpolar aprotic solvent at increased temperature (preferably in boiling toluene) followed by basic hydrolysis (preferably in a mixture of toluene and aqueous solution of NaOH at elevated temperature) of the intermediary O-[(3β)-cholest-5-en-3-yl]-ω-hydroxyalkanenitrile.

Methods of Using the Compounds.

In a further aspect, the present disclosure provides methods of treatment comprising administration of a therapeutically effective amount of a disclosed lithium cholesterol composition, including, but not limited to lithium cholesterol sulfate, or pharmaceutical composition as disclosed herein above to a subject in need thereof. A subject in need of treatment with the lithium cholesterol composition, including, but not limited to lithium cholesterol sulfate, or pharmaceutical compositions of the present disclosure can include, but are not necessarily limited to, subjects in need of treatment for neurodegenerative conditions (such as Alzheimer's disease (AD), Parkinson's disease (PD), amyotrophic laterals sclerosis (ALS), and the like), neurodevelopmental disorders (such as Autism spectrum disorders, and the like), traumatic brain injury and acute brain injury (such as caused by ischemic stroke, head trauma, and the like), radiation induced brain injury, mood disorders (such as suicidal ideation, bipolar disorder, depressive disorder), and other neuropsychiatric disorders, including but not limited to schizoaffective disorder, tic disorder (e.g., Tourette's syndrome), and the like. In particular, methods of the present disclosure include treatment of a patient in need of treatment for Alzheimer's disease, bipolar disorder, or autism spectrum disorder with a therapeutically effective amount of a lithium cholesterol composition, including, but not limited to lithium cholesterol sulfate, or lithium cholesterol composition, including, but not limited to lithium cholesterol sulfate, pharmaceutical composition of the present disclosure.

In embodiments, methods of the present disclosure also include increasing levels of inhibitory phosphorylation of GSK3β in cells or in a subject by exposing the cells or subject to an effective amount of a lithium cholesterol composition, including, but not limited to lithium cholesterol sulfate, or a lithium cholesterol composition, including, but not limited to lithium cholesterol sulfate, pharmaceutical composition of the present disclosure. In embodiments, methods of the present disclosure include decreasing levels of phosphorylation of tau in cells or in a subject by exposing the cells or subject to an effective amount of a lithium cholesterol composition, including, but not limited to lithium cholesterol sulfate, or a lithium cholesterol composition, including, but not limited to lithium cholesterol sulfate, pharmaceutical composition of the present disclosure. In embodiments, methods of the present disclosure include decreasing levels of LPS-induced TNFα in cells or in a subject by exposing the cells or subject to an effective amount of a lithium cholesterol composition, including, but not limited to lithium cholesterol sulfate, or a lithium cholesterol composition, including, but not limited to lithium cholesterol sulfate, pharmaceutical composition of the present disclosure. Embodiments of the present disclosure also include a combination of one or more of increasing levels of inhibitory phosphorylation of GSK3β, decreasing levels of phosphorylation of tau, and/or decreasing levels of LPS-induced TNFα in cells or in a subject by exposing the cells or subject to an effective amount of a lithium cholesterol composition, including, but not limited to lithium cholesterol sulfate, or lithium cholesterol composition, including, but not limited to lithium cholesterol sulfate, pharmaceutical composition of the present disclosure.

In embodiments of the methods of the present disclosure, administration of the pharmaceutical compositions including lithium cholesterol sulfate increases the lithium levels in the brain such that a subject has a greater brain to blood lithium level ratio than the brain to blood lithium level in a subject administered lithium chloride. Also, in methods of the present disclosure, administration of the pharmaceutical compositions including lithium cholesterol sulfate does not substantially increase lithium levels in the liver or kidney of the subject.

The methods of the present disclosure may further comprise administering an additional therapeutic and/or active agent for treating the neurological disorder before, during, or after the administration of the lithium cholesterol composition. The additional agent may be administered to the subject in the same composition as the lithium cholesterol composition or in separate compositions administered by the same or different anatomical routes. Accordingly, the compositions of the disclosure discussed above may include one or more such additional agents as well.

In some embodiments, the additional agent is an antidepressant, anti-convulsant, or mood stabilizer, or a combination of two or more of the foregoing. In some embodiments, the additional agent is a selective serotonin reuptake inhibitor (SSRI), serotonin-noroepinephrine reuptake inhibitor (SNRI), serotonin antagonist and reuptake inhibitor (SARI), monamine oxidase inhibitor (MAOI), carboxamide, fructose derivative, triazine, or a combination of two or more of the foregoing. In some embodiments, the disorder is a neurodegenerative disease such as Alzheimer's disease, and the additional agent is selected from the group consisting of a cholinesterase inhibitor (e.g., donepezil, rivastigmine, galantamine), N-methyl D-aspartate antagonist (e.g., memantine), or vitamin E, or a combination. In some embodiments, the additional agent is donepezil, rivastigmine, galantamine, memantine, or a combination of two or more of the foregoing.

Kits.

In a further aspect, the present disclosure relates to kits comprising a disclosed lithium cholesterol sulfate compound, or a pharmaceutically composition comprising lithium cholesterol composition, including, but not limited to lithium cholesterol sulfate, and instructions for administering the compound to treat a neurological disorder. In embodiment, the kit may further contain additional instructions for combining the pharmaceutical composition comprising lithium cholesterol composition, including, but not limited to lithium cholesterol sulfate, with additional components and/or additional therapeutic agents and administration of the composition to a subject to treat a neurological disorder.

The disclosed compounds and/or pharmaceutical compositions comprising the disclosed compounds can conveniently be presented as a kit, whereby two or more components, which may be active or inactive ingredients, carriers, diluents, and the like, are provided with instructions for preparation of the actual dosage form by the patient or person administering the drug to the patient. Such kits may be provided with all necessary materials and ingredients contained therein, or they may contain instructions for using or making materials or components that must be obtained independently by the patient or person administering the drug to the patient. In further aspects, a kit can include optional components that aid in the administration of the unit dose to patients, such as vials for reconstituting powder forms, syringes for injection, customized IV delivery systems, inhalers, etc. Additionally, a kit can contain instructions for preparation and administration of the compositions. The kit can be manufactured as a single use unit dose for one patient, multiple uses for a particular patient (at a constant dose or in which the individual compounds may vary in potency as therapy progresses); or the kit may contain multiple doses suitable for administration to multiple patients ("bulk packaging"). The kit components may be assembled in cartons, blister packs, bottles, tubes, and the like.

In a further aspect, the disclosed kits can be packaged in a daily dosing regimen (e.g., packaged on cards, packaged with dosing cards, packaged on blisters or blow-molded plastics, etc.). Such packaging promotes products and increases patient compliance with drug regimens. Such packaging can also reduce patient confusion. The present invention also features such kits further containing instructions for use.

In a further aspect, the present disclosure also provides a pharmaceutical pack or kit comprising one or more containers filled with one or more of the ingredients of the pharmaceutical compositions of the invention. Associated with such container(s) can be a notice in the form prescribed by a governmental agency regulating the manufacture, use or sale of pharmaceuticals or biological products, which notice reflects approval by the agency of manufacture, use or sale for human administration.

In various aspects, the disclosed kits can also comprise compounds and/or products co-packaged, co-formulated, and/or co-delivered with other components. For example, a drug manufacturer, a drug reseller, a physician, a compounding shop, or a pharmacist can provide a kit comprising a disclosed compound and/or product and another component for delivery to a patient.

Thus, in embodiments, the kit further includes at least one additional therapeutic agent for treatment of the neurological disorder. In embodiments, the neurological disorder can include neurodegenerative conditions, such as, but not limited to Alzheimer's disease, Parkinson's disease, and myotrophic laterals sclerosis (ALS); neurodevelopmental disorders, such as, but not limited to Autism spectrum disorders; traumatic brain injury, radiation induced brain injury, and acute brain injury, such as but not limited to, neurological injury caused by ischemic stroke, head trauma, and the like; mood disorders, such as but not limited to suicidal ideation, bipolar disorder, and depressive disorder; and other neuropsychiatric disorders, including but not limited to schizoaffective disorder, tic disorder (e.g., Tourette's syndrome).

In some embodiments, the additional agent is an antidepressant, anti-convulsant, or mood stabilizer, or a combination of two or more of the foregoing. In some embodiments, the additional agent is a selective serotonin reuptake inhibitor (SSRI), serotonin-noroepinephrine reuptake inhibitor (SNRI), serotonin antagonist and reuptake inhibitor (SARI), monamine oxidase inhibitor (MAOI), carboxamide, fructose derivative, triazine, or a combination of two or more of the foregoing. In some embodiments, the disorder is a neurodegenerative disease such as Alzheimer's disease, and the additional agent is selected from the group consisting of a cholinesterase inhibitor (e.g., donepezil, rivastigmine, galantamine), N-methyl D-aspartate antagonist (e.g., memantine), or vitamin E, or a combination. In some embodiments, the additional agent is donepezil, rivastigmine, galantamine, memantine, or a combination of two or more of the foregoing.

It is contemplated that the disclosed kits can be used in connection with the disclosed methods of making, the disclosed methods of using or treating, and/or the disclosed compositions.

Research Tools.

The disclosed compounds and pharmaceutical compositions have activity as activators/inhibitors of biomarkers associated with various neurological disorders. For instance, the lithium cholesterol sulfate compounds and pharmaceutical compositions of the present disclosure have activity as activating/increasing levels of inhibitory phosphorylation of GSK33, as inhibiting/decreasing levels of phosphorylation of tau, and inhibiting/decreasing levels of LPS-induced TNFα. The examples below demonstrate these effects in particular as compared to the levels of said compounds in a subject not receiving treatment with the lithium cholesterol composition, including, but not limited to lithium cholesterol sulfate, and/or pharmaceutical compositions or as compared to a subject or cells receiving treatment with a different lithium salt compounds, such as LiCl. As such, the disclosed compounds are also useful as research tools. Accordingly, one aspect of the present disclosure relates to a method of using a lithium cholesterol composition, including, but not limited to lithium cholesterol sulfate, of the disclosure as a research tool, the method comprising conducting a biological assay using a lithium cholesterol composition, including, but not limited to lithium cholesterol sulfate, of the invention. Compounds of the invention can also be used to evaluate new chemical compounds. Thus another aspect of the invention relates to a method of evaluating a test compound in a biological assay, comprising: (a) conducting a biological assay with a test compound to provide a first assay value; (b) conducting the biological assay with a compound of the invention to provide a second assay value; wherein step (a) is conducted either before, after or concurrently with step (b); and (c) comparing the first assay value from step (a) with the second assay value from step (b). Exemplary biological assays include, but are not limited to, a GSK3β activator assay, a tau phosphorulation inhibitor assay, and/or a LPS-induced TNFα inhibitor assay that can be conducted in vitro or in a cell culture system. Still another aspect of the invention relates to a method of studying a biological system, e.g., a model animal for a clinical condition, or biological sample.

Additional details regarding the methods, compositions, and organisms of the present disclosure are provided in the Examples below. The specific examples below are to be construed as merely illustrative, and not limitative of the remainder of the disclosure in any way whatsoever. Without further elaboration, it is believed that one skilled in the art can, based on the description herein, utilize the present disclosure to its fullest extent. All publications recited herein are hereby incorporated by reference in their entirety.

It should be emphasized that the embodiments of the present disclosure, particularly, any "preferred" embodiments, are merely possible examples of the implementations, merely set forth for a clear understanding of the principles of the disclosure. Many variations and modifications may be made to the above-described embodiment(s) of the disclosure without departing substantially from the spirit and principles of the disclosure. All such modifications and variations are intended to be included herein within the scope of this disclosure, and protected by the following claims.

The following examples are put forth so as to provide those of ordinary skill in the art with a complete disclosure and description of how to perform the methods and use the compositions and compounds disclosed herein. Efforts have been made to ensure accuracy with respect to numbers (e.g., amounts, temperature, etc.), but some errors and deviations should be accounted for. Unless indicated otherwise, parts are parts by weight, temperature is in ° C., and pressure is at or near atmospheric. Standard temperature and pressure are defined as 20° C. and 1 atmosphere.

It should be noted that ratios, concentrations, amounts, and other numerical data may be expressed herein in a range format. It is to be understood that such a range format is used for convenience and brevity, and thus, should be interpreted in a flexible manner to include not only the numerical values explicitly recited as the limits of the range, but also to include all the individual numerical values or sub-ranges encompassed within that range as if each numerical value and sub-range is explicitly recited. To illustrate, a concentration range of "about 0.1% to about 5%" should be interpreted to include not only the explicitly recited concentration of about 0.1 wt % to about 5 wt %, but also include individual concentrations (e.g., 1%, 2%, 3%, and 4%) and the sub-ranges (e.g., 0.5%, 1.1%, 2.2%, 3.3%, and 4.4%) within the indicated range. In an embodiment, the term "about" can include traditional rounding according to significant figures of the numerical value. In addition, the phrase "about 'x' to 'y'" includes "about 'x' to about 'y'".

EXAMPLES

Now having described the embodiments of the disclosure, in general, the examples describe some additional embodiments. While embodiments of the present disclosure are described in connection with the example and the corresponding text and figures, there is no intent to limit embodiments of the disclosure to these descriptions. On the contrary, the intent is to cover all alternatives, modifications, and equivalents included within the spirit and scope of embodiments of the present disclosure.

Example 1—Synthesis of Lithium Cholesterol Sulfate and In Vitro Assays of LICS Effect on Biomarkers of Alzheimer's Disease and Autism Spectrum Disorder Recent studies have shown that lithium treatment can reduce symptoms of Alzheimer's disease (AD) and Autism Spectrum Disorder (ASD). However, the presently available lithium salts have serious short- and long-term side effects, meaning that the use of these lithium salts requires frequent monitoring of blood chemistry and plasma lithium levels so as to avoid toxicity. Consequently, there is a demand for a safer and more effective lithium formulation to treat these diseases. The present example describes the synthesis of a disclosed lithium salt, lithium cholesterol sulfate (LiCS) (FIG. 1) and its therapeutic potential. This example also provides a comparison of the pharmacological effects of LiCS with that of lithium chloride (LiCl) and sodium cholesterol sulfate (NaCS) on markers of neurodegenerative disease in cell cultures.

This example examined the pharmacological effect of UCS on inhibitory GSK and tau phosphorylation as well as TNFα levels, important biomarkers associated with the pathogenesis of both AD and ASD. As will be described in greater detail in the results below, UCS proved more potent than LiCl in increasing inhibitory GSK3β (Ser9) phosphorylation (pGSK3β) in both CHO and SH-SY5Y cells. These agents dose-dependently increased pGSK3β, starting at 10 µM for LiCS and 60 µM for LiCl and maximally by approximately 100% at 60 µM for LiCS and 1.25 mM for LiCl, without altering total GSK3β levels. In HEK293/tau cells, UCS reduced tau (Thr231) phosphorylation (ptau) starting at 10 µM and maximally by 63% at 40 µM without altering total tau levels, but ptau levels were not altered by LiCl at any dose between 60 µM and 1.25 mM. In BV2 cells, UCS and LiCl decreased LPS-induced TNFα levels, starting at 20 µM for LiCS and 5 mM for LiCl, and maximally by approximately 30% at 80 µM for UCS and 20 mM for LiCl. NaCS at any dose between 5 and 90 µM did not alter pGSK30, ptau or LPS-induced TNFα. Thus, LiCS represents a new pharmaceutical compound with potent pharmacodynamics for treatment of AD and ASD.

Materials and Methods

Reagents

Lithium cholesterol sulfate (LiCS, 96%) was synthetized by New England Discovery Partners (USF) using variations of procedures for sulfating molecules (22, 23, incorporated by reference herein). Specifically, LiCS was synthesized as generally described in FIG. 1A.

LiCS and lithium chloride (LiCl, ≥99%, Millipore Sigma, St Louis, Mo.) were dissolved in methanol at 250 mM, and sodium cholesterol sulfate (NaCS, ≥98.0%, Millipore Sigma) was dissolved in methanol at 100 mM. LPS (Millipore Sigma) was diluted in Dulbecco's Modified Eagle's Medium (DMEM) at 10 µg/ml. Mouse TNFα uncoated ELISA Kit was purchased from Thermo Fisher Scientific (Waltham, Mass.). Primary antibodies include anti-pGSK3β (Ser9) and anti-total GSK3β (Thermo Fisher Scientific), anti-p-tau (Thr231) and anti-total tau (tau12, Millipore Sigma). The secondary antibodies used were anti-rabbit Ig G and anti-mouse Ig G, respectively (Millipore Sigma).

Cell Culture

Human neuroblastoma SH-SY5Y cells (ATCC, Manassas, Va.) were cultured in DMEM/Nutrient Mixture F-12 (DMEM/F-12), 10% fetal bovine serum (FBS) and 15 mM HEPES. Chinese Hamster Ovary cells (CHO, Millipore Sigma), human embryonic kidney 293 cells expressing wild-type tau (HEK293/tau cells, ATCC) and mouse BV2 microglial cells (Creative Bioarray, Shirley, N.Y.) were cultured in DMEM with 10% FBS. SH-SY5Y cells and CHO cells were cultured in 24-well plates at a density of $2.5 \times 10^5$ cells/well. HEK293/tau cells were cultured in 24-well plates at a density of $3.5 \times 10^5$ cells/well, after being treated with Tetracycline (1:1000) for about 24 h to create high and stable cells lines (24).

Western Blot Analysis for GSK and Tau Phosphorylation

Cells were treated with LiCS or NaCS at 0, 5, 10, 20, 40, 60 or 90 µM or LiCl at 0, 0.06, 0.15, 0.3, 0.6, 1.2 and 2.5 mM for 18 hours, followed by washing with ice-cold PBS 3×, lysis with cell lysis buffer and centrifugation at $1.4 \times 10^4$ rpm for 20 minutes. The supernatants were then used for analysis of GSK3β (Ser) and tau ($Thr^{231}$) phosphorylation by Western Blot (WB) and WB bands were calculated by Image J software (Java 1.6.0_20, NIH, USA).

Microglial Inflammatory Activity Analysis

Microglial cells ($3.5 \times 10^5$/well) were treated with LPS at 100 ng/mL in the presence of LiCS, NaCS or LiCl at increasing concentrations for 3 hours, followed by analysis of TNFα levels in conditioned media by ELISA according to the manufacturer's instructions.

Statistical Analysis

All statistical analyses were conducted using Student's t-test and One-way ANOVA with SPSS 13.0. Data were presented as mean±standard deviation from at least three separate experiments. P value less than 0.05 was considered statistically significant.

Results and Discussion

Effects of UCS, LiCl and NaCS on Inhibitory pGSK3p (Ser9) Phosphorylation in SH-SY5Y Cells and CHO Cells:

In order to discover a potentially more effective and safer lithium formulation for treating AD and ASD, LiCS was synthesized, and its pharmacological effects on three biomarkers of the conditions—(GSK3β (Ser) phosphorylation, tau ($Thr^{231}$) phosphorylation, and LPS-induced TNFα production)—were determined and compared with that of LiCl and NaCS in cell cultures. LiCS and LiCl dose-dependently increased inhibitory GSK3β (Ser) phosphorylation (pGSK3β) in both CHO and SH-SY5Y cells. For CHO cells, LiCS increased pGSK3β starting at 10 µM and maximally by 92% at 60 µM. In comparison, LiCl increased pGSK3β starting at 160 µM and maximally by 91% at 1.25 mM (FIGS. 2A, 2B & 2E).

Similarly, for SH-SY5Y cells, LiCS increased pGSK3β starting at 10 µM and maximally by 90% at 90 µM, while LiCl increased pGSK3β starting at 60 µM and maximally by 119% at 2.5 mM (FIGS. 2C, 2D & 2F). Notably, NaCS at 5-90 µM did not alter pGSK3β, and neither LiCS, LiCl nor NaCS altered total GSK3β at any dose. Taken together, these findings indicate that LiCS is approximately 21-28 fold more potent than LiCl in increasing inhibitory GSK3β (Ser) phosphorylation. At 60 µM, LiCS maximally while LiCl minimally increased pGSK3β levels.

Figure 3B:
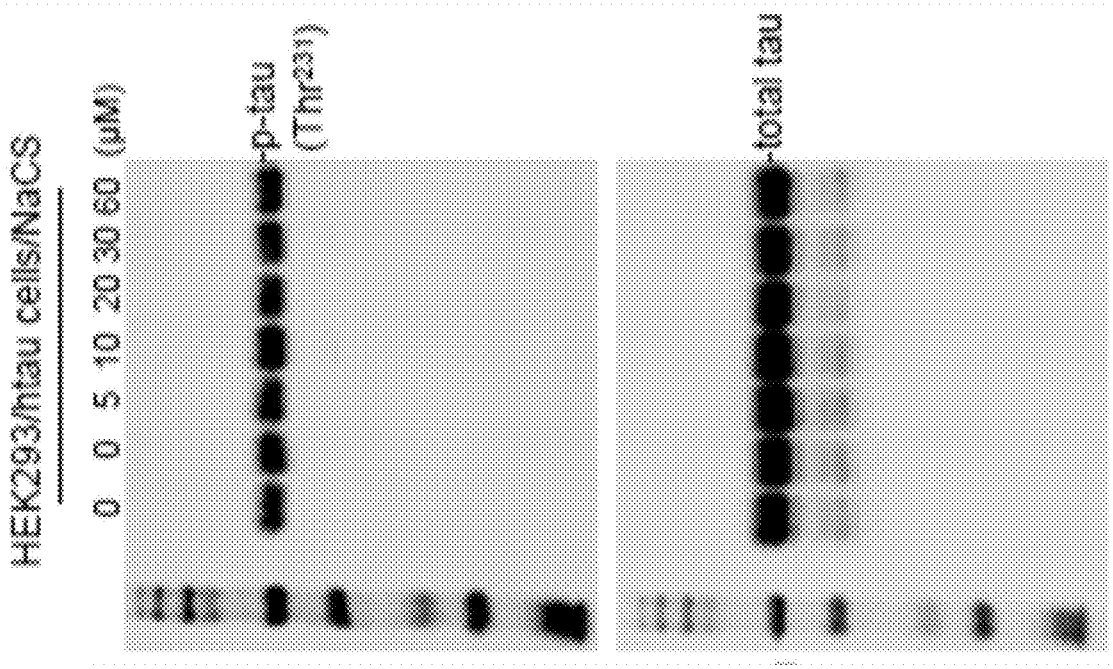
FIGS. 3A-3D illustrate a comparison of LiCS vs. LiCl effect on tau (Thr231) phosphorylation and that LiCS reduces tau (Thr231) phosphorylation at micromolar levels. HEK293/tau cells were treated with LiCS (FIG. 3A) or NaCS at 0-60 μM (FIG. 3B) or LiCl at 60 μM to 1.25 mM for 18 h (FIG. 3C) followed by analysis of phosphor-tau (Thr231) and total tau levels in cell homogenates by WB. Levels of phospo-tau (Thr231) were determined by densitometry analysis of three independent experiments and represented as means±SD (FIG. 3D). Asterisk indicates P<0.05 compared with no treatment (100% of control). Note that neither NaCS nor LiCl altered ptau, and neither LiCS, LiCl nor NaCS altered total tau levels.
Figure 3A:
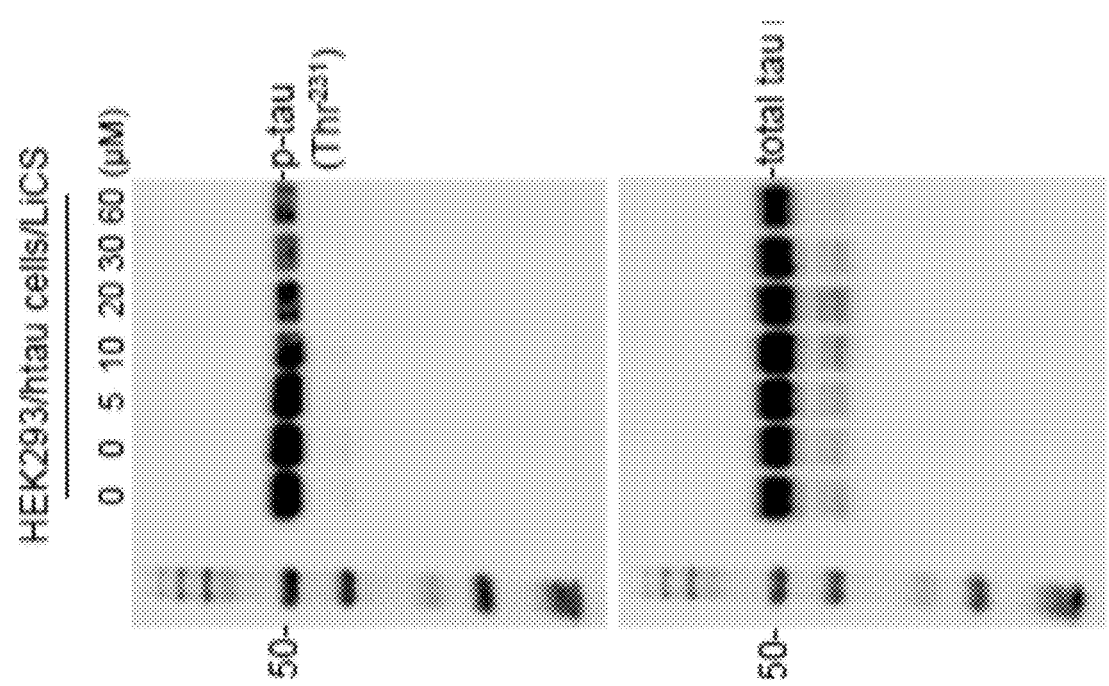
Figure 3D:
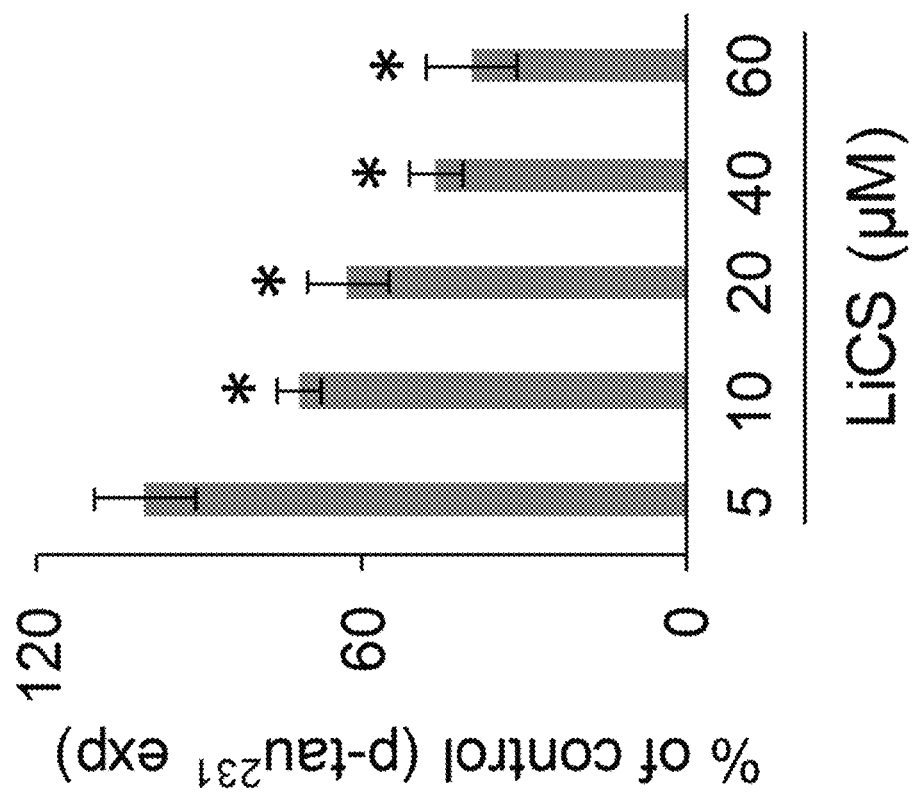
Figure 3C:
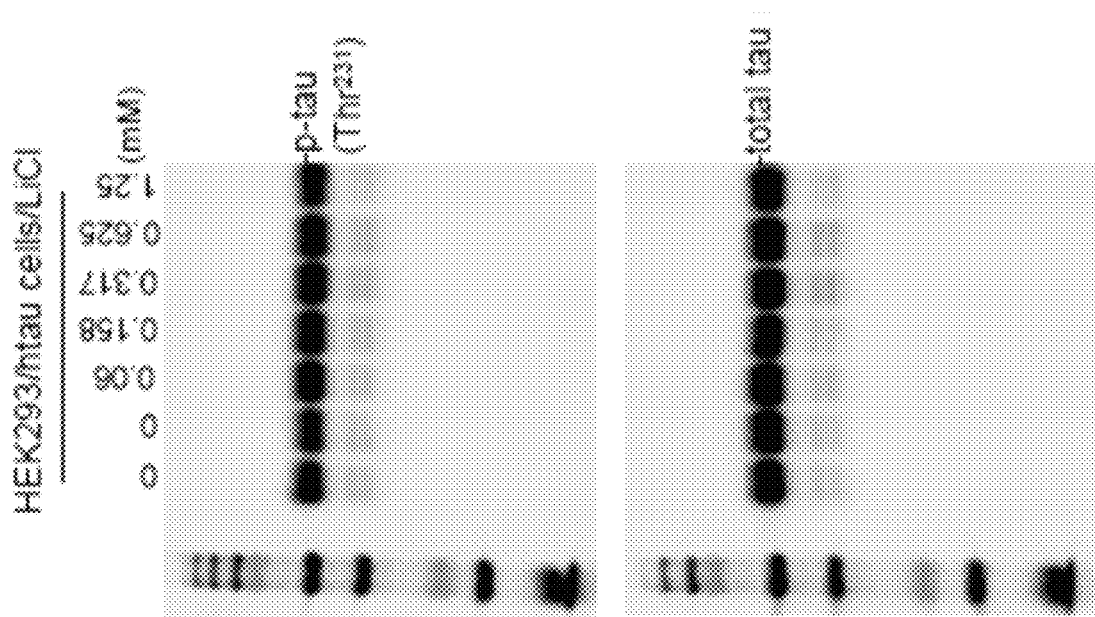

Effects of UCS, LiCl and NaCS Treatment on Tau Phosphorylation in HEK293/Tau Cells:

In addition to increasing GSK3β phosphorylation, LiCS dose-dependently decreased tau (Thr231) phosphorylation (ptau) in HEK293/tau cells. LiCS decreased ptau starting at 10 µM and maximally by 63% at 40 µM (FIGS. 3A & 3D). However, neither LiCl at any dose between 60 µM and 1.25 mM nor NaCS at any dose between 5 and 60 µM altered ptau, and neither LiCS, NaCS nor LiCl at any dose altered total tau (FIGS. 3B & 3C). Thus, UCS reduces tau phosphorylation at micromolar levels, while LiCl is ineffective even at millimolar levels.

Figure 4:
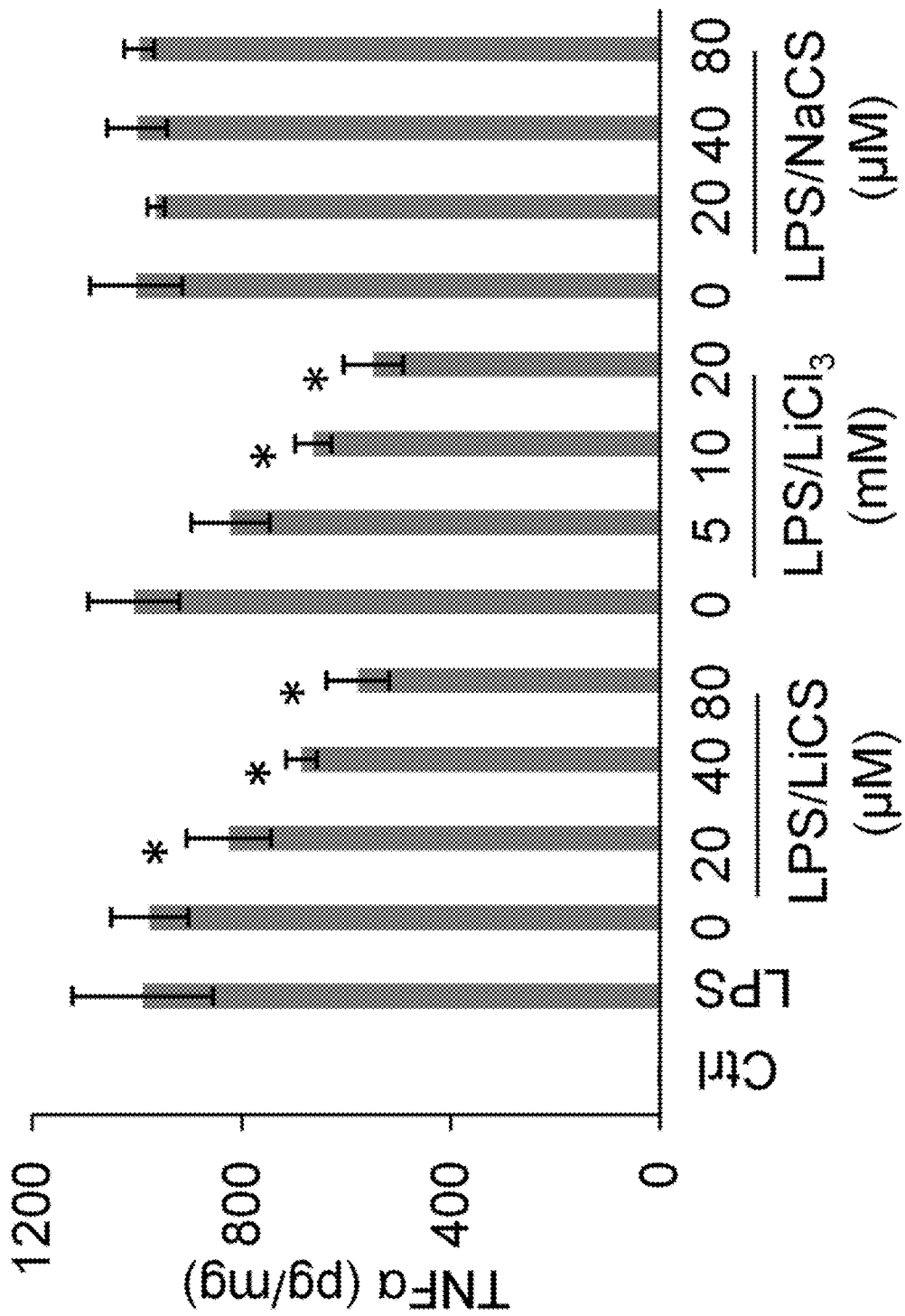
FIG. 4 is a graph illustrating that LiCS is more effective than LiCl in reducing microglial LPS-induced TNFα production. Microglial BV2 cells were treated with LPS at 100 ng/ml in the absence or presence of LiCS or NaCS at 0, 20, 40 or 80 µM or LiCl at 5, 10 or 20 mM for 3 h, followed by analysis of TNFα levels in conditioned media by ELISA, represented as means±SD. Asterisk indicates P<0.05 compared with LPS treatment alone.

Effects of UCS, LiCl and NaCS Treatment on Microglial LPS-Mediated TNFα Production:

In order to determine the effect of LiCS on microglial inflammation, mouse microglial cells (BV2) were treated with lipopolysaccharides (LPS, 100 ng/ml) together with UCS, LiCl or NaCS for 3 hours, followed by TNFα analysis by ELISA. Cell morphology was not altered by any treatment. Both UCS and LiCl dose-dependently decreased TNFα (FIG. 4). UCS decreased TNFα starting at 20 µM and maximally by 28% at 80 µM, while LiCl decreased TNFα starting at 5 mM and maximally by 34% at 20 mM. However, TNFα level was not altered by NaCS at any concentration between 20 and 80 µM. Thus, LiCS was approximately 250-fold more potent than LiCl for reducing LPS-induced TNFα production.

Discussion

In order to develop a new, more effective lithium formulation for the potential treatment of AD and ASD, the pharmacological effects of LiCS were determined in comparison with LiCl and NaCS on markers of neurodegenerative disease in cell cultures. It was found that while both LiCS and LiCl increased inhibitory GSK3β (Ser9) phosphorylation (pGSK30) in a dose-dependent fashion in CHO and SH-SY5Y cells, UCS increased pGSK3β at low micromolar levels while LiCl required high micromolar and low millimoloar levels (FIGS. 2A-2F). Thus, UCS was 21-28 fold more potent than LiCl. In addition, UCS reduced tau (Thr231) phosphorylation at micromolar levels (FIGS. 3A and 3D), while LiCl failed to alter tau phosphorylation at even millimolar levels (FIG. 3C), in HEK293/tau cells. In microglial cultures, UCS was approximately 250 fold more potent than LiCl for reducing LPS-induced TNFα production (FIG. 4). Notably, NaCS at any dose between 5 and 90 µM failed to alter pGSK3β (FIGS. 2A and 2C), ptau (FIG. 3B), or LPS-induced TNFα (FIG. 4). Thus, UCS modulates important markers of AD and ASD and thus provides a novel and effective treatment for AD, ASD and other related neurodegenerative diseases.

Lithium as a mood stabilizer has been used in the standard pharmacological treatment of bipolar disorder (BD) for more than 60 years (11, 12). It remains to be recommended by many treatment guidelines as the first-line treatment for acute mania, and prophylactically for recurrent manic and depressive episodes. Lithium can help prevent suicide and is associated with a lower risk for all-cause mortality in patients with mood disorders (11, 12). In recent years, there have appeared many experimental studies describing new effects of lithium for treatment of neurodegenerative diseases such as AD (13, 14), ASD (7, 15, 16), Parkinson's disease (PD) (25, 26), stroke and spinal cord injury (27, 28). Regarding PD, studies have found that lithium treatment of hNT neurons increases tyrosine hydroxylase (TH) activity, the rate limiting enzyme in the synthesis of dopamine (25). Moreover, brief exposure of hNT neurons to lithium increases cell survival, TH expression and fibre outgrowth after transplantation into the striatum of hemiparkinsonian rats. Interestingly, recent studies suggest that lithium treatment may also be effective for peripheral disorders such as atherosclerosis and ischemic coronary disease, which may be mediated in part by suppression of MMP-9 gene expression in macrophages (29, 30). Inhibition of MMP-9 by lithium may help maintain the BBB, since toxic free radicals can disrupt the BBB via increased activity of MMP (31, 32). In addition, lithium has been suggested to be beneficial for treatment of granulocytopenia resulting from radiation and chemotherapy, to boost immunoglobulins after vaccination and enhance natural killer cell activity (27). Lithium may also increase gut microbial richness and diversity, which can play an important role in its therapeutic effectiveness for neurodegenerative diseases (33). Therefore, lithium salts represent potential drugs for the treatment of diverse central and peripheral diseases.

As an ion, lithium is formulated in lithium salts. Lithium carbonate is usually applied in the clinic, but other lithium salts such as lithium citrate, lithium sulfate, lithium orotate and lithium chloride, are also sometimes used as alternatives. All conventional lithium salt treatments require frequent monitoring of blood chemistry and plasma lithium levels so as to avoid toxicity, which may discourage patients from choosing these drugs. For this reason, some novel lithium salts such as lithium carbonate sustained-release tablets or controlled-release tablets have been developed. Remarkably, recent studies from our laboratory have also found that different lithium salts can have profoundly different pharmacokinetic effects depending on the associated anion. For example, treatment with lithium salicylate produced longer elevated plasma lithium levels with a slower elimination process compared with lithium lactate treatment in rats (34). In addition, LISPRO, a novel ionic co-crystal of lithium salicylate and L-proline, produced significantly higher brain lithium levels and more steady plasma lithium levels compared with lithium carbonate or lithium salicylate in mice (35) and rats (36). Long term oral administration of LISPRO reduced AD pathology, including β-amyloid plaques, tau hyperphosphorylation, neuroinflammation, neuronal and synaptic protein loss and GSK3β activity, without eliciting renal inflammation, in Tg2576 and 3XTg AD mice models (35). Thus, LISPRO might be a superior form of lithium with improved safety and efficacy as a potentially new disease modifying therapeutic for AD. However, continued exploration of ways to improve lithium's therapeutic profile lent to the surprising discovery of the improved potency and safety of the novel lithium salts of the present disclosure.

Cholesterol sulfate was first isolated from human plasma in 1965 and found to be present in a concentration of 300 µg/100 ml (37), thus being one of the most abundant sterol sulfates in the plasma. In addition, cholesterol sulfate is a normal constituent in a variety of human tissues including cell membranes, platelets and red blood cells (18). The sulfate moiety of cholesterol sulfate has a pKa of 3.3, indicating that it is normally ionized under physiologic conditions (18). Thus, the sulfoconjugation of cholesterol results in the conversion of a rather rigid hydrophobic molecule into a very amphiphilic compound containing a highly charged subgroup. The hydrophobic/hydrophilic property of cholesterol sulfate represents an important characteristic underlying its biologic action and making it better suited for interactions with membrane constituents. The rate of intermembrane exchange for cholesterol sulfate was found to be approximately 10-fold faster than for cholesterol in all liposomes tested (38). In addition, cholesterol sulfate can be considered to be a potent thermosensitizer, which enhances the selectivity of biological drug carriers (39). In the present study, cholesterol sulfate was tested as a carrier for lithium in the development of a novel lithium salt, UCS. It was discovered that the use of LiCS may allow lithium to more easily pass through the cell membrane as well as intestinal and blood brain barriers after peripheral or oral administration, thereby allowing it to more readily target intracellular pathological processes than clinically available lithium chloride.

In the United States, Alzheimer's disease (AD) is the most common cause of dementia, accompanied by substantial economic and emotional costs. During 2015, more than 15 million family members who provided care to AD patients had an estimated total cost of 221 billion dollars. Autism spectrum disorder (ASD), another neurodegenerative disease, currently afflicts around 20 per 1,000 children between the ages of 6 and 17. LiCS represents a new treatment option with good pharmacological potential for treatment of neurodegenerative disorders such as AD and ASD by allowing lithium to more readily access intracellular pathological processes. Additional studies described in the examples below using animal models further explore its pharmacokinetic, pharmacodynamics and therapeutic potential.

Example 2—In Vivo Mouse Studies Demonstrating Pharmacokinetics Profile of UCS Vs LiCl Introduction In a recent study, we found that a lithium cocrystal (LISPRO), composed of lithium salicylate and proline, reduced AD pathology in two AD mouse models, Tg2576 and 3XTg-AD. In addition, LISPRO reduced AD-related behavioral impairment (Habib et al., Journal of Neuroscience Research, revised, 2019). Since long term salicylate treatment can be harmful to the elderly, investigation of another approach was desired, and lithium cholesterol sulfate was identified as a possible candidate. Cholesterol is present in all cellular membranes, where its supports proper structure and function. The brain contains about 25% of the body's cholesterol and is essential for synaptic function. Cholesterol sulfate a quantitatively important sterol sulfate in human plasma. Cholesterol sulfate is also a normal constituent in a variety of human tissues including skin, hair, nails, aorta, adrenal, liver, and kidney. The highest level of cholesterol sulfate in the rat brain occurred in subcellular fraction rich in nerve endings. It stabilizes cell membranes, regulates the activity of serine proteases and protein kinase C, such as those involved in blood clotting, fibrinolysis, epidermal cell adhesion and barrier formation, and is a substrate for the synthesis of neurosteroids, such as pregnenolone, DHEA, estrogen and testosterone sulfate. Sulfoconjugation of cholesterol results in the conversion of a rather rigid hydrophobic molecule into a very amphiphilic compound containing a highly charged subgroup. The hydrophobic/hydrophilic property of cholesterol sulfate represents an important characteristic in its biologic action. This aspect of the structure of cholesterol sulfate makes it a candidate for interactions with membrane constituents as well as absorption and transport freely into the blood stream and across the blood brain barrier.

Materials and Methods:

Chemistry:

LiCS was first synthesized by collaboration with New England Discovery Partners (NEDP) as described above in Example 1 (FIG. 1). The preparations and purity of the final product were confirmed by mass spectrometry.

Mouse Protocol:

C57BL/6J male mice at 4 months of age were treated with LiCl or LiCS at 0.04 mmol lithium/mouse p.o by gavage, followed by determination of lithium levels in blood plasma, brain, kidney and liver at 0.5, 1, 2, 3, 5 and 24 h after gavage by ELISA (N=2 mice/time point).

Blood and Tissue Lithium EUSA:

At 0.5, 1, 2, 3, 5 and 24 h after treating mice with LiCl or LiCS p.o. by gavage, mice were anesthetized with isoflourane (50 mg/kg) (Sigma-Aldrich), euthanized by bilateral thoracotomy, and blood was collected. Brain, kidney, and liver were harvested, homogenized in 400 μL ddH2O with Minilys tissue homogenizer (Bertin Technologies, Montigny-le-Bretonneux, France), and centrifuged for 30 min. Lithium levels in plasma and supernatants from brain, kidney, and liver homogenates were determined by ELISA (Biovision, Milpitas, Calif.) following the manufacturer's instructions. Plasma, brain, kidney and liver homogenates from control mice were used to generate standard curve.

Results:

As illustrated in FIG. 5A, Lithium levels in the blood increased between 0.5 and 5 h after LiCl and between 0.5 and 24 h after LiCS treatment. In addition, lithium levels in the brain increased at 5 h after LiCl and at 0.5 and 5 h after LiCS treatment (FIG. 5B), and lithium levels in the kidney increased at 0.5 and 5 h after LiCl but failed to increase at any time after LiCS treatment (FIG. 5B). Lithium levels in the liver failed to increase at any time after LiCl or LiCS treatment (FIG. 5B). There was no detectable lithium in plasma, brain, kidney or liver before treatment (0 time, data not shown). All mice received normal drinking water ad libitum during the treatment period. Lithium ELISA results are presented as the mean (±s.d.). Asterisk indicates P<0.05 versus LiCl treatment as determined by ANOVA.

Discussion

These in vivo results suggest that lithium blood levels are more stable and last longer after UCS compared with LiCl oral treatment and that UCS more readily crosses the blood-brain barrier. In addition, LiCl but not UCS treatment markedly increases lithium levels in the kidneys. These results are important, since lithium chronic treatment has been associated with several forms of kidney injury (40, 41). It is estimated that impaired urinary concentrating ability is present in at least 50% of individuals on chronic lithium therapy, a condition called lithium-induced nephrogenic diabetes insipidus. Continued use of lithium can lead to more serious kidney damage in an aggravated form of diabetes insipidus and chronic kidney failure. Indeed, chronic kidney disease is found in about one-third of people undergoing long-term lithium treatment, according to one study. Some forms of lithium-caused kidney damage may be progressive and lead to end-stage kidney failure.

These data demonstrate that this novel compound (LiCS) would allow lithium to more readily cross the intestinal and blood-brain barriers for oral treatment of bipolar affective disorder. Lithium salts have been used in psychiatry to treat bipolar disorder for many years and are now still considered as a first-line therapy for acute and long-term treatment of bipolar disorder. In recent years, lithium has also been shown to be a potential therapeutic for other neurodegenerative diseases, such as Alzheimer's disease (AD) and autism (ASD). CS has a hydrophobic/hydrophilic property which is well-suited for interaction with membrane constituents and present results demonstrate CS as a suitable carrier for the delivery of drugs across the intestinal and blood brain barriers. In addition CS, a normal constituent of a variety of human tissues, may also be beneficial in the treatment of AD and ASD, as well as other diseases potentially resulting from sulfer shortage, including eczema and asthma. The results from the present examples demonstrate that UCS appears particularly beneficial for treating neurodegenerative disease.

REFERENCES

1. Scheltens P, Blennow K, Breteler M M, de Strooper B, Frisoni G B, Salloway S, Van der Flier W M. Alzheimer's disease. Lancet (London, England). 2016; 388(10043): 505-17. Epub 2016 Feb. 28. doi: 10.1016/s0140-6736(15) 01124-1. PubMed PMID: 26921134.
2. Wang J, Gu B J, Masters C L, Wang Y J. A systemic view of Alzheimer disease—insights from amyloid-beta metabolism beyond the brain. Nature reviews Neurology. 2017; 13(11):703. Epub 2017 Oct. 14. doi: 10.1038/nmeurol.2017.147. PubMed PMID: 29027541.
3. Clayton K A, Van Enoo A A, Ikezu T. Alzheimer's Disease: The Role of Microglia in Brain Homeostasis and Proteopathy. Frontiers in neuroscience. 2017; 11:680. Epub 2018 Jan. 10. doi: 10.3389/fnins.2017.00680. PubMed PMID: 29311768; PMCID: PMC5733046.
4. Matsunaga S, Kishi T, Annas P, Basun H, Hampel H, Iwata N. Lithium as a Treatment for Alzheimer's Disease: A Systematic Review and Meta-Analysis. Journal of Alzheimer's disease: JAD. 2015; 48(2):403-10. Epub 2015 Sep. 25. doi: 10.3233/jad-150437. PubMed PMID: 26402004.
5. Fitzpatrick S E, Srivorakiat L, Wink L K, Pedapati E V, Erickson C A. Aggression in autism spectrum disorder presentation and treatment options. Neuropsychiatric disease and treatment. 2016; 12:1525-38. Epub 2016 Jul. 7. doi: 10.2147/ndtS84585. PubMed PMID: 27382295; PMCID: PMC4922773.
6. Siegel M, Beresford C A, Bunker M, Verdi M, Vishnevetsky D, Karisson C, Teer O, Stedman A, Smith K A. Preliminary investigation of lithium for mood disorder symptoms in children and adolescents with autism spectrum disorder. Journal of child and adolescent psychopharmacology. 2014; 24(7):399-402. Epub 2014 Aug. 6. doi: 10.1089/cap.2014.0019. PubMed PMID: 25093602.
7. Canitano R. Mood Stabilizers in Children and Adolescents With Autism Spectrum Disorders. Clinical neuropharmacology. 2015; 38(5):177-82. Epub 2015 Sep. 15. doi: 10.1097/wnf.0000000000000096. PubMed PMID: 26366961.
8. Blumberg S J, Bramlett M D, Kogan M D, Schieve L A, Jones J R, Lu M C. Changes in prevalence of parent-reported autism spectrum disorder in school-aged U.S. children: 2007 to 2011-2012. National health statistics reports. 2013(65):1-11, 1 p following Epub 2013 Mar. 20. PubMed PMID: 24988818.
9. Theoharides T C, Tsilioni I, Patel A B, Doyle R. Atopic diseases and inflammation of the brain in the pathogenesis of autism spectrum disorders. Translational psychiatry. 2016; 6(6):e844. Epub 2016 Jun. 29. doi: 10.1038/tp.2016.77. PubMed PMID: 27351598; PMCID: PMC4931610.
10. Gassowska M, Baranowska-Bosiacka I, Moczydlowska J, Tamowski M, Pilutin A, Gutowska I, Struzynska L, Chlubek D, Adamczyk A. Perinatal exposure to lead (Pb) promotes Tau phosphorylation in the rat brain in a GSK-3beta and CDK5 dependent manner Relevance to neurological disorders. Toxicology. 2016; 347-349:17-28. Epub 2016 Mar. 26. doi: 10.1016/j.tox.2016.03.002. PubMed PMID: 27012722.
11. Richardson T, Macaluso M. Clinically relevant treatment considerations regarding lithium use in bipolar disorder. Expert opinion on drug metabolism & toxicology. 2017; 13(11):1105-13. Epub 2017 Oct. 3. doi: 10.1080/17425255.2017.1386653. PubMed PMID: 28965429.

12. Oruch R, Elderbi M A, Khattab H A, Pryme I F, Lund A. Lithium: a review of pharmacology, clinical uses, and toxicity. European journal of pharmacology. 2014; 740: 464-73. Epub 2014 Jul. 6. doi: 10.1016/j.ejphar.2014.06.042. PubMed PMID: 24991789.
13. Devanand D P, Strickler J G, Huey E D, Crocco E, Forester B P, Husain M M, Vahia I V, Andrews H, Wall M M, Pelton G H. Lithium Treatment for Agitation in Alzheimer's disease (Lit-A D): Clinical rationale and study design. Contemporary clinical trials. 2018; 71:33-9. Epub 2018 Jun. 4. doi: 10.1016/j.cct.2018.05.019. PubMed PMID: 29859917; PMCID: PMC6082137.
14. Devanand D P, Pelton G H, D'Antonio K, Strickler J G, Kreisl W C, Noble J, Marder K, Skomorowsky A, Huey E D. Low-dose Lithium Treatment for Agitation and Psychosis in Alzheimer Disease and Frontotemporal Dementia: A Case Series. Alzheimer disease and associated disorders. 2017; 31(1):73-5. Epub 2016 Nov. 8. doi: 10.1097/wad.0000000000000161. PubMed PMID: 27819842; PMCID: PMC5322244.
15. Wu X, Bai Y, Tan T, i H, Xia S, Chang X, Zhou Z, Zhou W, Li T, Wang Y T, Dong Z. Lithium ameliorates autistic-like behaviors induced by neonatal isolation in rats. Frontiers in behavioral neuroscience. 2014; 8:234. Epub 2014 Jul. 16. doi: 10.3389/fnbeh.2014.00234. PubMed PMID: 25018711; PMCID: PMC4071979.
16. Serret S, Thummler S, Dor E, Vesperini S, Santos A, Askenazy F. Lithium as a rescue therapy for regression and catatonia features in two SHANK3 patients with autism spectrum disorder case reports. BMC psychiatry. 2015; 15:107. Epub 2015 May 8. doi: 10.1186/s12888-015-0490-1. PubMed PMID: 25947967; PMCID: PMC4428105.
17. Foglia F, Rogers S E, Webster J R, Akeroyd F A, Gascoyne K F, Lawrence M J, Barlow D J. Neutron Scattering Studies of the Effects of Formulating Amphotericin B with Cholesteryl Sulfate on the Drug's Interactions with Phospholipid and Phospholipid-Sterol Membranes. Langmuir: the ACS journal of surfaces and colloids. 2015; 31(29):8042-51. Epub 2015 Jul. 4. doi: 10.1021/acs.langmuir.5b01365. PubMed PMID: 26139630.
18. Strott C A, Higashi Y. Cholesterol sulfate in human physiology: what's it all about? J Lipid Res. 2003; 44(7): 1268-78. Epub 2003 May 6. doi: 10.1194/jlr.R300005-JLR200. PubMed PMID: 12730293.
19. Merten M, Dong J F, Lopez J A, Thiagarajan P. Cholesterol sulfate: a new adhesive molecule for platelets. Circulation. 2001; 103(16):2032-4. Epub 2001 Apr. 25. PubMed PMID: 11319189.
20. Seneff S, Davidson R, Mascitelli L. Might cholesterol sulfate deficiency contribute to the development of autistic spectrum disorder? Medical hypotheses. 2012; 78(2): 213-7. Epub 2011 Nov. 22. doi: 10.1016/j.mehy.2011.10.026. PubMed PMID: 22098722.
21. Beel A J, Sakakura M, Barrett P J, Sanders C R. Direct binding of cholesterol to the amyloid precursor protein: An important interaction in lipid-Alzheimer's disease relationships?Biochimica et biophysica acta. 2010; 1801 (8):975-82. Epub 2010 Mar. 23. doi: 10.1016/j.bbalip.2010.03.008. PubMed PMID: 20304095; PMCID: PMC2886191.
22. Al-Horani R A, Desai U R. Chemical Sulfation of Small Molecules—Advances and Challenges. Tetrahedron. 2010; 66(16):2907-18. Epub 2010 Aug. 7. doi: 10.1016/j.tet.2010.02.015. PubMed PMID: 20689724; PMCID: PMC2913517.
23. Donazzolo E, Gucciardi A, Mazzier D, Peggion C, Pirillo P, Naturale M, Moretto A, Giordano G. Improved synthesis of glycine, taurine and sulfate conjugated bile acids as reference compounds and internal standards for ESI-M S/M S urinary profiling of inborn errors of bile acid synthesis. Chemistry and physics of lipids. 2017; 204:43-56. Epub 2017 Mar. 17. doi: 10.1016/j.chemphyslip.2017.03.004. PubMed PMID: 28300538.
24. Bandyopadhyay B, Li G, Yin H, Kuret J. Tau aggregation and toxicity in a cell culture model of tauopathy. The Journal of biological chemistry. 2007; 282(22):16454-64. Epub 2007 Apr. 13. doi: 10.1074/jbc.M700192200. PubMed PMID: 17428800.
25. Willing A E, Zigova T, Milliken M, Poulos S, Saporta S, McGrogan M, Snable G, Sanberg P R. Lithium exposure enhances survival of NT2N cells (hNT neurons) in the hemiparkinsonian rat. The European journal of neuroscience. 2002; 16(12):2271-8. Epub 2002 Dec. 21. PubMed PMID: 12492421.
26. Zigova T, Willing A E, Tedesco E M, Borlongan C V, Saporta S, Snable G L, Sanberg P R. Lithium chloride induces the expression of tyrosine hydroxylase in hNT neurons. Experimental neurology. 1999; 157(2):251-8. Epub 1999 Jun. 12. doi: 10.1006/exnr.1999.7054. PubMed PMID: 10364437.
27. Young W. Review of lithium effects on brain and blood. Cell transplantation. 2009; 18(9):951-75. Epub 2009 Jun. 16. doi: 10.3727/096368909x471251. PubMed PMID: 19523343.
28. Zhu H, Poon W, Liu Y, Leung G K, Wong Y, Feng Y, Ng S C P, Tsang K S, Sun D T F, Yeung D K, Shen C, Niu F, Xu Z, Tan P, Tang S, Gao H, Cha Y, So K F, Fleischaker R, Sun D, Chen J, Lai J, Cheng W, Young W. Phase I-II Clinical Trial Assessing Safety and Efficacy of Umbilical Cord Blood Mononuclear Cell Transplant Therapy of Chronic Complete Spinal Cord Injury. Cell transplantation. 2016; 25(11):1925-43. Epub 2016 Apr. 15. doi: 10.3727/096368916x691411. PubMed PMID: 27075659.
29. Choi S E, Jang H J, Kang Y, Jung J G, Han S J, Kim H J, Kim D J, Lee K W. Atherosclerosis induced by a high-fat diet is alleviated by lithium chloride via reduction of VCAM expression in ApoE-deficient mice. Vascular pharmacology. 2010; 53(5-6):264-72. Epub 2010 Oct. 5. doi: 10.1016/j.vph.2010.09.004. PubMed PMID: 20888430.
30. Kim S, Bong N, Kim O S, Jin J, Kim D E, Lee D K. Lithium chloride suppresses LPS-mediated matrix metalloproteinase-9 expression in macrophages through phosphorylation of GSK-3beta. Cell biology international. 2015; 39(2):177-84. Epub 2014 Jul. 24. doi: 10.1002/cbin.10352. PubMed PMID: 25053111.
31. Yang Y, Rosenberg G A. Matrix metalloproteinases as therapeutic targets for stroke. Brain research. 2015; 1623: 30-8. Epub 2015 Apr. 29. doi: 10.1016/j.brainres.2015.04.024. PubMed PMID: 25916577; PMCID: PMC4569515.
32. Ralay Ranaivo H, Hodge J N, Choi N, Wainwright M S. Albumin induces upregulation of matrix metalloproteinase-9 in astrocytes via MAPK and reactive oxygen species-dependent pathways. Journal of neuroinflammation. 2012; 9:68. Epub 2012 Apr. 18. doi: 10.1186/1742-2094-9-68. PubMed PMID: 22507553; PMCID: PMC3419618.
33. Cussotto S, Strain C R, Fouhy F, Strain R G, Peterson V L, Clarke G, Stanton C, Dinan T G, Cryan J F. Differential effects of psychotropic drugs on microbiome composition and gastrointestinal function. Psychopharmacology. 2018. Epub 2018 Aug. 30. doi: 10.1007/s00213-018-5006-5. PubMed PMID: 30155748.
34. Smith A J, Kim S H, Tan J, Sneed K B, Sanberg P R, Borlongan C V, Shytle R D. Plasma and Brain Pharmacokinetics of Previously Unexplored Lithium Salts. RSC advances. 2014; 4(24):12362-5. Epub 2014 Jul. 22. doi: 10.1039/c3ra46962j. PubMed PMID: 25045517; PMCID: PMC4100714.
35. Habib A, Sawmiller D, U S, Xiang Y, Rongo D, Tian J, Hou H, Zeng J, Smith A, Fan S, Giunta B, Mori T, Currier G, Shytle D R, Tan J. LISPRO mitigates beta-amyloid and associated pathologies in Alzheimer's mice. Cell death & disease. 2017; 8(6):e2880. Epub 2017 Jun. 16. doi: 10.1038/cddis.2017.279. PubMed PMID: 28617434; PMCID: PMC5520933.
36. Smith A J, Kim S H, Duggirala N K, Jin J, Wojtas L, Ehrhart J, Giunta B, Tan J, Zaworotko M J, Shytle R D. Improving lithium therapeutics by crystal engineering of novel ionic cocrystals. Mol Pharm. 2013; 10(12):4728-38. Epub 2013 Nov. 7. doi: 10.1021/mp400571a. PubMed PMID: 24191685; PMCID: PMC3850245.
37. Drayer N M, Lieberman S. ISOLATION O F CHOLESTEROL SULFATE FROM HUMAN BLOOD AND GALLSTONES. Biochemical and biophysical research communications. 1965; 18:126-30. Epub 1965 Jan. 4. PubMed PMID: 14265744.
38. Rodrigueza W V, Wheeler J J, Klimuk S K, Kitson C N, Hope M J. Transbilayer movement and net flux of cholesterol and cholesterol sulfate between liposomal membranes. Biochemistry. 1995; 34(18):6208-17. Epub 1995 May 9. PubMed PMID: 7742326.
39. Przybylska M, Faber M, Zaborowski A, Bryszewska M. Cholesterol sulfate induces changes in human erythrocyte thermostability. Biochemistry and molecular biology international. 1998; 46(2):399-410. Epub 1998 Nov. 5. PubMed PMID: 9801808.
40. Nielsen J, Kwon T H, Christensen B M, Frkiaer J, Nielsen S. Dysregulation of renal aquaporins and epithelial sodium channel in lithium-induced nephrogenic diabetes insipidus. Semin Nephrol. 2008; 28(3):227-44. doi: 10.1016/j.semnephrol.2008.03.002.
41. Alexander M P, Farag Y M, Mittal B V, Rennke H G, Singh A K. Lithium toxicity: a double-edged sword. Kidney Int. 2008; 73(2):233-7. Epub 2007 Oct. 17. PMID: 17943083.

What is claimed:

1. A solid, oral pharmaceutical composition consisting essentially of: a therapeutically effective amount of a lithium cholesterol, and one or more solid pharmaceutically acceptable carriers; wherein the lithium cholesterol has a structure having the formula:

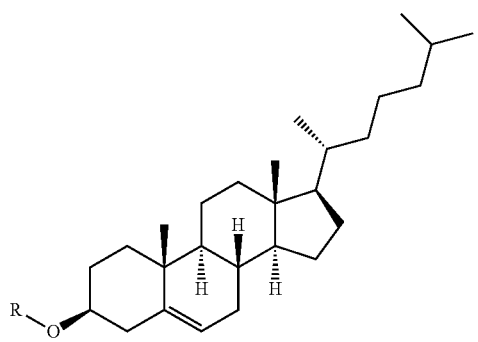

where R is selected from —$SO_3Li$, —$PO_3(Li)_2$, —$(CH_2)_n(C{=}O)OLi$, or —$(C{=}O)(CH_2)_n(C{=}O)OLi$, where n is integer selected from 1, 2, 3, 4, 5, and 6.

2. The solid, oral pharmaceutical composition of claim 1, wherein the lithium cholesterol is selected from a structure having the formula:

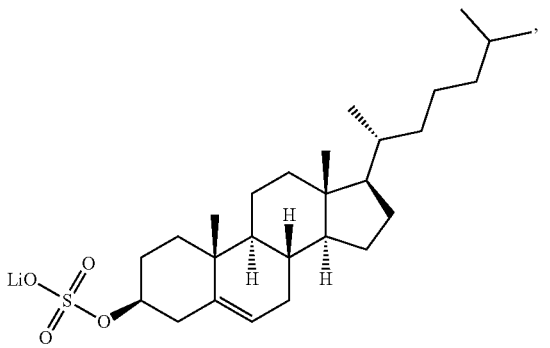

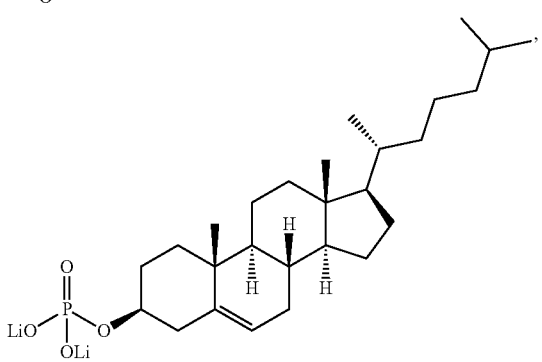

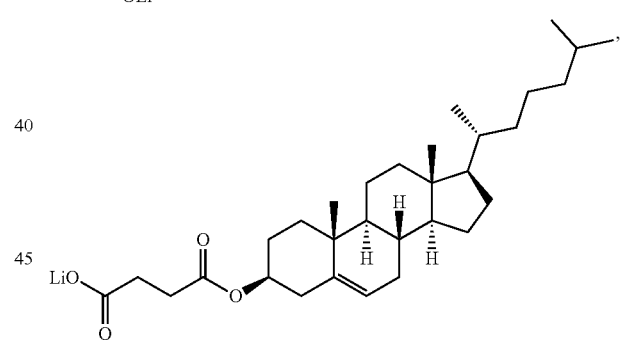

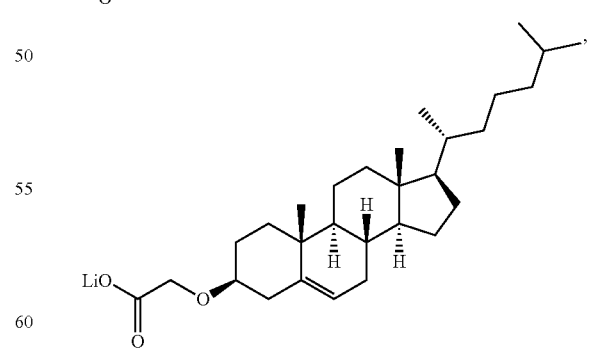

and combinations thereof.

3. The solid, oral pharmaceutical composition of claim 1, wherein the lithium cholesterol is a structure having the formula:

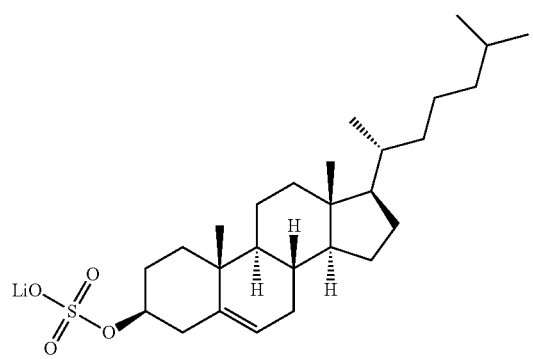

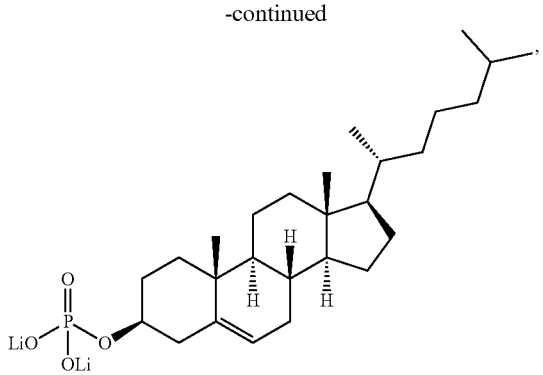

4. The solid, oral pharmaceutical composition of claim 1, wherein the one or more solid pharmaceutically acceptable carriers is selected from the group consisting of: diluents, excipients, extenders, preservatives, antioxidants, solubilizers, emulsifiers, coloring agents, releasing agents, coating agents, sweetening agents, flavoring agents, perfuming agents, and adjuvants.

5. A solid, oral pharmaceutical composition consisting of: a therapeutically effective amount of a lithium cholesterol, and one or more solid pharmaceutically acceptable carriers; wherein the lithium cholesterol has a structure having the formula:

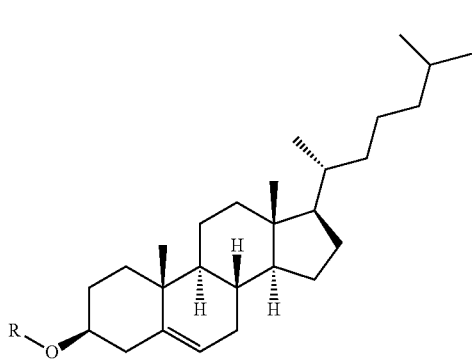

where R is selected from —$SO_3Li$, —$PO_3(Li)_2$, —$(CH_2)_n$(C=O)OLi, or —(C=O)$(CH_2)_n$(C=O)OLi, where n is integer selected from 1, 2, 3, 4, 5, and 6.

6. The pharmaceutical composition of claim 5, wherein the lithium cholesterol is selected from a structure having the formula:

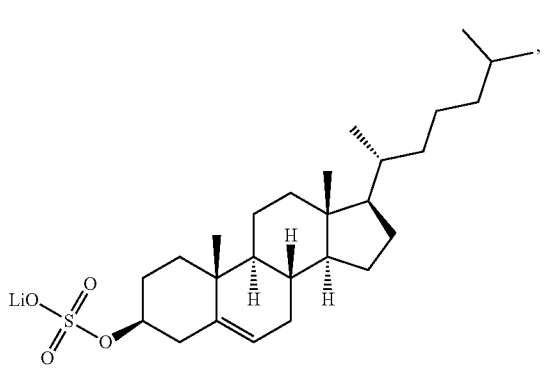

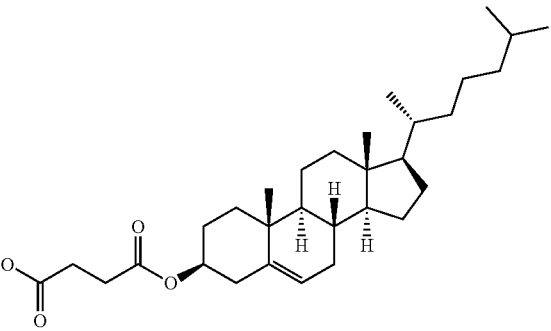

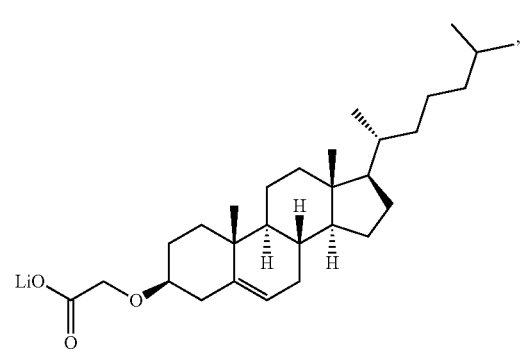

and combinations thereof.

* * * * *